United States Patent
Miserez et al.

(10) Patent No.: US 11,179,342 B2
(45) Date of Patent: Nov. 23, 2021

(54) PEPTIDE COACERVATES AND METHODS OF USE THEREOF

(71) Applicant: NANYANG TECHNOLOGICAL UNIVERSITY, Singapore (SG)

(72) Inventors: Ali Gilles Tchenguise Miserez, Singapore (SG); Yuan Ping, Singapore (SG); Zhi Wei Lim, Singapore (SG); Bartosz Piotr Gabryelczyk, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 16/447,641

(22) Filed: Jun. 20, 2019

(65) Prior Publication Data
US 2019/0388357 A1 Dec. 26, 2019

(30) Foreign Application Priority Data
Jun. 20, 2018 (SG) ............................ 10201805304Y

(51) Int. Cl.
| | |
|---|---|
| *A61K 38/28* | (2006.01) |
| *A61P 35/00* | (2006.01) |
| *A61P 3/10* | (2006.01) |
| *C07K 14/00* | (2006.01) |
| *A61K 9/50* | (2006.01) |
| *A61K 31/704* | (2006.01) |
| *A61K 41/00* | (2020.01) |
| *C07K 14/435* | (2006.01) |
| *A61K 38/44* | (2006.01) |

(52) U.S. Cl.
CPC .......... *A61K 9/5052* (2013.01); *A61K 9/5089* (2013.01); *A61K 9/5094* (2013.01); *A61K 31/704* (2013.01); *A61K 38/28* (2013.01); *A61K 38/443* (2013.01); *A61K 41/0028* (2013.01); *A61P 3/10* (2018.01); *A61P 35/00* (2018.01); *C07K 14/43504* (2013.01); *C12Y 101/03004* (2013.01)

(58) Field of Classification Search
CPC .... A61K 31/704; A61K 38/28; A61K 38/443; A61K 41/0028; A61K 9/5052; A61K 9/5089; A61K 9/5094; A61P 35/00; A61P 3/10; C07K 14/43504
USPC ............................ 514/6.7, 1.1; 530/300, 303
See application file for complete search history.

(56) References Cited

U.S. PATENT DOCUMENTS

| | | | | |
|---|---|---|---|---|
| 5,532,004 | A | * | 7/1996 | Bell .......................... A23G 4/20 426/5 |
| 2003/0032680 | A1 | * | 2/2003 | Singh ................... A61K 8/0275 516/38 |

OTHER PUBLICATIONS

Tan et al., "Layer-by-Layer Polyelectrolyte Deposition: A Mechanism for Forming Biocomposite Materials," Biomacromolecules, Apr. 9, 2013, 14: 1715-1726. (Year: 2013).*
Altschul et al., "Basic Local Alignment Search Tool," *J. Mol. Biol.* 215:403-410, 1990.
Altschul et al., "Gapped BLAST and PSI-BLAST: a new generation of protein database search programs," *Nucleic Acids Research* 25(17):3389-3402, 1997.
Aye et al., "Toward Closing the Loop: An Update on Insulin Pumps and Continuous Glucose Monitoring Systems," *Endocrinol Metab Clin N Am* 39(3):609-624, 2010.
Banani et al., "Biomolecular condensates: organizers of cellular biochemistry," *Molecular Cell Biology* 18:285-298, 2017.
Bankar et al., "Glucose oxidase—An overview," *Biotechnology Advances* 27:489-501, 2009.
Battelino et al., "Closed loop insulin delivery in diabetes," *Best Practice & Research Clinical Endocrinology & Metabolism* 29:315-325, 2015.
"Bioinspired materials science and bioengineering," retrieved from https://bioinspiredmaterials.berkeley.edu/research/mussel-inspired-adhesives/, Sep. 19, 2019, 3 pages.
Black et al., "Protein Encapsulation via Polypeptide Complex Coacervation," *ACS Macro Lett.* 3:1088-1091, 2014.
Boeynaems et al., "Protein Phase Separation: A New Phase in Cell Biology," *Trends in Cell Biology* 28(6):420-435, 2018.
Brady et al., "Structural and hydrodynamic properties of an intrinsically disordered region of a germ cell-specific protein on phase separation," *PNAS* 114(39):E8194-E8203, 2017.
Brangwynne et al., "Polymer physics of intercellular phase transitions," *Nature Physics* 11:899-904, 2015.
Brunetti et al., "Closed-loop delivery systems for insulin therapy," *The International Journal of Artificial Organs* 14(4): 216-226, 1991.
Burke et al., "Residue-by-Residue View of In Vitro FUS Granules that Bind the C-Terminal Domain of RNA Polymerase II," *Molecular Cell* 60:231-241, 2015.
Cai et al., "Self-coacervation of modular squid beak proteins—a comparative study," *Soft Matter* 13:7740-7752, 2017.
Chu et al., "Injectable fibroblast growth factor-2 coacervate for persistent angiogenesis," *PNAS* 108(33): 13444-13449, 2011.

(Continued)

*Primary Examiner* — Julie Ha
(74) *Attorney, Agent, or Firm* — Seed IP Law Group LLP

(57) ABSTRACT

Described herein is a composition for delivery of an active agent. The composition includes a peptide coacervate, wherein the peptide coacervate includes one or more peptides derived from histidine-rich proteins, and an active agent encapsulated in the peptide coacervate. Further provided are a method for encapsulation of an active agent in a peptide coacervate, a method for delivery of an active agent, and a method for treating or diagnosing a condition or disease in a subject in need thereof.

16 Claims, 53 Drawing Sheets
Specification includes a Sequence Listing.

(56) References Cited

OTHER PUBLICATIONS

Conicella et al., "ALS Mutations Disrupt Phase Separation Mediated by α-Helical Structure in the TDP-43 Low-Complexity C-Terminal Domain," *Structure* 24:1537-1549, 2016.
De Kruif et al., "Complex coacervation of proteins and anionic polysaccharides," *Current Opinion in Colloid & Interface Science* 9:340-349, 2004.
Dzuricky et al., "Convergence of Artificial Protein Polymers and Intrinsically Disordered Proteins," *Biochemistry* 57:2405-2414, 2018.
Elleri et al., "Closed-loop insulin delivery for treatment of type 1 diabetes," *BMC Medicine* 9(120): 1-9, 2011.
Farmer Jr et al., "The future of open- and closed-loop insulin delivery systems," *Journal of Pharmacy and Pharmacology* 60:1-13, 2008.
Frey et al., "FG-Rich Repeats of Nuclear Pore Proteins Form a Three-Dimensional Meshwork with Hydrogel-like Properties," *Science* 314(5800):815-817, 2006.
Galant et al., "Glucose: Detection and analysis," *Food Chemistry* 188:149-160, 2015.
García Quiroz et al., "Sequence heuristics to encode phase behaviour in intrinsically disordered protein polymers," *Nature Materials* 14:1164-1171, 2015 (9 pages).
Glatter, "A New Method for the Evaluation of Small-Angle Scattering Data," *J. Appl. Cryst.* 10:415-421, 1977.
Gu et al., "Glucose-Responsive Microgels Integrated with Enzyme Nanocapsules for Closed-Loop Insulin Delivery," *ACS Nano* 7(8):6758-6766, 2013.
Holehouse et al., "Functional Implications of Intracellular Phase Transitions," *Biochemistry* 57:2415-2423, 2018.
Hyman et al., "Liquid-Liquid Phase Separation in Biology," *Annu. Rev. Cell Dev. Biol.* 30:39-58, 2014.
Jiang et al., "Phase Transition of Spindle-Associated Protein Regulate Spindle Apparatus Assembly," *Cell* 163:108-122, 2015.
Johnson et al., "Coacervate delivery systems for proteins and small molecule drugs," *Expert Opin. Drug Deliv.* 11(12): 1829-1832, 2014.
Joshi et al., "pH and ionic strength induced complex coacervation of Pectin and Gelatin A," *Food Hydrocolloids* 74:132-138, 2018.
Kang et al., "A sulfonamide based glucose-responsive hydrogel with covalently immobilized glucose oxidase and catalase," *Journal of Controlled Release* 86:115-121, 2003.
Kato et al., "Cell-free Formation of RNA Granules: Low Complexity Sequence Domains Form Dynamic Fibers within Hydrogels," *Cell* 149:753-767, 2012.
Kim et al., "Complexation and coacervation of like-charged polyelectrolytes inspired by mussels," *PNAS* 113(7):E847-E853, 2016.
Kim et al., "Salt Triggers the Simple Coacervation of an Underwater Adhesive When Cations Meet Aromatic π Electrons in Seawater," *ACS Nano* 11:6764-6772, 2017.
Li et al., "pH-sensitive peptide hydrogel for glucose-responsive insulin delivery," *Acta Biomaterialia* 51:294-303, 2017.
Lim et al., "Glucose-Responsive Peptide Coacervates with High Encapsulation Efficiency for Controlled Release of Insulin," *Bioconjugate Chem.* 29:2176-2180, 2018.
Lin et al., "Intrinsically disordered sequences enable modulation of protein phase separation through distributed tyrosine motifs," *J. Biol. Chem.* 292(46):19110-19120, 2017.
Liu et al., "Stimuli-Responsive Capsule Membranes for Controlled Release in Pharmaceutical Applications," *Current Pharmaceutical Design* 23:295-301, 2017.
Martin et al., "Selective uptake and refolding of globular proteins in coacervate micro-droplets," *Langmuir* 32(23):5881-5889, 2016 (12 pages).
Meakin et al., "Ballistic deposition on surfaces," *Physical Review A* 34(6):5091-5103, 1986 (15 pages).
Mildner et al., "Small-angle scattering from porous solids with fractal geometry," *J. Phys. D: Appl. Phys.* 19:1535-1545, 1986.
Miserez et al., "Cross-linking Chemistry of Squid Beak," *The Journal of Biological Chemistry* 285(49):38115-38124, 2010 (11 pages).
Miserez et al., "The Transition from Stiff to Compliant Materials in Squid Beaks," *Science* 319(5871):1816-1819, 2008 (5 pages).
Miserez et al., "Jumbo squid beaks: Inspiration for design of robust organic composites," *Acta Biomaterialia* 3:139-149, 2007.
Mitrea et al., "Phase separation in biology; functional organization of a higher order," *Cell Communication and Signaling* 14(1): 1-20, 2016.
Mohammadi et al., "Phase transitions as intermediate steps in the formation of molecularly engineered protein fibers," *Communications Biology* 1(86): 1-12, 2018.
Mohammadi et al., "Self-Coacervation of a Silk-Like Protein and Its Use As an Adhesive for Cellulosic Materials," *ACS Macro Lett.* 7:1120-1125, 2018.
Morcombe et al., "Chemical shift referencing in MAS solid state NMR," *Journal of Magnetic Resonance* 162:479-486, 2003.
Muiznieks et al., "Role of Liquid-Liquid Phase Separation in Assembly of Elastin and Other Extracellular Matrix Proteins," *J Mol Biol* 430:4741-4753, 2018.
Murray et al., "Structure of FUS Protein Fibrils and Its Relevance to Self-Assembly and Phase Separation of Low-Complexity Domains," *Cell* 171:615-627, 2017.
Nott et al., "Phase Transition of a Disordered Nuage Protein Generates Environmentally Responsive Membraneless Organelles," *Molecular Cell* 57:936-947, 2015.
Orekhov et al., "Analysis of non-uniformly sampled spectra with multi-dimensional decomposition," *Progress in Nuclear Magnetic Resonance Spectroscopy* 59:211-292, 2011.
Pelton et al., "Tautomeric states of the active-site histidines of phosphorylated and unphosphorylated III$^{Glc}$, a signal-transducing protein from *Escherichia coli*, using two-dimensional heteronuclear NMR techniques," *Protein Science* 2:543-558, 1993.
Perry et al., "The Effect of Salt on the Complex Coacervation of Vinyl Polyelecrolytes," *Polymers* 6:1756-1772, 2014.
Pippa et al., "Complexation of cationic-neutral block polyelectrolyte with insulin and in vitro release studies," *International Journal of Pharmaceutics* 497:136-143, 2015.
Qi et al., "Salecan-Based pH-Sensitive Hydrogels for Insulin Delivery," *Mol. Pharmaceutics* 14:431-440, 2017.
Qi et al., "Triggered release of insulin from glucose-sensitive enzyme multilayer shells," *Biomaterials* 30:2799-2806, 2009.
Reichheld et al., "Direct observation of structure and dynamics during phase separation of an elastomeric protein," *PNAS* 114(22):E4408-4415, 2017.
Roberts et al., "Elastin-like polypeptides as models of intrinsically disordered proteins," *FEBS Letters* 589:2477-2486, 2015.
Schanda et al., "Very Fast Two-Dimensional NMR Spectroscopy for Real-Time Investigation of Dynamic Events in Proteins on the Time Scale of Seconds," *J. Am. Chem. Soc.* 127:8014-8015, 2005.
Shah et al., "Insulin delivery methods: Past, present and future," *International Journal of Pharmaceutical Investigation* 6(1):2016, (9 pages).
Shin et al., "Liquid phase condensation in cell physiology and disease," *Science* 357(6357):eaaf4382, 2017 (13 pages).
Solyom et al., "BEST-TROSY experiments for time-efficient sequential resonance assignment of large disordered proteins," *J Biomol NMR* 55:311-321, 2013.
Tai et al., "Bio-Inspired Synthetic Nanovesicles for Glucose-Responsive Release of Insulin," *Biomacromolecules* 15:3495-3502, 2014.
Tan et al., "Infiltration of chitin by protein coacervates defines the squid beak mechanical gradient," *Nature Chemical Biology* 11:488-495, 2015 (11 pages).
Thabit et al., "Bringing closed-loop home: recent advances in closed-loop insulin delivery," *Curr Opin Endocrinol Diabetes Obes* 21(2):95-101, 2014.
Thabit et al., "Closed-loop Insulin Delivery in Type 1 Diabetes," *Endocrinol Metab Clin North Am.* 41(1): 105-117, 2012 (NIH Public Access Author Manuscript, available in PMC Mar. 1, 2013)(16 pages).

(56) References Cited

OTHER PUBLICATIONS

Traitel et al., "Characterization of glucose-sensitive insulin release systems in simulated in vivo conditions," *Biomaterials* 21:1679-1687, 2000.

Uversky, "Protein intrinsic disorder-based liquid-liquid phase transitions in biological systems: Complex coacervates and membraneless organelles," *Advances in Colloid and Interface Science* 239:97-114, 2017.

Van der Lee et al., "Classification of Intrinsically Disordered Regions and Proteins," *Chem. Rev.* 114:6589-6631, 2014.

Van Geet, "Calibration of the Methanol and Glycol Nuclear Magnetic Resonance Thermometers with a Static Thermistor Probe," *Analytical Chemistry* 40(14):2227-2229, 1968.

Wang et al., "A Molecular Grammar Governing the Driving Forces for Phase Separation of Prion-like RNA Binding Proteins," *Cell* 174:688-699, 2018.

Wang et al., "Effects of Salt on Polyelectrolyte-Micelle Coacervation," *Macromolecules* 32:7128-7134, 1999.

Webber et al., "Smart approaches to glucose-responsive drug delivery," *J Drug Target* 23(7-8):651-655, 2015.

Wei et al., "A mussel-derived one component adhesive coacervate," *Acta Biomaterialia* 10:1663-1670, 2014.

Wei et al., "An Underwater Surface-Drying Peptide Inspired by a Mussel Adhesive Protein," *Adv. Funct. Mater.* 26:3496-3507, 2016.

Xiang et al., "The LC Domain of hnRNPA2 Adopts Similar Conformations in Hydrogel Polymers, Liquid-like Droplets, and Nuclei," *Cell* 163:829-839, 2015.

Xie et al., "Advances in pH-Sensitive Polymers for Smart Insulin Delivery," *Macromol. Rapid Commun.* 38:1700413, 2017 (14 pages).

Yaturu, "Insulin therapies: Current and future trends at dawn," *Word J Diabetes* 4(1): 1-7, 2013.

Yeo et al., "Coacervation of tropoelastin," *Advances in Colloid and Interface Science* 167:94-103, 2011.

Zhang et al., "Squid beak inspired water processable chitosan composites with tunable mechanical properties," *J. Mater. Chem. B* 4:2273-2279, 2016.

Zhao et al., "A glucose-responsive controlled release of insulin system based on enzyme multilayers-coated mesoporous silica particles," *Chem. Commun.* 47:9459-9461, 2011.

Zhao et al., "Cement Proteins of the Tube-building Polychaete Phragmatopoma californica," *The Journal of Biological Chemistry* 280(52):42938-42944, 2005.

Zhao et al., "Glucose Oxidase-Based Glucose-Sensitive Drug Delivery for Diabetes Treatment," *Polymers* 9(255): 1-21, 2017.

Zhao et al., "Glucose-sensitive polymer nanoparticles for self-regulated drug delivery," *Chem. Commun.* 52:7633-7652, 2016.

* cited by examiner

FIG. 2A DgHBP-2 peptide

| GHGVY | GHGVY | GHGPY | GHGPY | GHGLY W |

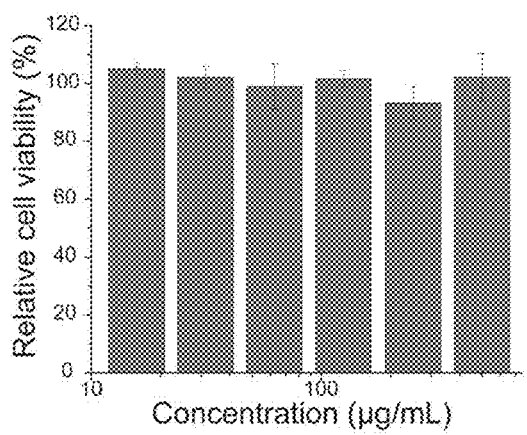
FIG. 5A
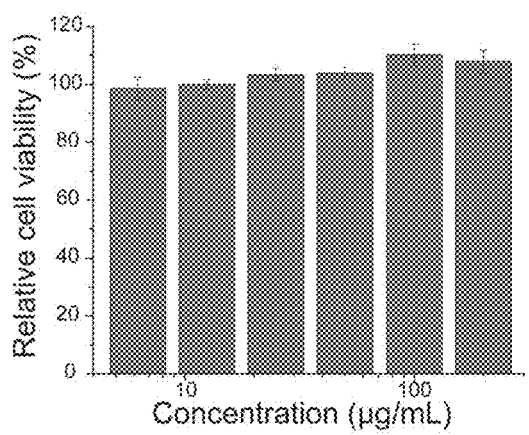
FIG. 5B
| FITC-Insulin (mg/mL) | DgHBP-2 peptide (mg/mL) | Encapsulation efficiency (%) |
|---|---|---|
| 0.01 | 1.0 | 99.7 ± 0.08 |
| 0.05 | 1.0 | 99.8 ± 0.05 |
| 0.10 | 1.0 | 99.8 ± 0.02 |
| 0.20 | 1.0 | 99.7 ± 0.02 |
| 0.40 | 1.0 | 99.3 ± 0.07 |
FIG. 6
| FITC-Insulin (mg/mL) | DgHBP-2 peptide (mg/mL) | Encapsulation efficiency (%) |
|---|---|---|
| 0.1 | 0.1 | 45.0 ± 2.97 |
| 0.1 | 0.3 | 94.4 ± 0.42 |
| 0.1 | 0.5 | 99.0 ± 0.12 |
| 0.1 | 1.0 | 99.8 ± 0.02 |
| 0.1 | 2.0 | 99.9 ± 0.01 |
FIG. 7

```
         10          20          30          40          50          60
MQLYGAPAVG  GVVENAVNAA  ESGAAATHDA  QGAYAEADTA  GVLDVNHAEH  HDGVHDASGY 70          80          90         100         110         120
GFGGLAGHCG  FAGHGLYGPG  FAGHGLLGAG  YAGLGLHGAG  FAGHGLHGAG  FAGHGLYGAG 130         140         150         160
FAGHGLHGFA  GHGLYGAGFA  GHGLGLGGLH  GALGHGALAH  Y
```

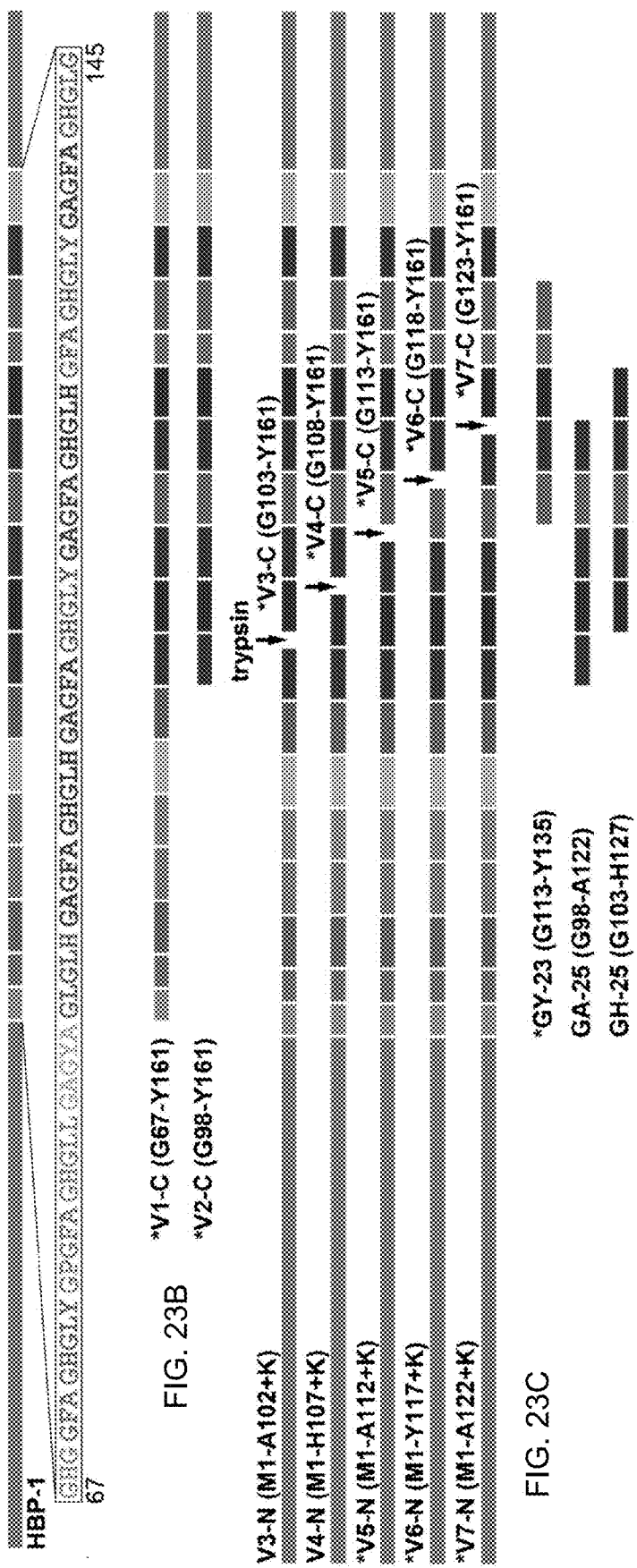

FIG. 24A

V1-C (6xHis-TEV-G67 - Y161)
HMHHHHHHSSGVDLGTENLYFQSMMGHGGFAGHGLYGPGFAGHGLLAGFAGLGLHGAGFAGHGLHGAG
FAGHGLYGAGFAGHGLHGFAGHGLYGAGFAGHGLGLGGLHGALGHGALAHY

V2-C (6xHis-TEV-G98 - Y161)
HMHHHHHHSSGVDLGTENLYFQSMMGAGFAGHGLHGAGFAGHGLYGAGFAGHGLHGFAGHGLYGAGFAG
HGLGLGGLHGALGHGALAHY

FIG. 24B

V3-N (M1 - A102)
MQLYGAPAVGGVVENAVNAAESGAAATHDAQGAYAEADTAGVLDVNHAEHHDGVHDASGYGFGGLAGHG
GFAGHGLYGPGFAGHGLLAGFAGLGLHGAGFAK

V4-N (M1 - H107)
MQLYGAPAVGGVVENAVNAAESGAAATHDAQGAYAEADTAGVLDVNHAEHHDGVHDASGYGFGGLAGHG
GFAGHGLYGPGFAGHGLLAGFAGLGLHGAGFAGHGLHK

V5-N (M1 - A112)
MQLYGAPAVGGVVENAVNAAESGAAATHDAQGAYAEADTAGVLDVNHAEHHDGVHDASGYGFGGLAGHG
GFAGHGLYGPGFAGHGLLAGFAGLGLHGAGFAGHGLHGAGFAK

V6-N (M1 - Y117)
MQLYGAPAVGGVVENAVNAAESGAAATHDAQGAYAEADTAGVLDVNHAEHHDGVHDASGYGFGGLAGHG
GFAGHGLYGPGFAGHGLLAGFAGLGLHGAGFAGHGLHGAGFAGHGLYK

V7-N (M1 - H122)
MQLYGAPAVGGVVENAVNAAESGAAATHDAQGAYAEADTAGVLDVNHAEHHDGVHDASGYGFGGLAGHG
GFAGHGLYGPGFAGHGLLAGFAGLGLHGAGFAGHGLHGAGFAGHGLYGAGFAK

V3-C (G103 - Y161)
GHGLHGAGFAGHGLYGAGFAGHGLHGFAGHGLYGAGFAGHGLGLGGLHGALGHGALAHY

V4-C (G108 - Y161)
GAGFAGHGLYGAGFAGHGLHGFAGHGLYGAGFAGHGLGLGGLHGALGHGALAHY

V5-C (G113 - Y161)
GHGLYGAGFAGHGLHGFAGHGLYGAGFAGHGLGLGGLHGALGHGALAHY

V6-C (G118 - Y161)
GAGFAGHGLHGFAGHGLYGAGFAGHGLGLGGLHGALGHGALAHY

V7-C (G123 - Y161)
GHGLHGFAGHGLYGAGFAGHGLGLGGLHGALGHGALAHY

GY-23 (G113 - Y135)
GHGLYGAGFAGHGLHGFAGHGLY

GA-25 (G98 - A122)
GAGFAGHGLHGAGFAGHGLYGAGFA

GH-25 (G103 - H127)
GHGLHGAGFAGHGLYGAGFAGHGLH

HBP-2 (M1 - L175)
MQFFGAGPFNTAHHSAVSDAAAAHHDAAGEYAQNAATGLLDTHHNENHDMTHDLANGYGLHEHDEQHHGL
ADGLHQEYAARAAQGANAVHNDAAQSHSALAAANTFGHGHAPYAAYGHGVYGHGPYGHGPYGHGLYGHGL
YGHGPYGHGLYGHGAPGHGLNAYAPLVGHGLRGYL

FIG. 25B

HBP-2-N (M1 - R81)
MQFFGAGPFNTAHHSAVSDAAAAHHDAAGEYAQNAATGLLDTHHNENHDMTHDLANGYGLHEHDEQHHGL
ADGLHQEYAAR

HBP-2-C (A82 - R172)
AAQGANAVHNDAAQSHSALAAANTFGHGHAPYAAYGHGVYGHGPYGHGPYGHGLYGHGLYGHGPYGHGLY
GHGAPGHGLNAYAPLVGHGLR

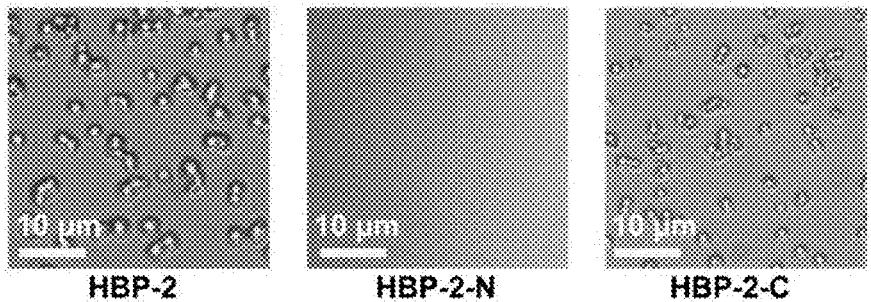

FIG. 25C

FIG. 26A
| name | sequence | LLPS |
|---|---|---|
| GY-25-V1 | GHGLY GAGFA GAGFA GAGFA GHGLY | yes |
| GY-25-V2 | GHGLY GHGLH GHGLH GHGLH GHGLY | yes |
| GY-20 | GHGLY GHGLY GHGLY GHGLY | yes |
| GY-15-V1 | GHGLY GHGLY GHGLY | no |
| GY-15-V2 | GHGLY GAGFA GHGLY | no |
| GY-10-V1 | GHGLY GHGLY | no |
| GY-10-V2 | GAGFA GHGLY | no |
| GY-10-V3 | GAGFA GHGFY | no |
| GA-5-V1 | GAGFA | no |
| GA-5-V2 | GHGLY | no |
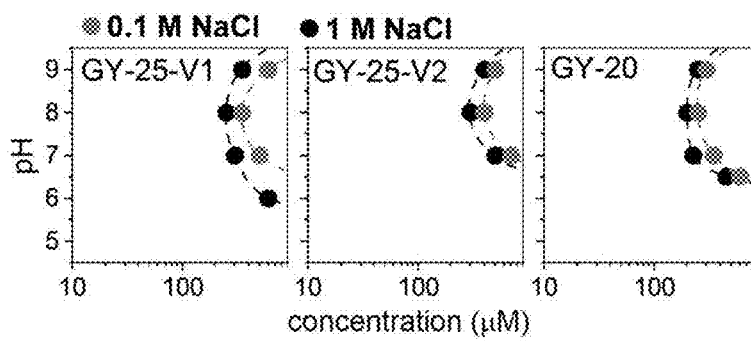
FIG. 26B
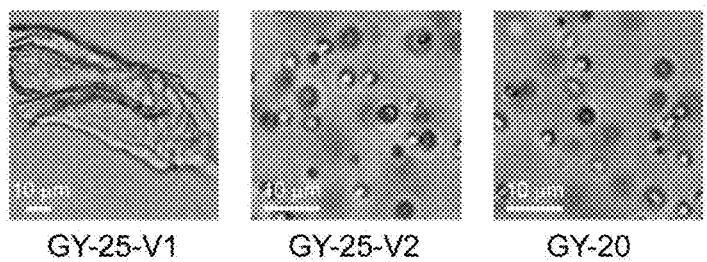
FIG. 26C
| GY-23 | GHGLY GAGFA GHGLH GFA GHGLY | yes |
|---|---|---|
| GY-23(5Y/A) | GHGLA GAGFA GHGLH GFA GHGLY | no |
| GY-23(23Y/A) | GHGLY GAGFA GHGLH GFA GHGLA | no |
FIG. 26D

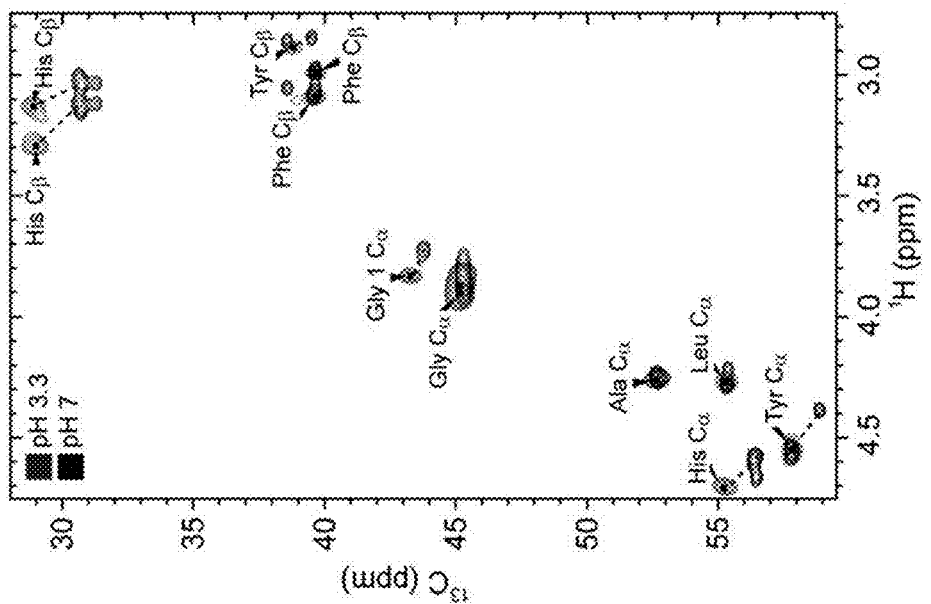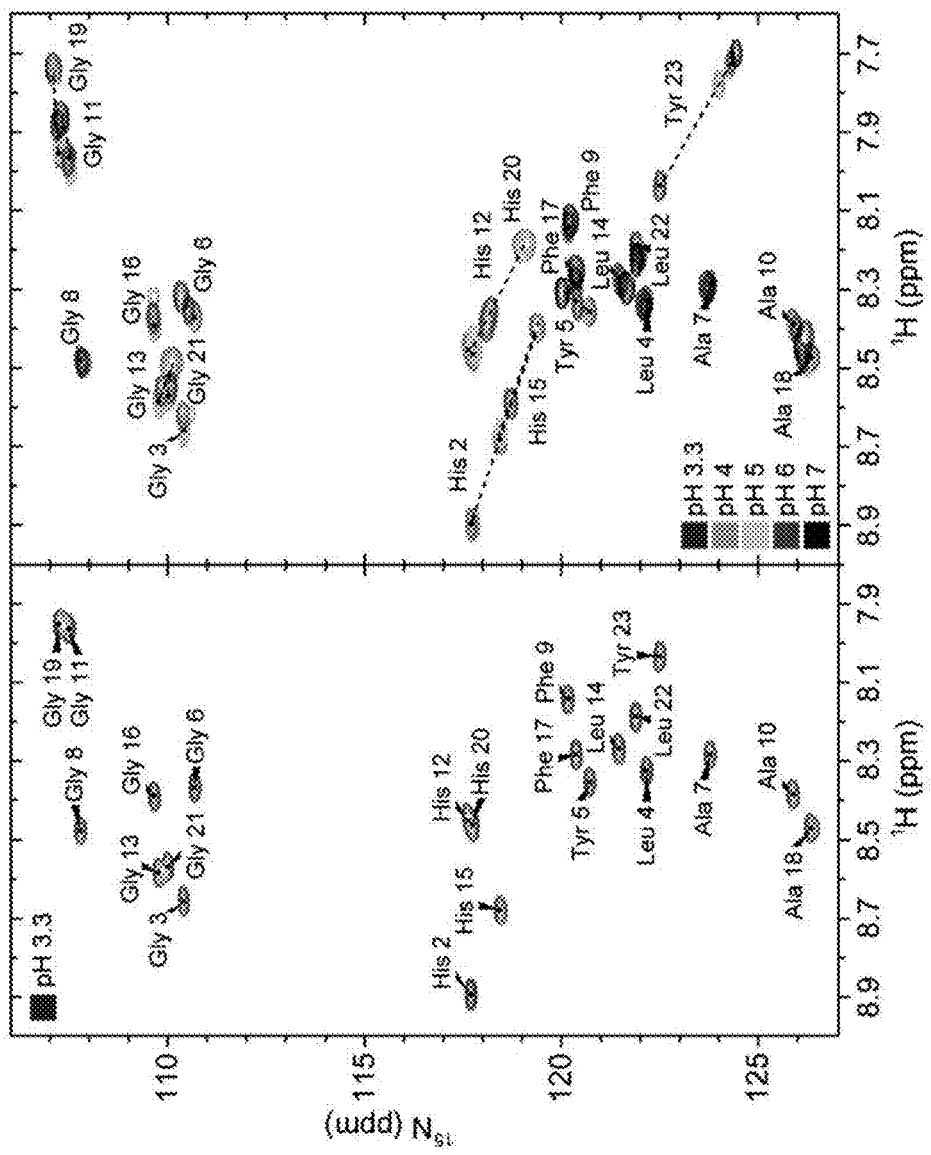

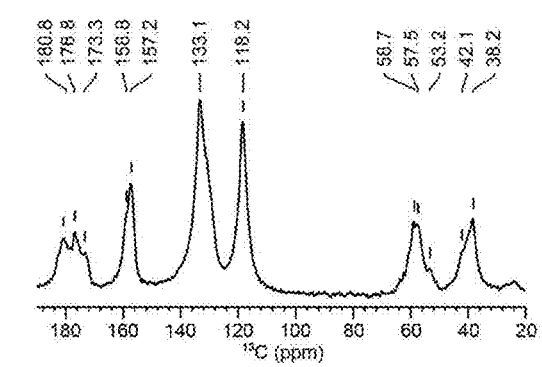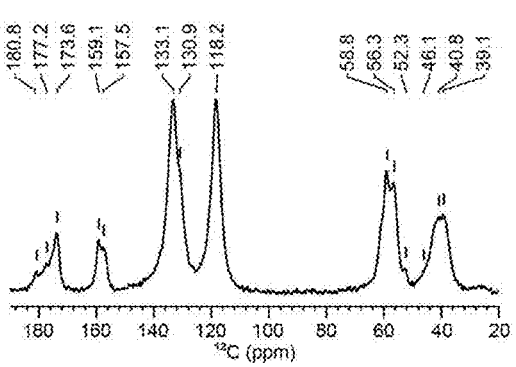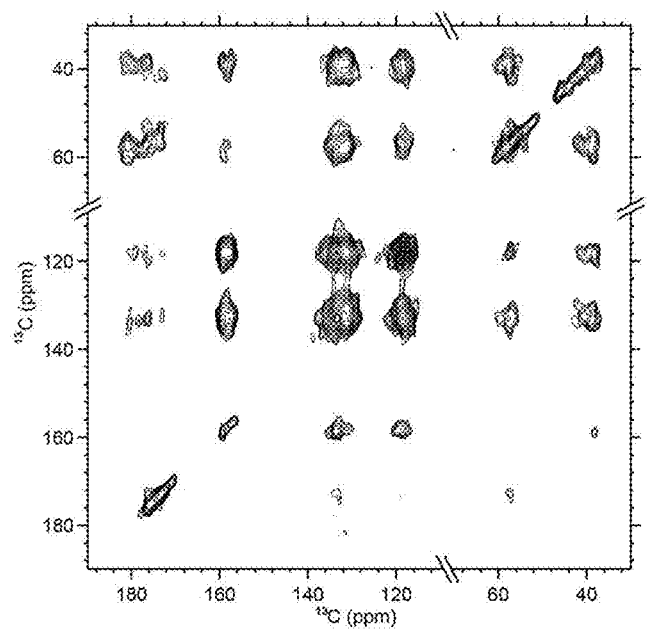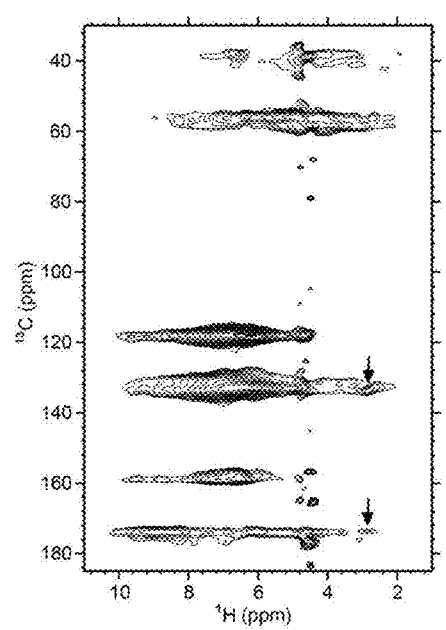
FIG. 33C                         FIG. 33D
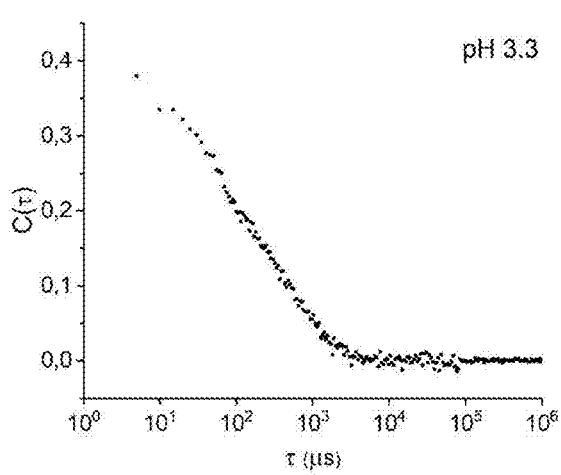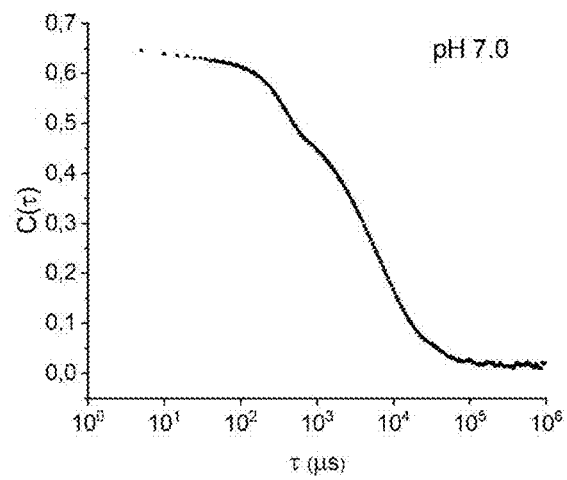
FIG. 34A                         FIG. 34B

| pH range | Buffer (50 mM) |
|---|---|
| 5.0 – 5.5 | Sodium acetate |
| 6.0 – 7.0 | Sodium phosphate |
| 7.5 – 9.0 | Tris-HCl |

FIG. 35

| Doxorubicin (mg/mL) | DgHBP-2 peptide (mg/mL) | Encapsulation efficiency (%) |
|---|---|---|
| 0.001 | 1.0 | 3.55 ± 3.26 |
| 0.003 | 1.0 | 16.50 ± 3.68 |
| 0.005 | 1.0 | 22.86 ± 1.22 |
| 0.010 | 1.0 | 31.55 ± 2.40 |
| 0.030 | 1.0 | 38.19 ± 2.62 |

FIG. 41A  FIG. 41B
A DgHBP-2 peptide
| GHGVY | GHGVY | GHGPY | GHGPY | GHGLY W |
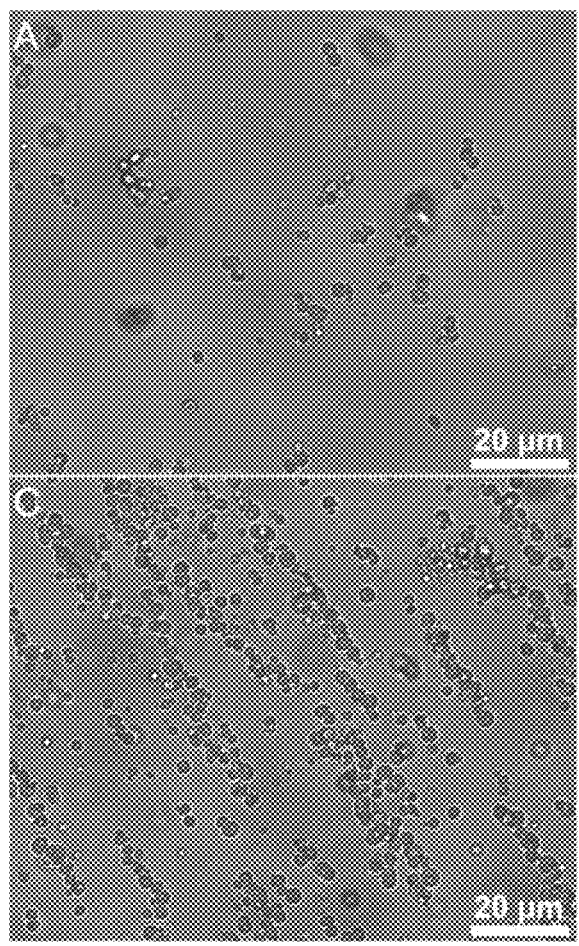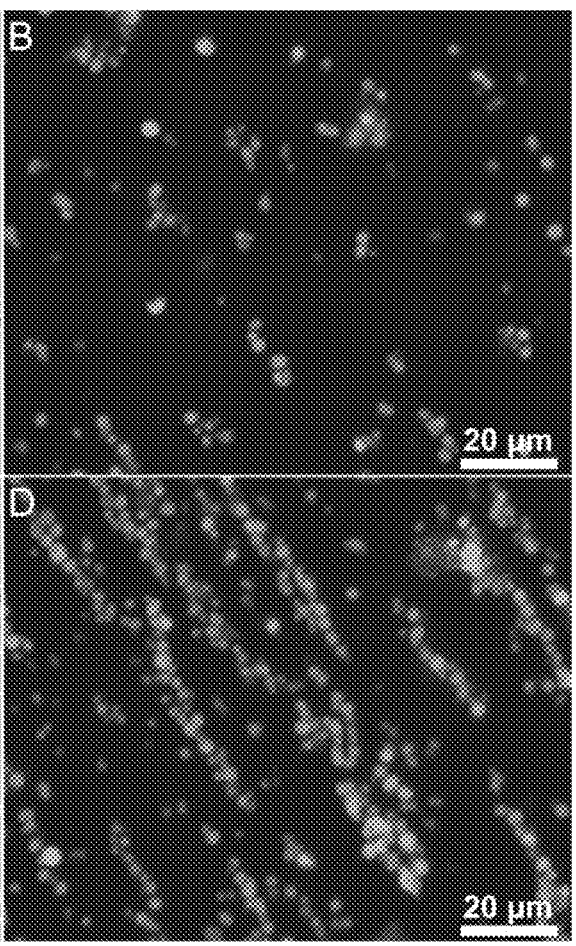
FIG. 41C  FIG. 41D
FIG. 42A 20 min crosslinking
FIG. 42B 16 hours crosslinking
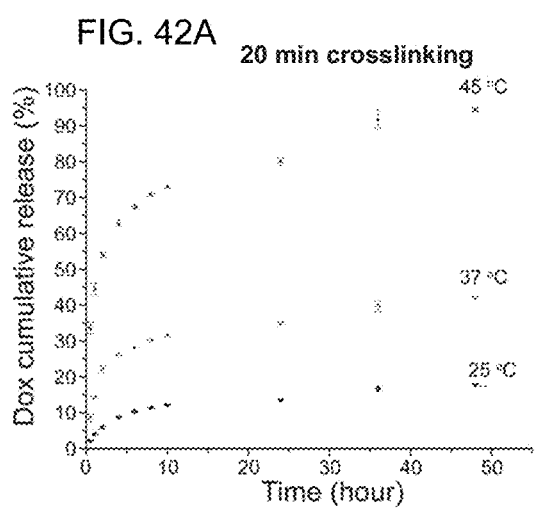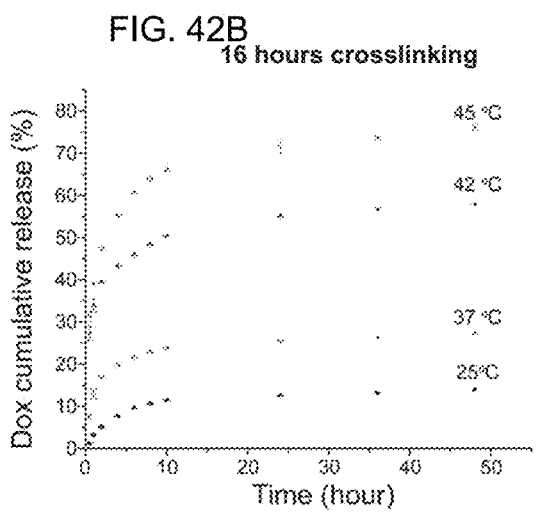

| E | Organ / tissue | |
|---|---|---|
| | Non coated | BSA coated |
| Liver |  | 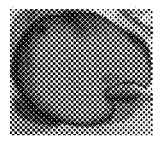 |
| Kidney | 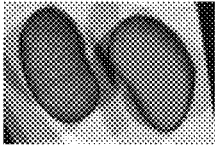 | 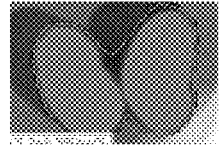 |
| Heart | 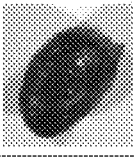 | 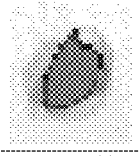 |
| Lungs | 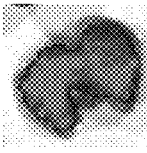 | 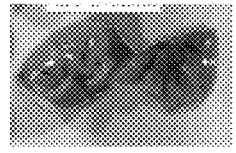 |
| Aorta |  |  |
| Spleen |  |  |
FIG. 50E

SEQUENCE LISTING

```
<160> NUMBER OF SEQ ID NOS: 54

<210> SEQ ID NO 1
<211> LENGTH: 160
<212> TYPE: PRT
<213> ORGANISM: Dosidicus gigas

<400> SEQUENCE: 1

Gln Leu Tyr Gly Ala Pro Ala Val Gly Gly Val Val Glu Asn Ala Val
1               5                   10                  15

Asn Ala Ala Glu Ser Gly Ala Ala Ala Thr His Asp Ala Gln Gly Ala
            20                  25                  30

Tyr Ala Glu Ala Asp Thr Ala Gly Val Leu Asp Val Asn His Ala Glu
        35                  40                  45

His His Asp Gly Val His Asp Ala Ser Gly Tyr Gly Phe Gly Gly Leu
    50                  55                  60

Ala Gly His Gly Gly Phe Ala Gly His Gly Leu Tyr Gly Pro Gly Phe
65                  70                  75                  80

Ala Gly His Gly Leu Leu Gly Ala Gly Tyr Ala Gly Leu Gly Leu His
            85                  90                  95

Gly Ala Gly Phe Ala Gly His Gly Leu His Gly Ala Gly Phe Ala Gly
            100                 105                 110

His Gly Leu Tyr Gly Ala Gly Phe Ala Gly His Gly Leu His Gly Phe
            115                 120                 125

Ala Gly His Gly Leu Tyr Gly Ala Gly Phe Ala Gly His Gly Leu Gly
        130                 135                 140

Leu Gly Gly Leu His Gly Ala Leu Gly His Gly Ala Leu Ala His Tyr
145                 150                 155                 160

<210> SEQ ID NO 2
<211> LENGTH: 174
<212> TYPE: PRT
<213> ORGANISM: Dosidicus gigas

<400> SEQUENCE: 2

Gln Phe Phe Gly Ala Gly Pro Phe Asn Thr Ala His His Ser Ala Val
1               5                   10                  15

Ser Asp Ala Ala Ala Ala His His Asp Ala Ala Gly Glu Tyr Ala Gln
            20                  25                  30

Asn Ala Ala Thr Gly Leu Leu Asp Thr His His Asn Glu Asn His Asp
            35                  40                  45

Met Thr His Asp Leu Ala Asn Gly Tyr Gly Leu His Glu His Asp Glu
    50                  55                  60

Gln His His Gly Leu Ala Asp Gly Leu His Gln Glu Tyr Ala Ala Arg
65                  70                  75                  80

Ala Ala Gln Gly Ala Asn Ala Val His Asn Asp Ala Ala Gln Ser His
            85                  90                  95
```

```
Ser Ala Leu Ala Ala Asn Thr Phe Gly His Gly His Ala Pro Tyr
            100                 105                 110

Ala Ala Tyr Gly His Gly Val Tyr Gly His Gly Pro Tyr Gly His Gly
        115                 120                 125

Pro Tyr Gly His Gly Leu Tyr Gly His Gly Leu Tyr Gly His Gly Pro
    130                 135                 140

Tyr Gly His Gly Leu Tyr Gly His Gly Ala Phe Gly His Gly Leu Asn
145                 150                 155                 160

Ala Tyr Ala Pro Leu Val Gly His Gly Leu Arg Gly Tyr Leu
                165                 170
```

```
<210> SEQ ID NO 3
<211> LENGTH: 26
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 3

Gly His Gly Xaa Tyr Gly His Gly Xaa Tyr Gly His Gly Xaa Tyr Gly
1               5                   10                  15

His Gly Xaa Tyr Gly His Gly Xaa Tyr Trp
            20                  25
```

```
<210> SEQ ID NO 4
<211> LENGTH: 25
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
```

-continued

```
<400> SEQUENCE: 4

Gly His Gly Xaa Tyr Gly His Gly Xaa Tyr Gly His Gly Xaa Tyr Gly
1               5                   10                  15

His Gly Xaa Tyr Gly His Gly Xaa Tyr
            20                  25

<210> SEQ ID NO 5
<211> LENGTH: 25
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 5

Gly His Gly Xaa Tyr Gly Ala Gly Phe Ala Gly His Gly Xaa Tyr Gly
1               5                   10                  15

Ala Gly Phe Ala Gly His Gly Xaa Tyr
            20                  25

<210> SEQ ID NO 6
<211> LENGTH: 25
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 6

Gly His Gly Xaa Tyr Gly His Gly Leu His Gly His Gly Leu His Gly
1               5                   10                  15

His Gly Leu His Gly His Gly Xaa Tyr
            20                  25

<210> SEQ ID NO 7
<211> LENGTH: 25
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 7

Gly His Gly Xaa Tyr Gly Ala Gly Phe Ala Gly Ala Gly Phe Ala Gly
```

```
1               5                   10                  15
Ala Gly Phe Ala Gly His Gly Xaa Tyr
            20                  25
```

<210> SEQ ID NO 8
<211> LENGTH: 20
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 8

```
Gly His Gly Xaa Tyr Gly His Gly Xaa Tyr Gly His Gly Xaa Tyr Gly
1               5                   10                  15

His Gly Xaa Tyr
            20
```

<210> SEQ ID NO 9
<211> LENGTH: 23
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 9

```
Gly His Gly Xaa Tyr Gly Ala Gly Phe Ala Gly His Gly Leu His Gly
1               5                   10                  15

Phe Ala Gly His Gly Xaa Tyr
            20
```

<210> SEQ ID NO 10
<211> LENGTH: 25
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 10

-continued

```
Gly His Gly Xaa Tyr Gly Ala Gly Phe Ala Gly His Gly Leu His Gly
1               5                   10                  15

Ala Gly Phe Ala Gly His Gly Xaa Tyr
            20                  25
```

<210> SEQ ID NO 11
<211> LENGTH: 25
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 11

```
Gly His Gly Xaa Tyr Gly His Gly Leu His Gly Ala Gly Phe Ala Gly
1               5                   10                  15

His Gly Leu His Gly His Gly Xaa Tyr
            20                  25
```

<210> SEQ ID NO 12
<211> LENGTH: 25
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 12

```
Gly His Gly Xaa Tyr Gly Ala Gly Phe Ala Gly Ala Gly Phe Ala Gly
1               5                   10                  15

His Gly Leu His Gly His Gly Xaa Tyr
            20                  25
```

<210> SEQ ID NO 13
<211> LENGTH: 25
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 13

```
Gly His Gly Xaa Tyr Gly His Gly Leu His Gly Ala Gly Phe Ala Gly
1               5                   10                  15

Ala Gly Phe Ala Gly His Gly Xaa Tyr
            20                  25
```

```
<210> SEQ ID NO 14
<211> LENGTH: 26
<212> TYPE: PRT
<213> ORGANISM: Artificial Sequence
<220> FEATURE:
<223> OTHER INFORMATION: Artificial peptide

<400> SEQUENCE: 14

Gly His Gly Val Tyr Gly His Gly Val Tyr Gly His Gly Pro Tyr Gly
1               5                   10                  15

His Gly Pro Tyr Gly His Gly Leu Tyr Trp
            20                  25

<210> SEQ ID NO 15
<211> LENGTH: 25
<212> TYPE: PRT
<213> ORGANISM: Artificial Sequence
<220> FEATURE:
<223> OTHER INFORMATION: Artificial peptide

<400> SEQUENCE: 15

Gly His Gly Val Tyr Gly His Gly Val Tyr Gly His Gly Pro Tyr Gly
1               5                   10                  15

His Gly Pro Tyr Gly His Gly Leu Tyr
            20                  25

<210> SEQ ID NO 16
<211> LENGTH: 25
<212> TYPE: PRT
<213> ORGANISM: Artificial Sequence
<220> FEATURE:
<223> OTHER INFORMATION: Artificial peptide

<400> SEQUENCE: 16

Gly His Gly Leu Tyr Gly Ala Gly Phe Ala Gly His Gly Leu Tyr Gly
1               5                   10                  15

Ala Gly Phe Ala Gly His Gly Leu Tyr
            20                  25

<210> SEQ ID NO 17
<211> LENGTH: 25
<212> TYPE: PRT
<213> ORGANISM: Artificial Sequence
<220> FEATURE:
<223> OTHER INFORMATION: Artificial peptide

<400> SEQUENCE: 17

Gly His Gly Leu Tyr Gly His Gly Leu His Gly His Gly Leu His Gly
1               5                   10                  15

His Gly Leu His Gly His Gly Leu Tyr
            20                  25

<210> SEQ ID NO 18
<211> LENGTH: 25
<212> TYPE: PRT
<213> ORGANISM: Artificial Sequence
<220> FEATURE:
<223> OTHER INFORMATION: Artificial peptide

<400> SEQUENCE: 18

Gly His Gly Leu Tyr Gly Ala Gly Phe Ala Gly Ala Gly Phe Ala Gly
1               5                   10                  15

Ala Gly Phe Ala Gly His Gly Leu Tyr
            20                  25
```

<210> SEQ ID NO 19
<211> LENGTH: 20
<212> TYPE: PRT
<213> ORGANISM: Artificial Sequence
<220> FEATURE:
<223> OTHER INFORMATION: Artificial peptide

<400> SEQUENCE: 19

```
Gly His Gly Leu Tyr Gly His Gly Leu Tyr Gly His Gly Leu Tyr Gly
1               5                   10                  15

His Gly Leu Tyr
            20
```

<210> SEQ ID NO 20
<211> LENGTH: 23
<212> TYPE: PRT
<213> ORGANISM: Artificial Sequence
<220> FEATURE:
<223> OTHER INFORMATION: Artificial peptide

<400> SEQUENCE: 20

```
Gly His Gly Leu Tyr Gly Ala Gly Phe Ala Gly His Gly Leu His Gly
1               5                   10                  15

Phe Ala Gly His Gly Leu Tyr
            20
```

<210> SEQ ID NO 21
<211> LENGTH: 25
<212> TYPE: PRT
<213> ORGANISM: Artificial Sequence
<220> FEATURE:
<223> OTHER INFORMATION: Artificial peptide

<400> SEQUENCE: 21

```
Gly His Gly Leu Tyr Gly Ala Gly Phe Ala Gly His Gly Leu His Gly
1               5                   10                  15

Ala Gly Phe Ala Gly His Gly Leu Tyr
            20                  25
```

<210> SEQ ID NO 22
<211> LENGTH: 25
<212> TYPE: PRT
<213> ORGANISM: Artificial Sequence
<220> FEATURE:
<223> OTHER INFORMATION: Artificial peptide

<400> SEQUENCE: 22

```
Gly His Gly Leu Tyr Gly His Gly Leu His Gly Ala Gly Phe Ala Gly
1               5                   10                  15

His Gly Leu His Gly His Gly Leu Tyr
            20                  25
```

<210> SEQ ID NO 23
<211> LENGTH: 25
<212> TYPE: PRT
<213> ORGANISM: Artificial Sequence
<220> FEATURE:
<223> OTHER INFORMATION: Artificial peptide

<400> SEQUENCE: 23

```
Gly His Gly Leu Tyr Gly Ala Gly Phe Ala Gly Ala Gly Phe Ala Gly
1               5                   10                  15

His Gly Leu His Gly His Gly Leu Tyr
            20                  25
```

```
<210> SEQ ID NO 24
<211> LENGTH: 25
<212> TYPE: PRT
<213> ORGANISM: Artificial Sequence
<220> FEATURE:
<223> OTHER INFORMATION: Artificial peptide

<400> SEQUENCE: 24

Gly His Gly Leu Tyr Gly His Gly Leu His Gly Ala Gly Phe Ala Gly
1               5                   10                  15

Ala Gly Phe Ala Gly His Gly Leu Tyr
            20                  25

<210> SEQ ID NO 25
<211> LENGTH: 5
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 25

Gly His Gly Xaa Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: Artificial peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 26

Gly His Gly Leu Xaa
1               5

<210> SEQ ID NO 27
<211> LENGTH: 5
<212> TYPE: PRT
<213> ORGANISM: Artificial Sequence
<220> FEATURE:
<223> OTHER INFORMATION: Artificial peptide

<400> SEQUENCE: 27

Gly Ala Gly Phe Ala
1               5

<210> SEQ ID NO 28
<211> LENGTH: 5
<212> TYPE: PRT
<213> ORGANISM: Artificial Sequence
<220> FEATURE:
<223> OTHER INFORMATION: Artificial peptide

<400> SEQUENCE: 28

Gly His Gly Leu His
1               5

<210> SEQ ID NO 29
```

```
<211> LENGTH: 79
<212> TYPE: PRT
<213> ORGANISM: Artificial Sequence
<220> FEATURE:
<223> OTHER INFORMATION: HBP-1 derived peptide

<400> SEQUENCE: 29

Gly His Gly Gly Phe Ala Gly His Gly Leu Tyr Gly Pro Gly Phe Ala
1               5                   10                  15

Gly His Gly Leu Leu Gly Ala Gly Tyr Ala Gly Leu Gly Leu His Gly
            20                  25                  30

Ala Gly Phe Ala Gly His Gly Leu His Gly Ala Gly Phe Ala Gly His
        35                  40                  45

Gly Leu Tyr Gly Ala Gly Phe Ala Gly His Gly Leu His Gly Phe Ala
    50                  55                  60

Gly His Gly Leu Tyr Gly Ala Gly Phe Ala Gly His Gly Leu Gly
65                  70                  75

<210> SEQ ID NO 30
<211> LENGTH: 119
<212> TYPE: PRT
<213> ORGANISM: Artificial Sequence
<220> FEATURE:
<223> OTHER INFORMATION: HBP-1 derived peptide V1-C

<400> SEQUENCE: 30

Met His His His His His His Ser Ser Gly Val Asp Leu Gly Thr Glu
1               5                   10                  15

Asn Leu Tyr Phe Gln Ser Met Met Gly His Gly Gly Phe Ala Gly His
            20                  25                  30

Gly Leu Tyr Gly Pro Gly Phe Ala Gly His Gly Leu Leu Gly Ala Gly
        35                  40                  45

Tyr Ala Gly Leu Gly Leu His Gly Ala Gly Phe Ala Gly His Gly Leu
    50                  55                  60

His Gly Ala Gly Phe Ala Gly His Gly Leu Tyr Gly Ala Gly Phe Ala
65                  70                  75                  80

Gly His Gly Leu His Gly Phe Ala Gly His Gly Leu Tyr Gly Ala Gly
                85                  90                  95

Phe Ala Gly His Gly Leu Gly Leu Gly Gly Leu His Gly Ala Leu Gly
            100                 105                 110

His Gly Ala Leu Ala His Tyr
        115

<210> SEQ ID NO 31
<211> LENGTH: 88
<212> TYPE: PRT
<213> ORGANISM: Artificial Sequence
<220> FEATURE:
<223> OTHER INFORMATION: HBP-1 derived peptide V2-C

<400> SEQUENCE: 31

Met His His His His His His Ser Ser Gly Val Asp Leu Gly Thr Glu
1               5                   10                  15

Asn Leu Tyr Phe Gln Ser Met Met Gly Ala Gly Phe Ala Gly His Gly
            20                  25                  30

Leu His Gly Ala Gly Phe Ala Gly His Gly Leu Tyr Gly Ala Gly Phe
        35                  40                  45

Ala Gly His Gly Leu His Gly Phe Ala Gly His Gly Leu Tyr Gly Ala
    50                  55                  60
```

Gly Phe Ala Gly His Gly Leu Gly Leu Gly Leu His Gly Ala Leu
65                  70                  75                  80

Gly His Gly Ala Leu Ala His Tyr
                85

<210> SEQ ID NO 32
<211> LENGTH: 103
<212> TYPE: PRT
<213> ORGANISM: Artificial Sequence
<220> FEATURE:
<223> OTHER INFORMATION: HBP-1 derived peptide V3-N

<400> SEQUENCE: 32

Met Gln Leu Tyr Gly Ala Pro Ala Val Gly Gly Val Val Glu Asn Ala
1               5                   10                  15

Val Asn Ala Ala Glu Ser Gly Ala Ala Ala Thr His Asp Ala Gln Gly
            20                  25                  30

Ala Tyr Ala Glu Ala Asp Thr Ala Gly Val Leu Asp Val Asn His Ala
        35                  40                  45

Glu His His Asp Gly Val His Asp Ala Ser Gly Tyr Gly Phe Gly Gly
    50                  55                  60

Leu Ala Gly His Gly Gly Phe Ala Gly His Gly Leu Tyr Gly Pro Gly
65                  70                  75                  80

Phe Ala Gly His Gly Leu Leu Gly Ala Gly Tyr Ala Gly Leu Gly Leu
                85                  90                  95

His Gly Ala Gly Phe Ala Lys
            100

<210> SEQ ID NO 33
<211> LENGTH: 98
<212> TYPE: PRT
<213> ORGANISM: Artificial Sequence
<220> FEATURE:
<223> OTHER INFORMATION: HBP-1 derived peptide V4-N

<400> SEQUENCE: 33

Met Gln Leu Tyr Gly Ala Pro Ala Val Gly Gly Val Val Glu Asn Ala
1               5                   10                  15

Val Asn Ala Ala Glu Ser Gly Ala Ala Ala Thr His Asp Ala Gln Gly
            20                  25                  30

Ala Tyr Ala Glu Ala Asp Thr Ala Gly Val Leu Asp Val Asn His Ala
        35                  40                  45

Glu His His Asp Gly Val His Asp Ala Ser Gly Tyr Gly Phe Gly Gly
    50                  55                  60

Leu Ala Gly His Gly Gly Phe Ala Gly His Gly Leu Tyr Gly Pro Gly
65                  70                  75                  80

Phe Ala Gly His Gly Leu Leu Gly Ala Gly Tyr Ala Gly Leu Gly Leu
                85                  90                  95

His Lys

<210> SEQ ID NO 34
<211> LENGTH: 113
<212> TYPE: PRT
<213> ORGANISM: Artificial Sequence
<220> FEATURE:
<223> OTHER INFORMATION: HBP-1 derived peptide V5-N

<400> SEQUENCE: 34

Met Gln Leu Tyr Gly Ala Pro Ala Val Gly Gly Val Val Glu Asn Ala
1               5                   10                  15

```
Val Asn Ala Ala Glu Ser Gly Ala Ala Ala Thr His Asp Ala Gln Gly
            20                  25                  30

Ala Tyr Ala Glu Ala Asp Thr Ala Gly Val Leu Asp Val Asn His Ala
        35                  40                  45

Glu His His Asp Gly Val His Asp Ala Ser Gly Tyr Gly Phe Gly Gly
    50                  55                  60

Leu Ala Gly His Gly Gly Phe Ala Gly His Gly Leu Tyr Gly Pro Gly
65                  70                  75                  80

Phe Ala Gly His Gly Leu Leu Gly Ala Gly Tyr Ala Gly Leu Gly Leu
                85                  90                  95

His Gly Ala Gly Phe Ala Gly His Gly Leu His Gly Ala Gly Phe Ala
            100                 105                 110

Lys

<210> SEQ ID NO 35
<211> LENGTH: 118
<212> TYPE: PRT
<213> ORGANISM: Artificial Sequence
<220> FEATURE:
<223> OTHER INFORMATION: HBP-1 derived peptide V6-N

<400> SEQUENCE: 35

Met Gln Leu Tyr Gly Ala Pro Ala Val Gly Gly Val Val Glu Asn Ala
1               5                   10                  15

Val Asn Ala Ala Glu Ser Gly Ala Ala Ala Thr His Asp Ala Gln Gly
            20                  25                  30

Ala Tyr Ala Glu Ala Asp Thr Ala Gly Val Leu Asp Val Asn His Ala
        35                  40                  45

Glu His His Asp Gly Val His Asp Ala Ser Gly Tyr Gly Phe Gly Gly
    50                  55                  60

Leu Ala Gly His Gly Gly Phe Ala Gly His Gly Leu Tyr Gly Pro Gly
65                  70                  75                  80

Phe Ala Gly His Gly Leu Leu Gly Ala Gly Tyr Ala Gly Leu Gly Leu
                85                  90                  95

His Gly Ala Gly Phe Ala Gly His Gly Leu His Gly Ala Gly Phe Ala
            100                 105                 110

Gly His Gly Leu Tyr Lys
        115

<210> SEQ ID NO 36
<211> LENGTH: 123
<212> TYPE: PRT
<213> ORGANISM: Artificial Sequence
<220> FEATURE:
<223> OTHER INFORMATION: HBP-1 derived peptide V7-N

<400> SEQUENCE: 36

Met Gln Leu Tyr Gly Ala Pro Ala Val Gly Gly Val Val Glu Asn Ala
1               5                   10                  15

Val Asn Ala Ala Glu Ser Gly Ala Ala Ala Thr His Asp Ala Gln Gly
            20                  25                  30

Ala Tyr Ala Glu Ala Asp Thr Ala Gly Val Leu Asp Val Asn His Ala
        35                  40                  45

Glu His His Asp Gly Val His Asp Ala Ser Gly Tyr Gly Phe Gly Gly
    50                  55                  60

Leu Ala Gly His Gly Gly Phe Ala Gly His Gly Leu Tyr Gly Pro Gly
65                  70                  75                  80
```

```
Phe Ala Gly His Gly Leu Leu Gly Ala Gly Tyr Ala Gly Leu Gly Leu
                85                  90                  95

His Gly Ala Gly Phe Ala Gly His Gly Leu His Gly Ala Gly Phe Ala
            100                 105                 110

Gly His Gly Leu Tyr Gly Ala Gly Phe Ala Lys
        115                 120
```

<210> SEQ ID NO 37
<211> LENGTH: 59
<212> TYPE: PRT
<213> ORGANISM: Artificial Sequence
<220> FEATURE:
<223> OTHER INFORMATION: HBP-1 derived peptide V3-C

<400> SEQUENCE: 37

```
Gly His Gly Leu His Gly Ala Gly Phe Ala Gly His Gly Leu Tyr Gly
1               5                   10                  15

Ala Gly Phe Ala Gly His Gly Leu His Gly Phe Ala Gly His Gly Leu
            20                  25                  30

Tyr Gly Ala Gly Phe Ala Gly His Gly Leu Gly Leu Gly Gly Leu His
        35                  40                  45

Gly Ala Leu Gly His Gly Ala Leu Ala His Tyr
    50                  55
```

<210> SEQ ID NO 38
<211> LENGTH: 54
<212> TYPE: PRT
<213> ORGANISM: Artificial Sequence
<220> FEATURE:
<223> OTHER INFORMATION: HBP-1 derived peptide V4-C

<400> SEQUENCE: 38

```
Gly Ala Gly Phe Ala Gly His Gly Leu Tyr Gly Ala Gly Phe Ala Gly
1               5                   10                  15

His Gly Leu His Gly Phe Ala Gly His Gly Leu Tyr Gly Ala Gly Phe
            20                  25                  30

Ala Gly His Gly Leu Gly Leu Gly Gly Leu His Gly Ala Leu Gly His
        35                  40                  45

Gly Ala Leu Ala His Tyr
    50
```

<210> SEQ ID NO 39
<211> LENGTH: 49
<212> TYPE: PRT
<213> ORGANISM: Artificial Sequence
<220> FEATURE:
<223> OTHER INFORMATION: HBP-1 derived peptide V5-C

<400> SEQUENCE: 39

```
Gly His Gly Leu Tyr Gly Ala Gly Phe Ala Gly His Gly Leu His Gly
1               5                   10                  15

Phe Ala Gly His Gly Leu Tyr Gly Ala Gly Phe Ala Gly His Gly Leu
            20                  25                  30

Gly Leu Gly Gly Leu His Gly Ala Leu Gly His Gly Ala Leu Ala His
        35                  40                  45

Tyr
```

<210> SEQ ID NO 40
<211> LENGTH: 44
<212> TYPE: PRT

-continued

```
<213> ORGANISM: Artificial Sequence
<220> FEATURE:
<223> OTHER INFORMATION: HBP-1 derived peptide V6-C

<400> SEQUENCE: 40

Gly Ala Gly Phe Ala Gly His Gly Leu His Gly Phe Ala Gly His Gly
1               5                   10                  15

Leu Tyr Gly Ala Gly Phe Ala Gly His Gly Leu Gly Leu Gly Gly Leu
            20                  25                  30

His Gly Ala Leu Gly His Gly Ala Leu Ala His Tyr
        35                  40

<210> SEQ ID NO 41
<211> LENGTH: 39
<212> TYPE: PRT
<213> ORGANISM: Artificial Sequence
<220> FEATURE:
<223> OTHER INFORMATION: HBP-1 derived peptide V7-C

<400> SEQUENCE: 41

Gly His Gly Leu His Gly Phe Ala Gly His Gly Leu Tyr Gly Ala Gly
1               5                   10                  15

Phe Ala Gly His Gly Leu Gly Leu Gly Gly Leu His Gly Ala Leu Gly
            20                  25                  30

His Gly Ala Leu Ala His Tyr
        35

<210> SEQ ID NO 42
<211> LENGTH: 25
<212> TYPE: PRT
<213> ORGANISM: Artificial Sequence
<220> FEATURE:
<223> OTHER INFORMATION: HBP-1 derived peptide GA-25

<400> SEQUENCE: 42

Gly Ala Gly Phe Ala Gly His Gly Leu His Gly Ala Gly Phe Ala Gly
1               5                   10                  15

His Gly Leu Tyr Gly Ala Gly Phe Ala
            20                  25

<210> SEQ ID NO 43
<211> LENGTH: 25
<212> TYPE: PRT
<213> ORGANISM: Artificial Sequence
<220> FEATURE:
<223> OTHER INFORMATION: HBP-1 derived peptide GH-25

<400> SEQUENCE: 43

Gly His Gly Leu His Gly Ala Gly Phe Ala Gly His Gly Leu Tyr Gly
1               5                   10                  15

Ala Gly Phe Ala Gly His Gly Leu His
            20                  25

<210> SEQ ID NO 44
<211> LENGTH: 81
<212> TYPE: PRT
<213> ORGANISM: Artificial Sequence
<220> FEATURE:
<223> OTHER INFORMATION: N-terminal fragment of HBP-2

<400> SEQUENCE: 44

Met Gln Phe Phe Gly Ala Gly Pro Phe Asn Thr Ala His His Ser Ala
1               5                   10                  15
```

-continued

Val Ser Asp Ala Ala Ala His His Asp Ala Ala Gly Glu Tyr Ala
            20                  25                  30

Gln Asn Ala Ala Thr Gly Leu Leu Asp Thr His His Asn Glu Asn His
                35                  40                  45

Asp Met Thr His Asp Leu Ala Asn Gly Tyr Gly Leu His Glu His Asp
 50                  55                  60

Glu Gln His His Gly Leu Ala Asp Gly Leu His Gln Glu Tyr Ala Ala
 65                  70                  75                  80

Arg

<210> SEQ ID NO 45
<211> LENGTH: 91
<212> TYPE: PRT
<213> ORGANISM: Artificial Sequence
<220> FEATURE:
<223> OTHER INFORMATION: C-terminal fargment of HBP-2

<400> SEQUENCE: 45

Ala Ala Gln Gly Ala Asn Ala Val His Asn Asp Ala Ala Gln Ser His
 1               5                  10                  15

Ser Ala Leu Ala Ala Ala Asn Thr Phe Gly His Gly His Ala Pro Tyr
                20                  25                  30

Ala Ala Tyr Gly His Gly Val Tyr Gly His Gly Pro Tyr Gly His Gly
            35                  40                  45

Pro Tyr Gly His Gly Leu Tyr Gly His Gly Leu Tyr Gly His Gly Pro
 50                  55                  60

Tyr Gly His Gly Leu Tyr Gly His Gly Ala Phe Gly His Gly Leu Asn
 65                  70                  75                  80

Ala Tyr Ala Pro Leu Val Gly His Gly Leu Arg
                85                  90

<210> SEQ ID NO 46
<211> LENGTH: 5
<212> TYPE: PRT
<213> ORGANISM: Artificial Sequence
<220> FEATURE:
<223> OTHER INFORMATION: Artificial peptide

<400> SEQUENCE: 46

Gly His Gly Leu Tyr
 1               5

<210> SEQ ID NO 47
<211> LENGTH: 10
<212> TYPE: PRT
<213> ORGANISM: Artificial Sequence
<220> FEATURE:
<223> OTHER INFORMATION: Artificial peptide

<400> SEQUENCE: 47

Gly His Gly Leu Tyr Gly His Gly Leu Tyr
 1               5                  10

<210> SEQ ID NO 48
<211> LENGTH: 15
<212> TYPE: PRT
<213> ORGANISM: Artificial Sequence
<220> FEATURE:
<223> OTHER INFORMATION: Artificial peptide

<400> SEQUENCE: 48

Gly His Gly Leu Tyr Gly His Gly Leu Tyr Gly His Gly Leu Tyr

```
<210> SEQ ID NO 49
<211> LENGTH: 15
<212> TYPE: PRT
<213> ORGANISM: Artificial Sequence
<220> FEATURE:
<223> OTHER INFORMATION: Artificial peptide GY-15-V2

<400> SEQUENCE: 49

Gly His Gly Leu Tyr Gly Ala Gly Phe Ala Gly His Gly Leu Tyr
1               5                   10                  15

<210> SEQ ID NO 50
<211> LENGTH: 10
<212> TYPE: PRT
<213> ORGANISM: Artificial Sequence
<220> FEATURE:
<223> OTHER INFORMATION: Artificial peptide GY-10-V2

<400> SEQUENCE: 50

Gly Ala Gly Tyr Ala Gly His Gly Leu Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Artificial peptide GY-V10-V3

<400> SEQUENCE: 51

Gly Ala Gly Phe Ala Gly His Gly Pro Tyr
1               5                   10

<210> SEQ ID NO 52
<211> LENGTH: 23
<212> TYPE: PRT
<213> ORGANISM: Artificial Sequence
<220> FEATURE:
<223> OTHER INFORMATION: Mutant of GY-23

<400> SEQUENCE: 52

Gly His Gly Leu Ala Gly Ala Gly Phe Ala Gly His Gly Leu His Gly
1               5                   10                  15

Phe Ala Gly His Gly Leu Tyr
            20

<210> SEQ ID NO 53
<211> LENGTH: 23
<212> TYPE: PRT
<213> ORGANISM: Artificial Sequence
<220> FEATURE:
<223> OTHER INFORMATION: Mutant of GY-23

<400> SEQUENCE: 53

Gly His Gly Leu Tyr Gly Ala Gly Phe Ala Gly His Gly Leu His Gly
1               5                   10                  15

Phe Ala Gly His Gly Leu Ala
            20

<210> SEQ ID NO 54
<211> LENGTH: 5
<212> TYPE: PRT
<213> ORGANISM: Artificial Sequence
<220> FEATURE:
```

<223> OTHER INFORMATION: Artificial peptide

<400> SEQUENCE: 54

Gly His Gly Leu Gly
1               5

PEPTIDE COACERVATES AND METHODS OF USE THEREOF

CROSS REFERENCE TO RELATED APPLICATIONS

This application claims priority to Singapore Application No. 10201805304Y entitled "Peptide Coacervates For Encapsulation of Insulin With High Efficiency And Glucose-Responsive Release", filed on Jun. 20, 2018, the disclosures of which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_558_SEQUENCE_LISTING.txt. The text file is 28 KB, was created on Jun. 19, 2019, and is being submitted electronically via EFS-Web.

TECHNICAL FIELD

The present invention lies in the field of targeted delivery of active agents using peptide coacervates and methods of coacervate formation and active agent encapsulation.

BACKGROUND

The Humboldt squid beak includes a hard biomolecular composite made of chitin and proteins. The squid beak proteins were recently isolated and sequenced and two families of proteins, chitin binding beak proteins (DgCBPs) and histidine-rich beak proteins (DgHBPs) were discovered within the beak. DgCBPs likely bind to chitin to form a chitin-DgCBPs scaffold, while DgHBPs exhibit self-coacervation ability, a liquid-liquid phase separation (LLPS) process resulting in the formation of highly concentrated protein microdroplets. DgHBP coacervates have been hypothesized to infiltrate the chitin-DgCBPs scaffold (Tan et al. (2015) Nat. Chem. Biol. 11 (7), 488-95) followed by interchain covalent cross-linking during maturation, with the very high cross-link density imparting the beak with its impressive mechanical properties (Miserez et al. (2007) Acta Biomater. 3 (1), 139-49; Miserez et al. (2010) J. Biol. Chem. 285 (49), 38115-24). The DgHBPs identified have been sequenced and have been found to exhibit a two-domain organisation. The N-terminal domains contain non-repetitive, long stretches of Alanine (Ala) and Histidine (His)-rich regions, whereas the C-terminal domains includes tandem His- and Gly-rich penta-repeats (GAGFA, GHGXX'/X" or GHGXY, where X represents a hydrophobic residue, X' usually represents tyrosine and X" represents either glycine or alanine. The C-terminal domain motifs were found to be responsible for DgHBPs self-coacervation properties (Cai et al. (2017) Soft Matter 13 (42), 7740-7752).

Coacervation or LLPS is the demixing of a homogeneous polymer solution into two distinct phases: a concentrated macromolecule-rich (or coacervate) phase and a dilute macromolecule-depleted phase. While coacervation studies were initiated in the field of biopolymeric colloids, in recent years LLPS has attracted considerable interest from life scientists, with numerous studies showing its role in organizing biomolecules in living cells via formation of membrane-less organelles. Another less recognized but increasingly appreciated biological role of LLPS is associated with the assembly of extracellular, load-bearing structures (Muiznieks et al. (2018) J. Mol. Biol. doi:10.1016/J.JMB.2018.06.010). A well-known example is tropoelastin, which undergoes self-coacervation upon secretion into the extracellular matrix where it self-assembles to form elastic fibers that provide strength and resilience to elastic tissues (Yeo et al. (2011) Adv. Colloid Interface Sci. 167, 94-103). Coacervation has also been recognized to play a key role in natural bioadhesives secreted by marine invertebrates, for example the sandcastle tubeworm or mussels (Wei et al. (2014) Acta Biomater. 10, 1663-1670) and to be involved in the formation of biological composite materials.

Recent studies of proteins involved in LLPS have revealed that they usually belong to the family of intrinsically disordered proteins (IDPs) or contain intrinsically disordered regions (IDRs). Such proteins/regions are characterized by very dynamic molecular conformations and a low sequence complexity with a modular organization of their primary structure (Brangwynne, et al. (2015) Nat. Phys. 11, 899-904; Uversky (2017) Adv. Colloid Interface Sci. 239, 97-114; Van Der Lee et al. (2014) Chem. Rev. 114, 6589-6631). As a result, they lack the well-defined three-dimensional structure typical of globular proteins.

It has been suggested that various intra- or intermolecular interactions are involved during LLPS of IDPs/IDRs, for example multivalent (cooperative), electrostatic, hydrophobic, or cation-7 interactions. Structure-function relationships of IDPs have primarily been obtained by site-directed mutagenesis, establishing the contributions of individual residues to the phase separation process. However, molecular-scale interactions behind LLPS are still sparsely understood.

While in various fields of technology, in particular in pharmaceutical, diagnostic, chemical and biological applications, a multitude of delivery methods are known, there is still need for novel and improved delivery systems, in particular those suited to deliver pharmaceutically active agents to a patient in need thereof, including release of the pharmaceutically active agents at a specific site at a specific time or over a specific time period or if a specific condition is met.

Such delivery systems would, for example, be useful in the treatment and management of diabetes. Diabetes is a chronic metabolic disease that is characterized by abnormal high levels of fasting blood glucose. As a general practice, insulin is often administrated to control the blood glucose level in both type I and II diabetic patients. To obtain ideal therapeutic results, a strict insulin administration program is needed for diabetic patients. Hence, many investigations have been dedicated to develop environment-responsive delivery systems. Commonly, a glucose-responsive insulin delivery system (GRIDS) is able to sense the increased glucose concentration and subsequently release the required amount of insulin according to the glucose level (Farmer et al. (2008) J. Pharm. Pharmacol. 60 (1), 1-13; Thabit and Hovorka (2014) Curr. Opin. Endocrinol. Diabetes Obes. 21 (2), 95-101; Battelino et al. (2015) Best Pract Res. Clin Endocrinol Metab 29 (3), 315-25; Xie et al. (2017) Macromol. Rapid Commun. 38 (23), 1700413).

GRIDS may not only replace the recurrent insulin injections, but can also reduce the patient's direct involvement in glucose control and prevent insulin from excessive or insufficient dosage (Yaturu (2013) World J. Diabetes 4 (1), 1-7; Shah et al. (2016) Int. J. Pharm. Investig 6 (1), 1-9; Webber and Anderson (2015) J. Drug Target 23 (7-8), 651-5). One approach used for sensing glucose is to incorporate a glucose-responsive element such as glucose oxidase (GOx) into the delivery system, whereby GOx catalyzes the conversion of D-glucose into gluconic acid to reduce the local pH (Webber and Anderson, supra; Li et al. (2017) Acta Biomater. 51, 294-303; Tai et al. (2014) Biomacromolecules 15 (10), 3495-502; Zhao et al. (2017) Polymers 9 (7), 255). The acidic pH subsequently results in the conformational or structural changes of the carrier and ultimately releases the insulin. Such a strategy has been notably employed in pH-responsive hydrogels (Zhao et al., supra).

Diabetes management is thus one example of a field where there is still particular need for efficient and controllable delivery systems.

SUMMARY

Peptide coacervates formed from peptides derived from histidine-rich proteins can be used for the efficient delivery of active agents. The peptide coacervates formed may co-encapsulate two or more active agents to be applicable and effective in the management and/or treatment of diseases or disorders, such as cancer or diabetes. Additionally, the inventors' findings provide general guidelines and concepts for designing (pH-responsive) peptides with liquid-liquid phase separation (LLPS) ability for various applications, including bio-inspired protocells and smart drug-delivery systems.

In a first aspect, a composition for delivery of an active agent may include a peptide coacervate, said peptide coacervate comprising peptides derived from histidine-rich proteins, and said active agent, wherein the active agent is encapsulated in the coacervate.

In various embodiments, the composition is an aqueous liquid two phase formulation, comprising (a) a coacervate colloidal phase comprising the peptides derived from histidine-rich proteins and the active agent; and (b) a dilute aqueous phase. In some embodiments, the colloidal phase has the form of droplets having substantially spherical shape with a diameter ranging from about 0.2 to about 5 μm.

In various non-limiting embodiments, the histidine-rich proteins are histidine-rich beak proteins (DgHBPs), for example derived from the beak of a squid, in particular the Humbold squid (*Dosidicus gigas*). The histidine-rich proteins may, for example, include, but not limited to, DgHBP-1 (SEQ ID NO:1) and DgHBP-2 (SEQ ID NO:2), with the peptides derived therefrom being, in various embodiments, fragments thereof that comprise at least one copy of the peptide motif GHGXY (SEQ ID NO:25), wherein X is valine (V), leucine (L) or proline (P), such as GHGLY (SEQ ID NO:46). Further motifs that may be comprised include, but are not limited to GHGLX (SEQ ID NO:26), wherein X is leucine (L), histidine (H), tyrosine (Y) or glycine (G), such as GHGLH (SEQ ID NO:28), and GAGFA (SEQ ID NO:27) and GFA.

In various embodiments, the peptides derived from histidine-rich proteins comprise the amino acid sequence

wherein $X^1$ is valine (V), leucine (L) or proline (P), $X^2$ is alanine (A) or proline (P); $X^3$ is phenylalanine (F) or tyrosine (Y), $X^4$ is leucine (L), histidine (H), tyrosine (Y) or glycine (G),
each a is 0 or an integer ≥1;
each b is 0 or an integer ≥1;
each c is 0 or an integer ≥1;

each d is 0 or an integer ≥1;
f is an integer ≥1;
with the sum of all a being ≥2 and the sum of all a+b+c+d is ≥4.

In non-limiting embodiments, the peptides derived from histidine-rich proteins may include an amino acid sequence, such as but not limited to:

(1)

wherein X is valine (V), leucine (L) or proline (P), and n is ≥4;

(2)

wherein X is valine (V), leucine (L) or proline (P); n is ≥1; m is ≥1; and i≥2;

(3)

wherein X is valine (V), leucine (L) or proline (P); n is ≥1; m is ≥1; and i≥2;

(4)

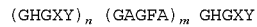

wherein X is valine (V), leucine (L) or proline (P); n is ≥1; and m is ≥2; and (5)

wherein X is valine (V), leucine (L) or proline (P); n is ≥1; and m is ≥2; and
(6) combinations of the above.

Non-limiting peptides may include an amino acid sequence, such as but not limited to, (i)
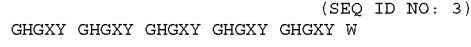
(SEQ ID NO: 3)
GHGXY GHGXY GHGXY GHGXY GHGXY W (ii)
(SEQ ID NO: 4)
GHGXY GHGXY GHGXY GHGXY GHGXY (iii)
(SEQ ID NO: 5)
GHGXY GAGFA GHGXY GAGFA GHGXY (iv)
(SEQ ID NO: 6)
GHGXY GHGLH GHGLH GHGLH GHGXY (v)
(SEQ ID NO: 7)
GHGXY GAGFA GAGFA GAGFA GHGXY (vi)
(SEQ ID NO: 8)
GHGXY GHGXY GHGXY GHGXY (vii)
(SEQ ID NO: 9)
GHGXY GAGFA GHGLH GFA GHGXY -continued (viii)
GHGXY GAGFA GHGLH GAGFA GHGXY (SEQ ID NO: 10)

(ix)
GHGXY GHGLH GAGFA GHGLH GHGXY (SEQ ID NO: 11)

(x)
GHGXY GAGFA GAGFA GHGLH GHGXY (SEQ ID NO: 12)

(xi)
GHGXY GHGLH GAGFA GAGFA GHGXY (SEQ ID NO: 13)

(xii)
GHGVY GHGVY GHGPY GHGPY GHGLY W (SEQ ID NO: 14)

(xiii)
GHGVY GHGVY GHGPY GHGPY GHGLY (SEQ ID NO: 15)

(xiv)
GHGLY GAGFA GHGLY GAGFA GHGLY (SEQ ID NO: 16)

(xv)
GHGLY GHGLH GHGLH GHGLH GHGLY (SEQ ID NO: 17)

(xvi)
GHGLY GAGFA GAGFA GAGFA GHGLY (SEQ ID NO: 18)

(xvii)
GHGLY GHGLY GHGLY GHGLY (SEQ ID NO: 19)

(xviii)
GHGLY GAGFA GHGLH GFA GHGLY (SEQ ID NO: 20)

(xix)
GHGLY GAGFA GHGLH GAGFA GHGLY (SEQ ID NO: 21)

(xx)
GHGLY GHGLH GAGFA GHGLH GHGLY (SEQ ID NO: 22)

(xxi)
GHGLY GAGFA GAGFA GHGLH GHGLY (SEQ ID NO: 23)

(xxii)
GHGLY GHGLH GAGFA GAGFA GHGLY (SEQ ID NO: 24),
and (xxiii)
combinations thereof The active agent may be or include, but is not limited to, proteins, (poly)peptides, carbohydrates, nucleic acids, lipids, chemical compounds and nanoparticles. Suitable nanoparticles may be or include, but not limited to, metal nanoparticles, metal oxide nanoparticles, and combinations thereof. The nanoparticles may be magnetic nanoparticles.

In various embodiments, the active agent is a pharmaceutical or diagnostic agent. The active agent may comprise or be insulin either alone or in combination with the enzyme glucose oxidase.

In various other embodiments, the pharmaceutical or diagnostic agent comprises or is an anti-cancer agent, such as doxorubicin either alone or in combination with magnetic nanoparticles.

The composition may be a pharmaceutical or diagnostic formulation for administration to a subject. In various embodiments it can thus comprise any one or more auxiliaries, carriers and excipients that are pharmaceutically or diagnostically acceptable. In some embodiments, the composition is a liquid. The subject may be a mammal, for example a human being.

The peptide coacervate may be covalently crosslinked. The crosslinking may be achieved by use of catechol moieties, for example by a redox reaction. In one embodiment, the peptide coacervate is crosslinked with 4-methylcatechol (4-MC) and sodium periodate ($NaIO_4$).

The pH of the composition is, in various embodiments, 7.0 or higher, for example in the range of 7.4 to 9.5.

A method for the encapsulation of an active agent in a peptide coacervate may include:
(a) providing an aqueous solution of coacervate-forming peptides, wherein said peptides are derived from histidine-rich proteins; and
(b) combining the aqueous solution of coacervate-forming peptides with the active agent to induce coacervate formation.

In these methods, the pH of the aqueous solution of the coacervate-forming peptides may be below 7, for example below 6.5 or below 6.0 or even below 5.5.

In various embodiments, the active agents in the combined aqueous solution are also provided in form of an aqueous solution. Said aqueous solution may have a pH >7 and, in some embodiments, is buffered such that the combination of the aqueous solution of the active agent with the aqueous solution of the coacervate-forming peptides obtained in the combined aqueous solution has a pH >7. In various embodiments, the combination of the aqueous solution with the active agent changes the pH of the solution in which the peptide for coacervate forming is solved to greater than 7 and thus initiates coacervate formation.

In various embodiments, the concentration of the coacervate-forming peptides in the provided aqueous solution is greater than about 0.3 mg/mL and may, for example, range from about 0.3 to about 100 mg/mL.

The combined solution after coacervate formation may be an aqueous liquid two phase formulation, comprising (1) a coacervate colloidal phase comprising the peptides derived from histidine-rich proteins and the active agent; and (2) a dilute aqueous phase.

The coacervates formed may have the form of droplets having substantially spherical shape with a diameter ranging from about 0.2 to about 5 μm.

In various non-limiting embodiments of the methods, the histidine-rich proteins and peptides are as defined above for the inventive compositions.

In still another non-limiting aspect, a method for the delivery of an active agent may include:
(i) providing a composition comprising a peptide coacervate, said peptide coacervate comprising peptides derived from histidine-rich proteins, and said active agent, wherein the active agent is encapsulated in the coacervate;
(ii) releasing said active agent from the coacervates by exposing the coacervates to conditions that trigger the release of the active agent.

In various embodiments of the above methods, the conditions that trigger the release of the active agent may be or include, but not limited to, elevated temperatures, pH changes, exposure to release agents and combinations thereof.

In a still further non-limiting aspect, a method for treating or diagnosing a condition or disease in a subject in need thereof may include:

(i) administering a composition comprising a peptide coacervate, said peptide coacervate comprising peptides derived from histidine-rich proteins, and a pharmaceutical or diagnostic agent, wherein the pharmaceutical or diagnostic agent is encapsulated in the coacervate to said subject;

(ii) facilitating the release of said pharmaceutical or diagnostic agent from the coacervate by exposing the coacervate to conditions that trigger the release of the pharmaceutical or diagnostic agent.

The conditions that trigger the release of the pharmaceutical or diagnostic agent may be selected from those disclosed above for the delivery methods. The subject may be a mammal, for example a human.

In non-limiting embodiments, the subject is a human afflicted by diabetes, wherein the pharmaceutical or diagnostic agent is insulin, wherein the coacervate further comprises encapsulated glucose oxidase, and wherein release is facilitated by an increase in glucose concentration and the resulting acidification of the coacervate.

In further exemplary embodiments, the subject is a human afflicted by cancer, wherein the pharmaceutical or diagnostic agent is doxorubicin, wherein the coacervate further comprises encapsulated magnetic nanoparticles, and wherein release is facilitated by exposure of the subject to a magnetic field resulting in a temperature increase in the coacervate.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

FIGS. 5A-5B. Relative cell viability of (A) DgHBP-2 derived peptide, and (B) Insulin-loaded coacervates. Control cells were normalized at 100% (n=6, mean±S.D.).

FIG. 6. Encapsulation efficiency of different concentration of FITC-insulin by DgHBP-2 derived peptide coacervates (n=3, mean values±S.D.).

FIG. 7. Encapsulation efficiency of FITC-insulin by different concentration of DgHBP-2 derived peptide coacervates (n=3, mean values±S.D.).

FIGS. 23A-23F. Analysis of LLPS properties of DgHBP-1 N- and C-terminal variants and peptides. (A) Amino acid sequence representation of DgHBP-1 protein fragment (SEQ ID NO:29). The repetitive region (G67-G145, corresponding to G66-G144 in SEQ ID NO:1) is presented with modular repeats indicated with different black and white shades. Non-repetitive N- and C-terminal regions are marked in white. (B) C-terminal variants (V1-C(SEQ ID NO:30) containing the whole repetitive region, and V2-C truncated at position G98 (SEQ ID NO:31)). (C) N- and C-variants obtained by trypsin cleavage. (D) Synthetic peptides. The same color marking was used for all peptides shown. Full amino acid sequences of all proteins and peptides are presented in FIGS. 16 and 24A-C. Region of the DgHBP-1 sequence indicted in brackets. Variants that undergo LLPS marked with "*". (E) Phase diagrams (C: protein or peptide concentration on x-axis and pH on y-axis) at low (0.1 M) and high (1 M) salt concentrations, illustrating the conditions required to induce LLPS. As indicated in the upper-left panel (DgHBP-1), at low protein concentration only one phase is present (soluble protein). When LLPS occurs two phases co-exist, i.e protein rich phase (coacervate micro-droplets/hydrogel) and protein depleted diluted phase (the boundary between two phases are drawn as a guide for the eye). Black empty dots indicate pH and protein concentration at which optical micrographs presented in panel (F) were obtained. (F) Examples of optical micrographs taken after LLPS of all the variants and peptides described above and of DgHBP-1 (used as a control). Micrographs of V5-N, V6-N and V7-N represent hydrogels.

FIGS. 24A-24C. Sequences of DgHBP-1 protein variants. (A) V1-C and V-2C (were expressed with His-tag and TEV protease recognition site; SEQ ID NO:30 and 31). It was attempted to carry out proteolytic cleavage of the His-tag; however we could not achieve efficient cleavage since the optimum pH for the TEV protease was within the coacervation range of the variants. It was observed that the variants containing the 6×His-TEV tag underwent LLPS in the same way as full-length protein. Thus, we concluded that the tag did not have any effect on their LLPS properties. (B) Variants obtained from trypsin cleavage of the protein mutants containing extra Lys residue. The mutants were created by genetically introducing a single Lys residue into the protein sequence that served as a recognition site for trypsin cleavage. Since the wild type HBP-1 sequence completely lacks Arg and Lys, the addition of an extra Lys residue allowed introducing a single specific cleavage site that could be precisely recognized by trypsin cleaving the protein into two fragments (referred here as N- and C-terminus fragments, e.g. Vx-N and Vx-C, respectively). V3-N (SEQ ID NO:32), V4-N(SEQ ID NO:33), V5-N(SEQ ID NO:34), V6-N(SEQ ID NO:35), V7-N(SEQ ID NO:36), V3-C(SEQ ID NO:37), V4-C (SEQ ID NO:38), V5-C(SEQ ID NO:39), V6-C(SEQ ID NO:40), V7-C(SEQ ID NO:41) (C) Synthetic peptides with modular repeats GY-23 (SEQ ID NO:20); GA-25 (SEQ ID NO:42), GH-25 (SEQ ID NO:43).

FIGS. 25A-25C Recombinant DgHBP-2. (A) Amino acid sequence of the protein with indicated trypsin sites (R in bold font) and GHGxY motif (dark grey) (SEQ ID NO:2) and additional N-terminal M, (B) DgHBP-2-N- and -C-terminal fragments (SEQ ID NO:44 and 45) obtained after trypsin cleavage. (C) Optical micrographs after LLPS. Protein concentration 2 mg/mL.

FIGS. 26A-26D LLPS properties of DgHBP-1 and -2 derived peptides. (A) Sequences and their ability to undergo LLPS. GY-25-V1 (SEQ ID NO:18), GY-25-V2 (SEQ ID NO:17), GY-20 (SEQ ID NO:19), GY-15-V1 (SEQ ID NO:48), GY-15-V2 (SEQ ID NO:49), GY-10-V1 (SEQ ID NO:47), GY-10-V2 (SEQ ID NO:50), GY-10-V3 (SEQ ID NO:51), GA-5-V1 (SEQ ID NO:27), GA-5-V2 (SEQ ID NO:46). (B) Phase diagrams of the peptides that exhibited LLPS properties. (C) Sample morphology after LLPS by optical microscopy (left micrograph: gel; middle and right micrographs: micro-droplets). (D) Site-directed mutants of GY-23 peptide (SEQ ID NO:20, 52, 53) and their LLPS ability. Color marking of DgHBP-1 modular repeats is identical to the color-coding described in FIGS. 23A-F. All samples were tested in the same conditions in various pH values and salt concentrations.

FIGS. 27A-27F NMR spectra of GY-23 peptide at different pH values (cross-peak trajectories marked with dashed lines). (A)$^{1}$H-$^{15}$N-HMQC spectrum at initial conditions of pH 3.3. (B) Overlay of $^{1}$H-$^{15}$N-HMQC spectra acquired between pH 3.3 and 7 (pH 7: initiation of LLPS). (C,D) Overlay of $^{1}$H-$^{13}$C-HSQC spectra of aliphatic (C) and aromatic (D) side chains at pH 3.3 and 7. The inset shows Tyr $^{1}$H$_{\delta}$-$^{13}$C$_{\zeta}$ cross-peaks at pH 7. (E) Overlay of long-range $^{1}$H-$^{15}$N-HMQC spectra of His side chains. The resonance assignments in the protonated state (pH 3.3) are indicated. (F) Long-range $^{1}$H-$^{15}$N-HMQC spectrum at pH 7 acquired within 5 min after pH adjustment showing transient stabilization of His ε-tautomer with characteristic resonance at ca. 250 ppm marked with the arrow. In the spectrum acquired after 30 min of pH adjustment, this cross-peak was significantly attenuated (FIGS. 31A-31B). Spectra acquired at 298° K. and a peptide concentration of 1.5 mM.

FIGS. 33A-33D. Characterization of molecular interactions driving LLPS of GY-23 peptide by ssNMR. (A) Directly observed carbon spectrum of $^{13}$C-selectively Tyr 5 and Tyr 23 labeled GY-23. (B)$^{1}$H-$^{13}$C cross-polarization (CP)-based 1D carbon spectrum of $^{13}$C selectively Tyr 5 and Tyr 23 labeled GY-23. (C) DARR (100 ms mixing time). (D) HETCOR (100 µs mixing time) spectra of GY-23 (Tyr 5 and Tyr 23 labelled with $^{13}$C and $^{15}$N). Correlations indicating Tyr-Tyr interactions are marked with arrows.

FIGS. 34A-34B Correlation functions of the DLS measurements of GY-23 peptide before and after coacervation (FIG. 33C) showing the intensity correlation function, C(τ) vs. the correlation time, τ. (A) Sample before coacervation (10 mM in acetic acid, pH 3.3). The curve with a single decay at short correlation times represents a monomodal distribution of rather small particles in the nanometer range. (B) Sample after LLPS (coacervation buffer, pH 7.0). The correlation function shows two decays at higher correlation times compared to (A) indicating the presence of two distinct populations of larger particles (coacervates).

FIG. 35. List of buffers used in LLPS studies of HBP-1 protein, its variants, and HBP peptides at different pH and ionic strength. Each buffer was prepared at 0.1 M, 0.5 M, and 1 M ionic strength (adjusted with NaCl). Ionic strength defined as the sum of molar concentrations of a salt component of a buffer and NaCl.

FIGS. 41A-41D. 4-Methylcatechol (4-MC)/NaIO$_4$ crosslinked coacervates. Micrographs of Dox+MNP loaded, 4-MC/NaIO$_4$ crosslinked coacervates. (A and C) Light micrograph; (B and D) Fluorescence micrograph. (A and B) without magnetic field whereas (C and D) are with magnetic field. The co-localisation of red fluorescence and 4-MC/NaIO$_4$ coacervates indicates that Dox is still retained within the coacervates after crosslinking. Under a directional magnetic field, the 4-MC/NaIO$_4$ coacervates aligned themselves along the magnetic field and formed strings of coacervates.

FIGS. 42A-42B Release of Dox from 4-methylcatechol/NaIO$_4$ crosslinked coacervates at different temperature ((A) 20 min, (B) 16 hours). The rate of Dox release increases with increasing temperature. At 20 min crosslinking, there is ~40% leakage of Dox from coacervates over 48 hours, whereas after 16 hours of crosslinking, the leakage decreases to ~25%.

FIGS. 50A-50E. Biodistribution of cy5.5 loaded DgHBP-2 peptide coacervates in BL6 mouse. 100 µL of DgHBP-2 peptide coacervates were injected into tail vein. (A) Total radiant efficiency of the liver after injection. (B) Total radiant efficiency of other organs/tissue excluding liver. (C) Micrograph of cyc5.5 loaded coacervates. colocalization of cy5.5 within the coacervates droplets indicate that cy5.5 has been encapsulated successfully. Within 1 hour of injection, most of the coacervates were cleared by liver, kidneys and spleen. Of the three organs, liver has the highest radiant, indicating that this is the main route of excretion (A, B, C). (D) To improve the half-life biodistribution, cy5.5 loaded coacervates were coated with bovine serum albumin before injecting into BL6 mouse. There were some differences between the biodistribution of the coated and non-coated coacervates, notably the kidney, heart and aorta. (E) Merged fluorescence and light images of dissected organs from coated and non-coated coacervates injected mouse.

DETAILED DESCRIPTION

Figure 1A:
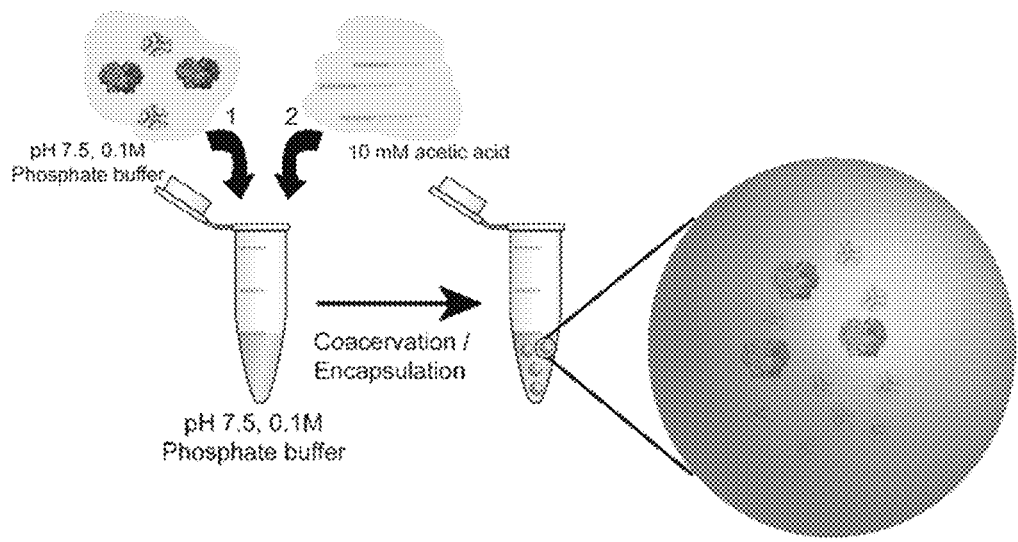
FIGS. 1A-1B. Schematic representation of the glucose-responsive insulin delivery system (GRIDS) based on DgHBP-2 derived peptide coacervates. (A) Illustration of the coacervation and encapsulation process. (B) When the coacervate droplets are exposed to glucose, the latter diffuses into the droplets and is converted into gluconic acid. This results in a local decrease of pH and in turn to the dissociation of coacervate droplets with the concomitant release of insulin.

Compositions for delivery of an active agent, such as a pharmaceutical or diagnostic agent, may include a peptide coacervate, said peptide coacervate comprising peptides derived from histidine-rich proteins, and said active agent, wherein the active agent is encapsulated in the coacervate as well as methods of manufacture thereof and methods of use thereof.

"Coacervate", as used herein, has the meaning as commonly understood in the art and discussed in the background section. Accordingly, coacervates are two-phase liquid compositions, i.e. exhibiting a liquid-liquid phase separation (LLPS), comprising or consisting of a concentrated macromolecule-rich (or coacervate) phase and a dilute macromolecule-depleted phase. The two phases of the peptide coacervates are one peptide-rich coacervate phase and one dilute peptide-depleted phase. The peptide-rich coacervate phase is also referred to herein as "peptide colloid" or "peptide coacervate droplets".

"Histidine-rich proteins", as used herein, relates to proteins that include at least one histidine residue and overall have a comparably high amount of residues of the amino acid histidine (His or H). This may mean that the histidine content of a given protein is above 3%, for example greater than 5% or greater than 10% or greater than 12%, relative to the total number of amino acids in the peptide sequence.

"Protein", as used herein, relates to polypeptides, i.e. polymers of amino acids connected by peptide bonds, including proteins that comprise multiple polypeptide chains. A polypeptide typically comprises more than 50, for example 100 amino acids or more.

"Peptide", as used herein, relates to polymers of amino acids. In various non-limiting embodiments, the peptides may include only amino acids selected from the 20 proteinogenic amino acids encoded by the genetic code, namely glycine, alanine, valine, leucine, isoleucine, phenylalanine, proline, serine, threonine, asparagine, glutamine, tyrosine, tryptophan, histidine, arginine, lysine, aspartic acid, glutamic acid, cysteine, and methionine. These amino acids are also designated herein by their three or one letter code. The peptides may be dipeptides, tripeptides or oligopeptides of at least 4 amino acids in length. Typical lengths for the peptides may range from at least about 5 amino acids to about 50 amino acids in length, for example at least 10, 12, 14, 15, 16, 17, 18, 19, 20, 21, 22, 23, 24 or 25 amino acids in length, the upper limit for example being 40, 35 or 30 amino acids.

"Encapsulate", as used herein in relation to the active agent, means that the active agent is entrapped in the peptide coacervate phase, for example the coacervate droplets formed by the peptides. Said entrapment may be such that the active agent is completely surrounded by peptides forming the coacervate phase but also includes embodiments, where the active agent is at least partially exposed on the surface of the respective coacervate phase, for example by being tethered to the colloidal phase via a certain group or moiety.

"About", as used herein in connection with a numerical value means said value±10%, for example ±5%.

In various embodiments, the composition is an aqueous liquid two phase formulation. "Aqueous", as used in this context, means that the dilute phase is mainly water, i.e. comprises at least 50 vol. % water. In various embodiments, the composition may use water as the only solvent, i.e. no additional organic solvents, such as alcohols, are present. In other embodiments, the composition is an aqueous composition that additionally contains one or more solvents other than water, with water however being the major constituent, i.e. being present in an amount of at least 50, at least 60, at least 70, at least 80, at least 90, at least 95 or 99 vol. %.

In such embodiments, the coacervate colloidal phase comprises the peptides derived from histidine-rich proteins in form of colloids encapsulating the active agent. In some embodiments, the colloidal phase has the form of droplets having a substantially spherical shape with a diameter ranging from about 0.2 to about 5 µm. The diameter of the substantially spherical shape may be the "equivalent spherical diameter (ESD)" referring to the diameter of a perfect sphere of equivalent volume as the potentially irregularly shaped droplet. For example, the droplet may have an ellipsoid shape, and the equivalent spherical diameter would then be the diameter of a perfect sphere of exactly the same volume. Each of the droplets is made up of the coacervate-forming peptides and, in various embodiments, is homogeneous in that it has no distinct core-shell morphology, but rather is a colloidal particle with no peptide gradient over its radius. In alternative or additional embodiments, the coacervate phase may take the form of a condensed hydrogel.

The dilute aqueous phase may include a water-based liquid, as described above. It is peptide-depleted in that the majority of the peptides are located in the colloidal phase, e.g. 80 wt.-% or more of the peptides are present in the colloidal phase, for example at least 85, at least 90, at least 95, at least 96, at least 97, at least 98, or at least 99 wt.-%. The dilute phase may thus contain residual amounts of peptides in the coacervate composition. As the coacervate formation is an equilibrium reaction, the exchange of peptides from the colloidal phase to the dilute phase and vice versa may be dynamic. However, in various embodiments, the above distribution applies.

In various embodiments, the histidine-rich proteins are histidine-rich beak proteins (DgHBPs), for example derived from the beak of a squid, in particular the Humboldt squid (*Dosidicus gigas*). The histidine-rich proteins may, for example, include or be, but not limited to, DgHBP-1 (SEQ ID NO:1) and DgHBP-2 (SEQ ID NO:2), with the peptides derived therefrom being, in various embodiments, fragments thereof that comprise at least one copy of the peptide motif GHGXY, wherein X is valine (V), leucine (L) or proline (P).

As used herein, "peptides derived from histidine-rich proteins" generally refers to peptides that represent fragments or variants or both of histidine-rich proteins, in particular histidine-rich proteins that naturally occur, for example in the Humboldt squid. The peptides may be produced by genetic engineering techniques as known to those skilled in the art. The peptides thus artificially produced may represent amino acid stretches of the proteins they are derived from but do not encompass the full native protein sequence. In various embodiments, the derived peptides are N- and/or C-terminally truncated fragments of the respective histidine-rich protein. In case of DgHBP-1 and DgHBP-2, the peptides may include N-terminally truncated fragments, e.g. C-terminal fragments missing at least the N-terminus. In various embodiments, these may also be C-terminally truncated such that they miss one or more amino acids from the C-terminus. In various other embodiments, the peptides are further modified in that they also lack, in addition to an N- and/or C-terminal truncation, amino acids within the sequence relative to the respective stretch in the template sequence. Alternatively or additionally, the peptides may also comprise amino acid substitutions, deletions or insertions relative to the protein sequence they are derived from.

The peptides may also be derived from histidine-rich proteins in that they comprise a sequence motif also occurring in said proteins with the rest of their sequence optionally being different from that of the histidine-rich protein they are derived from.

When reference is made to sequence differences or sequence identity, this means that in a given peptide molecule the respective amino acid at a given position is identical to the amino acid in a reference peptide/protein at the corresponding position. The level of sequence identity is given in % and can be determined by an alignment of the query sequence with the template sequence.

The determination of the identity of amino acid sequences is achieved by a sequence comparison. This comparison or alignment can, for example, be based on the BLAST algorithm well-established and known in the art (see, e.g., Altschul et al. (1990) J. Mol. Biol. 215, 403-410; and Altschul et al. (1997) Nucleic Acids Res., 25, 3389-3402) and is in principle carried out by aligning stretches of amino acids in the peptide sequences with each other.

Such a comparison allows determining the identity of two sequences and is typically expressed in % identity, i.e. the portion of identical amino acid residues in the same or corresponding positions. If not explicitly stated otherwise, the sequence identities defined herein relate to the percentage over the entire length of the respective sequence, i.e. typically the reference sequence. If the reference sequence is 20 amino acids in length, a sequence identity of 90% means that 18 amino acids in a query sequence are identical while 2 may differ. In a non-limiting embodiment, the peptides include at least the sequence having GHGXY within the peptide sequence; all other amino acids within the sequence may be changed without affecting the functionality of the peptide. X of the GHGXY sequence may be valine (V), leucine (L), or proline (P) in another non-limiting embodiment.

As the peptides include fragments and variants of histidine-rich proteins that do not occur in nature and have typically been artificially produced, the peptides are, in various embodiments, artificial peptides, such as those created by genetic engineering techniques, recombinant peptides, and the like known to those skilled in the art.

In various embodiments, the peptide has a minimum length of 16 amino acids, for example 18 or 20 amino acids, and comprises at least two sequence motifs GHGX$^1$Y, for example GHGLY, or at least one sequence motif GHGX$^1$Y, for example GHGLY (SEQ ID NO:46), and at least one sequence motif GHGLX$^4$, for example GHGLH (SEQ ID NO:28) or GHGLG (SEQ ID NO:54).

In non-limiting embodiments, the peptides may include at least two copies of the motif GHGX$^1$Y, for example GHGLY, separated by a spacer composed of the motifs (i) GX$^2$GX$^3$A, for example GAGFA (SEQ ID NO:27), (ii) GFA and/or (iii) GHGLX$^4$, for example GHGLH or GHGLG, the spacer having a minimum length of 13 amino acids, for example GX$^2$GX$^3$AGHGLX$^4$GFA. Alternatively, the peptides of may include at least four copies of the motif GHGX$^1$Y, for example GHGLY.

In various embodiments, the peptides derived from histidine-rich proteins comprise the amino acid sequence

$(GHGX^1Y)_a[(GX^2GX^3A)_b(GHGLX^4)_c(GFA)_d]_f(GHGX^1Y)_a$ wherein X$^1$ is valine (V), leucine (L) or proline (P), X$^2$ is alanine (A) or proline (P); X$^3$ is phenylalanine (F) or tyrosine (Y), X$^4$ is leucine (L), histidine (H), tyrosine (Y) or glycine (G),
each a is 0 or an integer ≥1;
each b is 0 or an integer ≥1;
each c is 0 or an integer ≥1;
each d is 0 or an integer ≥1;
f is an integer ≥1;
with the sum of all a being ≥2 and the sum of all a+b+c+d is ≥4.

In the above sequence and all further sequences disclosed below, amino acids are identified by their one letter code. Thus, G stands for glycine, H stands for histidine, L stands for leucine, Y stands for tyrosine, etc. The peptides are also shown in the conventional way, i.e. in the N- to C-terminal orientation. The individual amino acids are covalently coupled to each other by peptide bonds.

In the above peptides, the minimum sequence motif that is present is two motifs GHGX$^1$Y, for example GHGLY, with the peptide being at least 16 amino acids in length (sum of all a=2 and sum of all d=2).

The upper limit in peptide length may be 50 amino acids, for example up to 40, up to 35 or up to 30 amino acids.

Exemplary peptides encompassed by the above sequence are described below.

In addition to the above sequence motifs, the peptides may comprise additional amino acids on their N- or C-terminal end or on both, for example 1-10 or 1-5 additional amino acids. In various non-limiting embodiments, the peptides may additionally comprise a C-terminal tryptophan residue (W). In various non-limiting embodiments, the peptides may include only 1-5 additional amino acids on their termini in addition to the above sequence motifs. Alternatively, the peptides may include only one or more of the above sequence motifs in another non-limiting embodiment.

All peptides disclosed herein may be additionally modified by non-amino acid moieties, such as lipid or carbohydrate or other organic or inorganic moieties, including PEGylation, farnesylation, and the like. These modifications may impart additional desirable properties, for example increased hydrophobicity and the like.

In specific embodiments, the peptides derived from histidine-rich proteins may include an amino acid sequence, such as but not limited to:

(1)

$$(GHGXY)_n,$$

wherein X is valine (V), leucine (L) or proline (P), and n is ≥4;

(2)

$$[(GHGXY)_n (GAGFA)_m]_i \; GHGXY$$

wherein X is valine (V), leucine (L) or proline (P); n is ≥1; m is ≥1; and i≥2;

(3)

$$[(GHGXY)_n (GHGLH)_m]_i \; GHGXY$$

wherein X is valine (V), leucine (L) or proline (P); n is ≥1; m is ≥1; and i≥2;

(4)

$$(GHGXY)_n (GAGFA)_m \; GHGXY$$

wherein X is valine (V), leucine (L) or proline (P); n is ≥1; and m is ≥2; and (5)

$$(GHGXY)_n (GHGLH)_m \; GHGXY$$

wherein X is valine (V), leucine (L) or proline (P); n is ≥1; and m is ≥2;

Non-limiting peptides may include an amino acid sequence, such as but not limited to, (i)
(SEQ ID NO: 3)
GHGXY GHGXY GHGXY GHGXY GHGXY W (ii)
(SEQ ID NO: 4)
GHGXY GHGXY GHGXY GHGXY GHGXY (iii)
(SEQ ID NO: 5)
GHGXY GAGFA GHGXY GAGFA GHGXY (iv)
(SEQ ID NO: 6)
GHGXY GHGLH GHGLH GHGLH GHGXY (v)
(SEQ ID NO: 7)
GHGXY GAGFA GAGFA GAGFA GHGXY (vi)
(SEQ ID NO: 8)
GHGXY GHGXY GHGXY GHGXY (vii)
(SEQ ID NO: 9)
GHGXY GAGFA GHGLH GFA GHGXY (viii)
(SEQ ID NO: 10)
GHGXY GAGFA GHGLH GAGFA GHGXY (ix)
(SEQ ID NO: 11)
GHGXY GHGLH GAGFA GHGLH GHGXY (x)
(SEQ ID NO: 12)
GHGXY GAGFA GAGFA GHGLH GHGXY (xi)
(SEQ ID NO: 13)
GHGXY GHGLH GAGFA GAGFA GHGXY (xii)
(SEQ ID NO: 14)
GHGVY GHGVY GHGPY GHGPY GHGLY W (xiii)
(SEQ ID NO: 15)
GHGVY GHGVY GHGPY GHGPY GHGLY (xiv)
(SEQ ID NO: 16)
GHGLY GAGFA GHGLY GAGFA GHGLY (xv)
(SEQ ID NO: 17)
GHGLY GHGLH GHGLH GHGLH GHGLY (xvi)
(SEQ ID NO: 18)
GHGLY GAGFA GAGFA GAGFA GHGLY (xvii)
(SEQ ID NO: 19)
GHGLY GHGLY GHGLY GHGLY (xviii)
(SEQ ID NO: 20)
GHGLY GAGFA GHGLH GFA GHGLY (xix)
(SEQ ID NO: 21)
GHGLY GAGFA GHGLH GAGFA GHGLY (xx)
(SEQ ID NO: 22)
GHGLY GHGLH GAGFA GHGLH GHGLY -continued (xxi)
(SEQ ID NO: 23)
GHGLY GAGFA GAGFA GHGLH GHGLY (xxii)
(SEQ ID NO: 24)
GHGLY GHGLH GAGFA GAGFA GHGLY All the above peptides may comprise additional N- and/or C-terminal amino acids, in particular a C-terminal W, if not already present. Furthermore, all peptides have, in various embodiments, a maximum length of 50 amino acids, for example 40 amino acids and less.

In non-limiting embodiments, the peptides may include, consist essentially of, or consist of the amino acid sequences set forth above.

The peptides may be synthesized using any conventional method known for peptide synthesis, including chemical synthesis and recombinant production. Suitable methods are well-known to those skilled in the art and may be selected using their routine knowledge.

It has been found that the above peptides form coacervates readily, in particular under neutral conditions, i.e. pH values of 7 and higher. Stable solutions of these peptides without any distinct phase separation can be formed at low pH, for example less than 4. In various embodiments, the peptides may be prepared as stock solutions in slightly acidic solutions, such as 1-100 mM, for example about 10 mM acetic acid or other suitable weak acids.

In various embodiments, the pH of the composition is 7.0 or higher, for example ranging from about 7.4 to about 9.5. These pH values ensure that the colloidal phase remains stable.

In various embodiments, the peptide coacervate, i.e. the coacervate phase formed, can be covalently crosslinked. The crosslinking may be achieved by use of a suitable crosslinker. As the peptides disclosed herein typically comprise at least one tyrosine residue, the hydroxyl groups thereof may be used for crosslinking. Suitable crosslinking agents include, without limitation, those that comprise catechol moieties, for example and without limitation 4-methylcatechol (4-MC). In such cases, crosslinking may occur by a redox reaction between the catechol moieties and aromatic hydroxyl groups, such as the tyrosine hydroxyl groups, heteroaryl groups, such as histidine imidazole groups, and amine groups, such as lysine, arginine, asparagine or glutamine amine groups. In one specific embodiment, the peptide coacervate is crosslinked with 4-methylcatechol (4-MC) and sodium periodate ($NaIO_4$).

The active agent may, for example, be a pharmaceutical or diagnostic agent. Generally, it may be or include, but not limited to, proteins, (poly)peptides, carbohydrates, nucleic acids, lipids, chemical compounds and nanoparticles. Suitable nanoparticles include those, such as but not limited to, metal nanoparticles, metal oxide nanoparticles and combinations thereof. The nanoparticles may be magnetic nanoparticles. "Nanoparticles", as used herein, refer to particles that have dimensions, such as ESD, in the nanometer range, typically up to 500 nm, for example up to 250 or up to 100 nm. The nanoparticles may be substantially spherical in shape in a non-limiting embodiment. "Chemical compounds", as used in this context, relates in particular to small molecules, i.e. organic compounds with a molecular weight of 1000 g/mol or less, such as 750 g/mol and less. This group of compounds includes, for example, known small molecule pharmaceutical compounds, such as doxorubicin. A pharmaceutical agent from the group of (poly)peptides includes insulin and other peptide hormones.

In various embodiments, the pharmaceutical or diagnostic agent may be or include, but not limited to, RNA oligonucleotides or variants thereof, such as those used in CRISPR/Cas9 or other genome-editing systems, small molecules, antibodies or antibody-like molecules, and the like.

The pharmaceutical compound may comprise or be insulin, in particular human insulin, either alone or in combination with the enzyme glucose oxidase. The enzyme glucose oxidase naturally occurs in honey and is also produced by a variety of fungi. It catalyzes the oxidation of glucose in the C1 position and yields gluconic acid. In aqueous solutions, gluconic acid undergoes an internal esterification reaction to form gluconolactone.

In various other embodiments, the pharmaceutical agent comprises or is an anti-cancer agent, such as a cytostatic agent, for example doxorubicin. Doxorubicin may be encapsulated either alone or in combination with magnetic nanoparticles.

Generally, the active agent, such as insulin or doxorubicin, may be encapsulated alone or co-encapsulated together with a release agent that facilitates release of the active agent from the coacervate. Examples of such release agents have been disclosed above and include magnetic nanoparticles and glucose oxidase in a non-limiting embodiment. Depending on the type of release agent used, the release mechanism may differ. One type of release agents leads to an acidification of the environment of the colloidal phase, with the lowering of the pH triggering the dissolution of the coacervate phase. The acidification may be dependent on the presence of an initiator or substrate, in the case of glucose oxidase, glucose. The addition of glucose or the increase in glucose concentration may thus lead to sufficient acidification to facilitate release of the encapsulated agent, for example insulin. Other types of release agents cause heat development in the vicinity of the colloidal phase that also effects release of the encapsulated agent. Such heat development may, for example, be achieved by magnetic nanoparticles and exposure to a magnetic field.

Further release mechanisms, such as peptide degradation by use of a peptidase, may be possible and can be selected by those skilled in the art dependent on the intended use.

Generally, the release may be a burst release where essentially the total load of the active agent is released over a short time span or may be a sustained release where the release occurs over a prolonged period of time. In general, the release may occur within several minutes up to several days or weeks. The release may also be step-wise in that upon exposure to certain conditions the release starts but stops when the conditions are no longer met. It can then start again once the conditions for release are again met. Such conditions that may be varied to facilitate a step-wise or need dependent release may include, but are not limited to, glucose concentration and magnetic field exposure.

The composition may be a pharmaceutical or diagnostic formulation for administration to a subject. Such formulations may additionally comprise all the known and accepted additional components for such applications. These include auxiliaries, carriers and excipients that are pharmaceutically or diagnostically acceptable, for example various solvents, preservatives, dyes, stabilizers and the like. Such formulations may additionally comprise further active agents that are not encapsulated in the coacervate phase. In various embodiments, such compositions are liquid compositions, including gels and pastes. "Liquid", as used herein, particularly refers to compositions that are liquid under standard conditions (20° C. and 1013 mbar). In various embodiments, such liquid compositions are pourable. The compositions may be in single dose or multi dose form. Suitable forms and packaging options are well known to those skilled in the art.

The compositions can be adapted for administration to a mammalian subject, for example a human being.

For the encapsulation, an aqueous solution of the coacervate-forming peptides can be used. As described above, it is possible to dissolve the peptides in an aqueous solution if the pH is low enough. Accordingly, the peptides can be dissolved in aqueous acetic acid, for example of a concentration of 1 to 100 mM, such as 10 mM. Other acids may be equally suitable, as long as they do not hydrolyze the peptide bonds or are used in concentrations low enough to avoid hydrolysis of the peptides. In these embodiments, the pH of the aqueous solution of the coacervate-forming peptides may be below 7, for example below 6.5 or below 6.0 or below 5.5 or below 5.0 or below 4.5 or below 4.0. The pH is however, in various embodiments, higher than 0, for example 1 or higher, such as 2 or higher.

For forming the coacervate and at the same time encapsulating the active agent, the solution of the coacervate-forming peptides is combined with the active agent and coacervate formation is induced. The induction of coacervate formation is typically induced by increasing the pH of the resulting solution containing both the coacervate-forming peptides and the active agent, as well as optional additional components and auxiliaries. The pH may be increased to values of 6.0 or more, 6.5 or more, 7.0 or more, but, in various embodiments, not higher than 10.0. The pH increase may be achieved by adding an alkaline agent to the solution. In case the active agent is provided in form of an aqueous solution, too, said solution may have a pH >7 and thus effect coacervate formation. To maintain the pH in a range high enough upon combination of the two solutions, the solution of the active agent may be buffered with suitable buffering agents, such that the combined aqueous solutions of the active agent and the coacervate-forming peptides retain a pH >7.

The concentration of the coacervate-forming peptides in the aqueous solution may range from 2 to 100 mg/mL. To allow efficient coacervate formation, in various embodiments, the concentration of the coacervate-forming peptides in the aqueous solution after addition of the active agent is greater than 0.3 mg/mL.

After the coacervate has been formed, it may be an aqueous liquid two phase formulation, as described above, i.e. a composition comprising (1) a coacervate colloidal phase comprising the peptides derived from histidine-rich proteins and the active agent; and (2) a dilute aqueous phase.

The coacervates formed in the above-described processes may have the form of droplets, for example microdroplets, having a substantially spherical shape with a diameter ranging from about 0.2 to about 5 µm, or may take the form of a condensed hydrogel.

In the methods for the delivery of an active agent, such as a pharmaceutical or diagnostic agent, the provided compositions comprising a peptide coacervate may be exposed to or subjected to conditions that facilitate the release of the active agent from the coacervate phase. Said release may be facilitated by dissolution of the peptides of the coacervate phase, for example reversing the formation process by decreasing the pH, or degradation or disruption of the coacervate phase by suitable means. Some of the release mechanisms have been described above. Additional release mechanisms may include the use of surfactants or denaturing agents that disrupt the formed phases.

In various embodiments, the conditions that trigger the release of the pharmaceutical or diagnostic agent may be or include, but not be limited to, elevated temperatures, pH changes, exposure to release agents, such as enzymatic agents that degrade peptides, denaturing agents or surfactants, and combinations thereof.

Methods for treating or diagnosing a condition or disease or disorder in a subject in need thereof is also disclosed, wherein the compositions described above may be used in the treatment and/or diagnosis. Such methods of treatment also include methods where a disease, condition or disordered is managed, for example in that the symptoms or effects are alleviated. The treatment methods thus also include methods for the management of diabetes, wherein the insulin deficiency in the patient is remedied by controlled release of insulin upon certain stimuli.

In such methods, the compositions described herein and comprising a peptide coacervate and a pharmaceutical or diagnostic agent, wherein the pharmaceutical or diagnostic agent is encapsulated in the coacervate are administered to said subject. The administration may make use of any suitable administration route including oral administration or parenteral administration, for example intravenous, intramuscular, subcutaneous, epidural, intracerebral, intracerebroventricular, nasal, intraarterial, atraarticular, intracardiac, intradermal, intralesional, intraocular, intraosseous, intravitreal, intraperitoneal, intrathecal, intravaginal, transdermal, transmucosal, sublingual, buccal, and perivascular.

The administration may be systemic or localized, e.g. topically.

After administration, the release of said pharmaceutical or diagnostic agent from the coacervate may be facilitated by exposing the coacervate to conditions that trigger the release of the pharmaceutical or diagnostic agent. Said exposure may occur automatically due to conditions in the body of the patient, such as metabolic action, or may be triggered externally by applying a stimulus to the patient that leads to release of the encapsulated agents, such as exposure to a magnetic field.

The conditions that trigger the release of the pharmaceutical or diagnostic agent may generally be selected from those disclosed above for the delivery methods. The subject may be a mammal, for example a human.

In non-limiting embodiments of these methods for the treatment of a disease or disorder, the subject is a human afflicted by diabetes, wherein the pharmaceutical or diagnostic agent is insulin, wherein the coacervate further comprises encapsulated glucose oxidase, and wherein release of the glucose oxidase is facilitated by an increase in glucose concentration and the resulting acidification of the coacervate. In such embodiments, an increase in glucose concentration that may occur in the patient after consumption of food leads to increased levels of glucose permeating into the coacervate phase.

In the coacervate phase, the entrapped glucose oxidase enzyme catalyzes the oxidation of glucose to gluconic acid which leads to acidification of the microenvironment of the enzyme. As a result of the lowered pH, the coacervate phase/droplet loses its structural integrity and the release of the also encapsulated insulin is facilitated.

In further non-limiting embodiments, the subject is a human afflicted by cancer, wherein the pharmaceutical agent is doxorubicin, wherein the coacervate further comprises encapsulated magnetic nanoparticles, and wherein release is facilitated by exposure of the subject to a magnetic field resulting in a temperature increase in the coacervate. In such embodiments, the subject or a body region of the subject may be exposed to magnetic fields that lead to a temperature increase in the vicinity of the magnetic particles and as a result loss of the structural integrity of the coacervate phase that then releases the doxorubicin.

In non-limiting embodiments, the cancer may be liver cancer, colon cancer, lung cancer, prostate cancer, breast cancer, and the like.

It is understood that release facilitated by glucose is not limited to insulin release but may also be used for release of other agents. Similarly, release by exposure to magnetic fields may also be used for different agents than doxorubicin, such as other anti-cancer agents, contrast agents used for imaging methods and the like.

Additional applications of the compositions and methods will be identifiable by the person skilled in the art. The compositions and methods herein disclosed are further illustrated in the following examples, which are provided by way of illustration and are not intended to be limiting the scope of the present disclosure.

EXAMPLES

Materials and Methods
Turbidimetry for DgHBP-2 Peptide Coacervation Studies 10 mg of DgHBP-2 peptide (GL Biochem) were dissolved in 10 mM acetic acid to make 10 mg/mL of stock solution. During coacervation studies, 10 μL of stock solution were added to 90 μL of buffer to make a final peptide concentration of 1 mg/mL. Coacervation studies at different buffer conditions (pH 3.5 to 10, 0.1 to 1.0M ionic strength) was then measured at 600 nm by UV-vis spectrophotometry. Relative turbidity is calculated as[1]:

$$100-100*[10^{-A600}]$$

where A600 is the absorbance value at 600 nm wavelength.
Dynamic Light Scattering (DLS)

DLS measurements were performed on ZetaPALs (Brookhaven Instruments Corporation) equipped with a 35 mW red diode laser (640 nm wavelength). 100 μL of DgHBP-2 peptide coacervates containing 1 mg of peptide was prepared for the measurement. The scattering angle was set to be 90° and each sample was measure 5 times.
Fluorescence and Optical Microscopy In Example 1 below, microscope images were taken using an inverted microscope with 63× oil Immersion lens (Zeiss Axio observer z1). Images were processed with Zen microscope and imaging software (Zeiss, blue edition). For fluorescence imaging, 1 mg/mL of DgHBP-2 peptide was used to encapsulate 0.1 mg/mL of RITC-GOx and FITC-insulin.

In Example 2 below, phase separation behavior of protein variants and peptides was studied using a Zeiss Axio Scope A1 microscope (Carl Zeiss Pte Ltd., Germany) in the reflection mode, with differential interference contrast (DIC) filters. Images were taken with an AxioCam MRc 5 camera under the control of AxioVision software.
Labelling of Insulin and Glucose Oxidase (GOx)

Fluorescence isothiocyanate dyes (Fluorescein or Rhodamine B, (Sigma Aldrich)) were dissolved in acetone to a concentration of 3 mg/mL. 200 μL of dye solution was added slowly to 1 mg of insulin (Sigma Aldrich) dissolved in 0.1 M phosphate buffer pH 7 or GOx (Sigma Aldrich) dissolved in 0.1 M carbonate buffer pH 8.5. The reaction mixture was incubated at room temperature with constant stirring for 16 hours. During the reaction, the tubes were covered with aluminium foil to prevent photobleaching. After incubation, the reaction mixture was subjected to PD-10 gel filtration column (GE healthcare life sciences) for separating unreacted dyes from the labelled Insulin/GOx. The labelled insulin and GOx were then eluted with phosphate buffer.
Insulin and GOx Encapsulation Insulin and GOx were added to buffer solution before coacervation to their respective concentrations. DgHBP-2 peptide stock solution (10 mg/mL) was subsequently added to the buffer solution at 1:9 ratio to induce coacervation and encapsulation. The final mixture was then mixed by pipetting.
MTT Assay NIH3T3 mouse fibroblasts were used to estimate the cytotoxicity of DgHBP-2 peptide and coacervates. The fibroblasts were cultivated using Dulbecco's modified eagle medium supplemented with 10% of fetal bovine serum, 100 units/mL of penicillin and 100 μg/mL of streptomycin in a 37° C. incubator with 5% $CO_2$. 100 μL of cells with a cell density of $1\times10^4$ cells/mL were seeded onto a 96-well plate (Thermo Fisher Scientific). After 24 hours, the cell culture media was substituted with 100 μL of fresh media containing different concentration of peptide or insulin-loaded coacervates. After another 24 hours, 10 μL of MTT solution (concentration: 5 mg/mL) was added into each well. Cell culture media and the excess MTT was then removed after 4 hours of incubation. 100 μL of DMSO was subsequently added into each well to dissolve the formazan crystals. The dissolved crystals were then measured at 570 nm on a 96-well microplate reader (Infinity M200, Tecan). Relative cell viability is calculated as:

$$\frac{(A_t - A_b)}{(A_c - A_b)} * 100\%$$

where $A_t$, $A_c$, and $A_b$ represent absorbance values of wells containing tested cells, control cells and DMSO, respectively.
In Vitro Release Assay (Timepoint Assay)

50 μL of 1 mg/mL of DgHBP2-peptide coacervates were loaded with 0.1 mg/mL of FITC-insulin and/or 0.01 mg/mL of GOx. The coacervates were diluted to a final volume of 150 μL using phosphate buffer (pH 7.5, 0.1M), and placed within individual dialysis tubes (12-14 kDa cut-off, Millipore). The coacervates was then dialysed against 1 mL of phosphate buffer with/without 4 mg/mL of glucose for 48 hours (37° C., 250 rpm). The fluorescence of the dialysed buffer was measured using a fluorescence spectrophotometer (Fluorolog, HORIBA Jobin Yvon) and replaced with new buffer at different time points.
In Vitro Release Assay (Alternating Glucose Concentration Assay)

The GOx+insulin coacervates were prepared similarly as above. The coacervates was then dialysed against 1 mL of phosphate buffer with glucose for 9 hours (37° C., 250 rpm). The concentration of glucose was alternated between 1 and 4 mg/mL every 1.5 hours. The fluorescence of the dialysed buffer was then measured using a fluorescence spectrophotometer (Fluorolog, HORIBA Jobin Yvon) at every 1.5 hours.
Circular Dichroism Spectroscopy DgHBP-2 peptide and insulin were prepared at 1 mg/mL and 0.1 mg/mL respectively. Circular dichroism (CD) spectra was collected using a quartz cuvette of 0.2/0.5 mm optical pathlength. Data collection was done on AVIV 420 Circular Dichroism spectrometer with the following parameters: average of three scans per experiment between wavelength range from 190 to 250 nm, 1.0 nm wavelength steps with 1.00 nm bandwidth and 0.1 s averaging time. Each experiment was repeated for 3 times and averaged to obtain the final spectrum. The final spectrum was then smoothed and plotted using originPro9.1.

Liquid-Liquid Phase Separation

Liquid-liquid phase separation properties of protein variants and peptides at different buffer conditions were assessed using the method described in (Tan et al, Nat. Chem. Biol. 11, 488-495). Briefly, protein/peptide stock solution (10 mg/mL in 10 mM acetic acid, pH 3.3) was added to a buffer solution in a volume ratio 1:5 (protein/peptide stock:buffer). The mixture was then pipetted onto a microscopy glass slide and imaged using the optical microscope.

Solution-State NMR Spectroscopy

Sample preparation—lyophilized samples were dissolved in 10 mM acetic acid (pH 3.3) containing 10% $D_2O$ and 0.2 mM DSS prior the NMR experiments. 0.5 M NaOH was used for pH adjustment during pH titration experiments.

NMR experiments—three-dimensional BEST-TROSY HNCO, HNCA, HN(CO)CA, HNCACB, HN(CO)CACB, HN(CA)CO experiments (Solyom, Z. et al. (2013) BEST-TROSY experiments for time-efficient sequential resonance assignment of large disordered proteins. J. Biomol. NMR 55, 311-321) for DgHBP-1 protein backbone assignment were recorded on a 700 MHz Bruker Advance III NMR spectrometer equipped with 5 mm z-gradient TXI cryoprobe operating at 298 K. The spectra were acquired using non-uniform sampling (NUS) with 30% amount of sparse sampling. Processing of the NUS spectra was performed using MDDNMR program (Orekhov, V. Y. & Jaravine, V. A. (2011) Analysis of non-uniformly sampled spectra with multi-dimensional decomposition. Prog. Nucl. Magn. Reson. Spectrosc. 59, 271-292) implemented in TopSpin 3.5 (Bruker) software. Backbone assignment was carried out using CARA software. $^1H$-$^{15}N$-HMQC spectra at different pHs were acquired using SOFAST-HMQC pulse program (Schanda, P. & Brutscher, B. (2005) Very fast two-dimensional NMR spectroscopy for real-time investigation of dynamic events in proteins on the time scale of seconds. J. Am. Chem. Soc. 127, 8014-8015) on an 800 MHz Bruker Advance III NMR instrument equipped with 5 mm QCI H/P/C/N solution cryoprobe, at 298 K.

Data for GY-23 backbone assignment were collected on the 800 MHz spectrometer. The same set of BESTTROSY experiments (as for DgHBP-1 protein, expect of HN(CO)CACB) were recorded utilizing NUS with 10-30% amount of sparse sampling. Processing of the data and backbone assignment was performed as described above. Experiments during pH titration: $^1H$-$^{15}N$-HMQC, $^1H$-$^{13}C$-HSQC, and long-range $^1H$-$^{15}N$-HMQC spectra of His side chains were acquired using standard pulse programs from the TopSpin 3.5 repository on the 700 MHz spectrometer. $^{15}N$- and $^{13}C$-HSQC-NOESY with 500 ms mixing time were acquired on the 600 MHz Bruker Advance III spectrometer equipped with 5 mm z-gradient TCI cryoprobe, at 298 K.

SAXS

Example 1

Sample preparation—5.0 mg of lyophilized GY-23 peptide was dissolved in 100 µL of 10 mM acetic acid (pH 3.3). Coacervation was induced by mixing of the peptide stock with the coacervation buffer (50 mM Tris-HCl, pH 7.0 buffer, containing 1 M NaCl) in 1 to 5 volume ratio. Coacervate-rich phase was collected by centrifugation (13000 g for 5 minutes at 25° C.) and transferred into a 1.5 mm quartz capillary together with some supernatant to avoid drying. The position of the capillary was then specifically aligned to hit the coacervate-rich phase.

SAXS measurements—were performed on a Bruker Nanostar U (Bruker AXS, Karlsruhe, Germany) connected to a sealed-tube Cu anode X-ray source operating at 50 kV and 600 µA (Incoatec IµSCu, Geest-hacht, Germany). A Gabel mirror was used to convert the divergent polychromatic X-ray beam into a focused beam of monochromatic Cu Kα radiation (λ=0.154 nm). The beam size was 0.3 mm. A sample to detector distance of 1077 mm gave the q-range 0.07<q<2.9 $nm^{-1}$. The 2D SAXS patterns were acquired within 1 h using a VÅNTEC-2000 detector (Bruker AXS, Karlsruhe, Germany) with an active area of 140×140 $mm^2$ and a pixel size of 68 µm. The samples were measured in 1.5 mm quartz capillaries. The scattering curves were plotted as a function of intensity, I versus q. Scattering from the corresponding buffer was subtracted as background from all samples.

Example 2

SAXS measurements—were performed at the cSAXS beamline at PSI (Viligen, Switzerland). After mixing the peptides with coacervation buffer, the coacervates were equilibrated for at least 1 h and sealed in thin-walled quartz capillaries for SAXS measurements. An X-ray beam with a wavelength of 1.11 Å (11.2 keV) was used, with a sample to detector distance of 2152 mm providing 0.05<q<5 $nm^{-1}$, where q is the length of the scattering vector, defined by $q=4\pi/\lambda \sin(\theta/2)$, $\lambda$ being the wavelength and $\theta$ the scattering angle. The 2D SAXS patterns were acquired at 12 positions on each capillary in triplets for 1 s (36 measurements per sample) using a Pilatus 2M detector (Dectris Ltd, Baden, Switzerland; active area 254×289 $mm^2$ with a pixel size of 172×172 $\mu m^2$) and integrated into the one-dimensional scattering function I(q) after inspection for beam damage. No beam damage was observed in all investigated samples. The scattering curves were plotted as a function of intensity, I versus q. Scattering from the corresponding buffer was subtracted as background from all samples before further analysis.

SAXS Data Analysis—the p(r) was calculated from the scattered intensity I(q) using the following equation (Glatter (1977) J. Appl. Crystallogr. 10, 415-421):

$$I(q) = 4\pi \int_0^\infty p(r) \frac{\sin(qr)}{qr} dr \qquad \text{Eq. 1}$$

and gives a real space representation of the overall shape of the particles. The scattering of mass fractal like aggregates was calculated according to Mildner et al. (Meakin et al. (1986) J. Phys. D: Appl. Phys. 19 1535-1545) using SASView.

Prediction of Isoelectric Point of HBP-1 Protein

Isoelectric point (pI) of the HBP-1 protein was predicted using ProtParam tool available online.

Solid-State NMR Spectroscopy

Sample Preparation—

DgHBP-1 and GY-23 peptide coacervates were loaded directly into 1.9 mm MAS rotor by ultracentrifugation (100 k g, 30 min, 20° C.) using spiNpack (Giotto Biotech., Italy) rotor packing device.

NMR Experiments—

NMR data was collected on a 600 MHz Bruker Advance III instrument equipped with a 1.9 mm MAS probe operating in HX double resonance mode. One-dimensional (1D)$^1$H-$^{13}$C crosspolarization (CP), $^{13}$C direct-polarization (DP) and 2D $^{13}$C-$^{13}$C dipolar assisted rational resonance (DARR) experiments were performed with the MAS spinning frequency set at 18 kHz and the variable temperature set at 2° C. The actual sample temperature was 10° C. based on the external calibration with ethyleneglycol (Van Geet, A. L. (1968) Calibration of the methanol and glycol nuclear magnetic resonance thermometers with a static thermistor probe. Anal. Chem. 40, 2227-2229). Chemical shifts were referenced using the DSS scale with adamantane as a secondary standard for $^{13}$C$^{48}$ (downfield signal at 40.48 ppm) and were calculated indirectly for $^1$H. The $^1$H→$^{13}$C CP transfer was achieved by using 56 kHz $^{13}$C and 81 kHz (maximum power)$^1$H spin-lock rf fields with a 90%-100% linear ramp applied on the $^1$H channel and a contact time of 250 µs. 80 kHz SPINAL-64 $^1$H decoupling was implemented during data acquisition. The recycle delays were 1.5 s and 5 s in the 10 CP and DP experiments, respectively, and the acquisition time was 19.1 ms in both experiments. Additional parameters of the 2D $^{13}$C-$^{13}$C DARR experiment included 1.5 s recycle delay, 72115.4 Hz sweep width and 14.2 ms acquisition time in the direct dimension, 36000 Hz sweep width and 7.1 ms acquisition time in the indirect dimension and 100 ms DARR mixing time. A dipolar based 2D $^1$H-$^{13}$C heteronuclear correlation (HETCOR) experiment was conducted with 35 kHz MAS rate. The variable temperature was maintained at 15° C. corresponding to 13° C. actual sample temperature. 86 kHz $^1$H and 50 kHz (maximum power)$^{13}$C spin spinlock rf fields with a 90%-100% linear ramp applied on the $^{13}$C channel were implemented for the $^1$H→$^{13}$C and $^{13}$C→$^1$H CP transfers and the contact time was 100 µs. Suppression of water signal was achieved by implementing the MISSISSIPPI scheme without the homospoil gradient (Morcombe, C. R. & Zilm, K. W. (2003) Chemical shift referencing in MAS solid state NMR. J. Magn. Reson. 162, 479-486). Additional parameters of the 2D $^1$H-$^{13}$C HETCOR experiment included 1.5 s recycle delay, 34722.2 Hz sweep width and 11.1 ms acquisition time in the direct dimension, 35000 Hz sweep width and 7.3 ms acquisition time in the indirect dimension, 10 kHz XiX $^1$H decoupling during $^{13}$C chemical shift evolution period and 10 kHz WALTZ-16 13C decoupling during $^1$H acquisition time.

Isotope Labelling of NMR Samples $^{13}$C- and $^{15}$N-labeled HBP-1 protein was expressed in *E. coli* (BL-21 (DE3) strain). A plasmid carrying the protein gene was transformed into chemically competent cells. Bacteria were cultivated in M9 minimal medium containing $^{13}$C-glucose (2.5 g/L) and $^{15}$N-ammonium chloride (1 g/L), supplemented with biotin (1 mg/L) and thiamin (1 mg/L). Protein expression was induced with 0.5 mM IPTG (Isopropyl β-D-1-thiogalactopyranoside) when OD$_{600\ nm}$ reached 0.6. The induced bacterial culture was incubated for 8 h at 37° C. at 225 RPM and harvested by centrifugation (5000 g, 15 min, 4° C.). Cell lysis and protein purification was carried out as described previously (Tan et al. (2015) Nat. Chem. Biol. 11, 488-495; Mohammadi et al. (2018) Commun. Biol. doi:10.1038/s42003-018-0090-y).

Uniformly $^{13}$C and $^{15}$N labelled GY-23 peptide was expressed using modified gene of HBP-1-V5 protein variant. The construct was composed of the N-terminal part (M1-A112) of the HBP-1 protein, followed by a trypsin recognition site (K), the GY-23 sequence, and a stop codon. The fusion protein was expressed and purified using the same protocol as for $^{13}$C-$^{15}$N-HBP-1 protein. The GY-23 peptide was cleaved off from HBP-1(M1-A112) tag with trypsin and purified as described above.

Protein Expression and Purification

Genetic constructs encoding wild type HBP-1 and -2 proteins were obtained from DNA2.0/ATUM (USA), HBP1-V1-C and -V2-C variants were provided by Protein Production Platform (School of Biological Sciences, NTU, Singapore), HBP-1-V-3-7 were purchased from GenScript (USA). The proteins and their variants were expressed in *E. coli* and purified with reverse-phase HPLC using the protocols developed for the wild type HBP-1 and -2 proteins, described previously.

Trypsin Cleavage

The lyophilized HBP-1-V3-7 variants and HBP-2 (wild type) were dissolved in 50 mM Tris-HCl buffer (pH 8.8) to the final protein concentration of 1 mg/mL. Trypsin powder (Trypsin Gold, MS grade, Promega) was dissolved in 50 mM acetic acid to the final concentration of 1 mg/mL. Enzymatic cleavage was carried out at 37° C. for 2 h at a 1/1000 trypsin/protein volume ratio. The reaction was terminated with 1 mM (final concentration) PMSF (phenylmethylsulfonyl fluoride). Products of the enzymatic cleavage were purified with reverse-phase HPLC using a 21.2×100 mm Kromasil RP-300-C8 column (AkzoNobel, Sweden) and a linear gradient of acetonitrile containing 0.1% TFA (trifluoroacetic acid). The purity of separated N- and C-terminal variants was assessed by SDS-PAGE and their molecular weight verified by MALDI-TOF mass spectrometry using an AXIMA Performance MALDI TOF/TOF Mass Spectrometer (Shimadzu Biotech). Purified products of enzymatic cleavage were freeze-dried and re-solubilized in an appropriate buffer for further studies.

Synthetic Peptides

All unlabeled peptides were synthesized and purified by HPLC (final purity >95%) by GL Biochem Ltd (China). GY-23 peptide with $^{13}$C and $^{15}$N labelled tyrosine residues was synthesized and purified using HPLC (final purity >90%) by GenScript (USA).

Encapsulation of Dox and MNPs by Coacervates

Dox (Final concentration: 0.04 mg mL$^{-1}$) and MNPs (Final concentration: 0.008% v/v) were first added to phosphate buffer (pH 9.5 0.1M) to their final concentrations. DgHBP-2 peptide stock solution (10 mg mL$^{-1}$) was successively added to the buffer/drug mixture in a 1:9 ratio to trigger encapsulation and coacervation. Gentle pipetting was then done to mix the final mixture.

Magnetic Alignment of Coacervates

Two Nd—Fe—B permanent magnets with the following dimensions (25 mm (length)×12.5 mm (width)×12.5 mm (height)) was used to generate uniform magnetic field for alignment of coacervates. The distribution and strength of the field was measured along ±x and z axis with a gaussmeter (MG-4D, Walker scientific Inc). Magnetic field of ~200 mT was applied for the alignment of coacervates.

Crosslinking of DgHBP-2 Peptide Coacervates

DgHBP-2 peptide coacervates were first prepared as above. 5 µL of 4-MC (Stock concentration: 100 mM) was added to 50 µL of 1 mg mL$^{-1}$ DgHBP-2 peptide coacervates. The reaction mixture was then diluted to 500 µL with phosphate buffer (pH 7.5, 0.1M). 5 µL of NaIO$_4$ (Stock concentration: 300 mM) was subsequently added and the final mixture was vortex immediately for 60 s. The crosslinked coacervates were then incubated at room temperature for 4 hours. After incubation, the crosslinked coacervates were washed 3× with MilliQ water.

Lysotracker Staining of HepG2 Cells

Liver hepatocellular carcinoma cell line (HepG2) was seeded at 5×10⁴ cells per mL into 4 well Lab-Tek chambered glass slide (ThermoFisher Scientific) and incubated at 37° C. for 24 hours. After incubation, cells were washed 2× with PBS. GFP loaded coacervates with/without crosslinking were added to the cells with fresh media and incubated at 37° C. for 24 hours. The cells were washed 5× with PBS and were added with fresh media containing 5 µM Lyostracker Red DND-99 (Life Technologies). After 1 hour of incubation, the cells were washed and fixed with 4% paraformaldehyde (PFA) for 20 min at room temperature. The cells were then stained with 2 µg mL$^{-1}$ of Hoechst 33342 (Sigma Aldrich) in PBS for 15 min, and lastly with 1 µg mL$^{-1}$ of wheat germ agglutinin conjugated to Alexa Fluor 633 (WGA-633 Alexa Fluor) (ThermoFisher Scientific) for 10 mins at room temperature. The cells were imaged in a confocal laser scanning microscope (True Confocal Scanner SP8, Leica). The following excitation (Ex) and emission (Em) wavelength were used: eGFP (Ex: 448 nm, Em: 509); Lysotracker red DND 99 (Ex: 577 nm, Em: 590); Hoechst 33342 (Ex: 346 nm, Em: 460); and WGA-633 Alexa Fluor (Ex: 632 nm, Em: 590). Micrographs were processed with LAS X software and Photoshop (Adobe) software.

In Vitro Release Assay (Heat Triggered Dox Release).

50 µL of 1 mg mL$^{-1}$ of crosslinked coacervates were loaded with 0.04 mg mL$^{-1}$ of Dox. The coacervates were diluted to a final volume of 200 µL with 1×PBS and placed in a 2.0 mL Eppendorf tube. The coacervates were subsequently incubated at respective temperatures for 48 hours. The coacervates were centrifuged and the supernatant was analyzed by a fluorescence spectrophotometer [Fluorolog, HORIBA Jobin Yvon (Excitation: 470 and Emission: 550)] at different time points. The removed supernatant was replaced with new buffer at each centrifugation.

Temperature Measurement of Coacervates Under Alternating Magnetic Field (AMF)

Dox+MNPs crosslinked coacervates were placed inside the copper coils of AMF generator (Inductelec Limited) with the following magnetic field settings (375 kHz, 1 Amp). Realtime temperature readings of the coacervates under AMF were taken using fiber optic temperature sensor (Luxtron m600 Temperature Monitor).

Cumulative Release of Dox Over Time

Dox+MNPs crosslinked coacervates were heated in AMF generator (Inductelec Limited) as described above. 100 µL of coacervates were taken out of the AMF generator at respective timing, followed by centrifugation and analysis of supernatant by a fluorescence spectrophotometer [Fluorolog, HORIBA Jobin Yvon (Excitation: 470 and Emission: 550)].

Release of Dox by Multiple AMF Treatment

Dox+MNPs crosslinked coacervates were heated by multiple AMF treatments. Each AMF treatment included 20 min heating by AMF generator (Inductelec Limited) with 10 mins of cooling. 100 µL of coacervates were taken out of the AMF generator at the end of each treatment and analyzed for Dox release using fluorescence spectrophotometer [Fluorolog, HORIBA Jobin Yvon (Excitation: 470 and Emission: 550)].

Figure 1B:
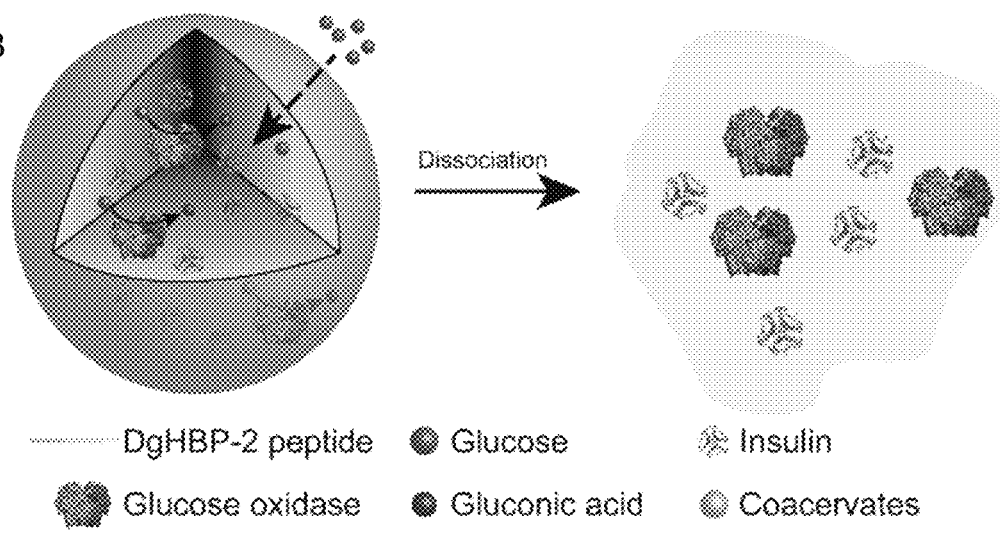

Example 1: Glucose-Responsive Peptide Coacervates with High Encapsulation Efficiency for Controlled Release of Insulin In this design, the coacervate droplets act as an insulin reservoir whereas GOx triggers the release of insulin upon exposure to glucose, based on the conversion of glucose to gluconic acid that dissociates the pH-sensitive coacervate droplets and thereby release the insulin cargo (FIGS. 1A-1B).

Figure 2B:
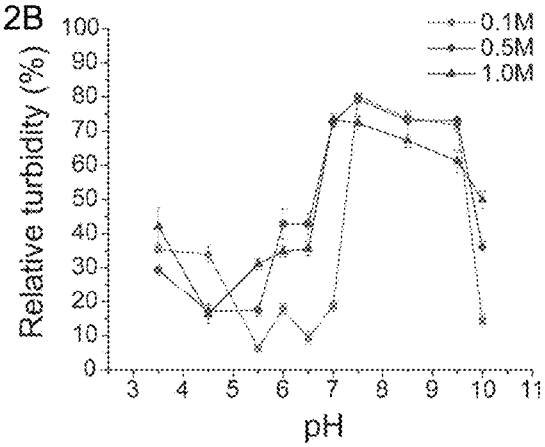
FIGS. 2A-2B. Coacervation of DgHBP-2 peptide. (A) Sequence of DgHBP-2 derived peptide (SEQ ID NO:14). (B) Relative turbidity of DgHBP-2 derived peptide at different pH and Ionic strength (n=3, mean values±S.D.). (C) Microscopy image of DgHBP-2 derived peptide coacervates at pH 7.5, 0.1 M ionic strength.
Figure 2C:
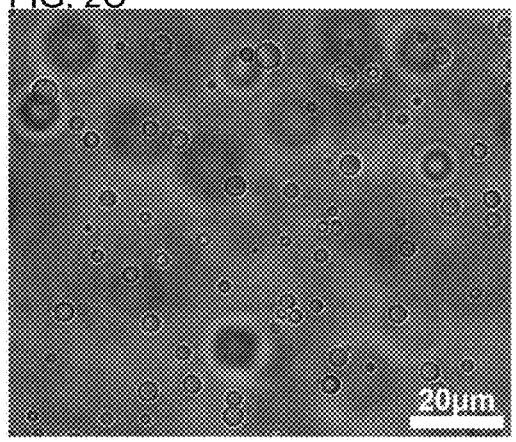
Figure 3A:
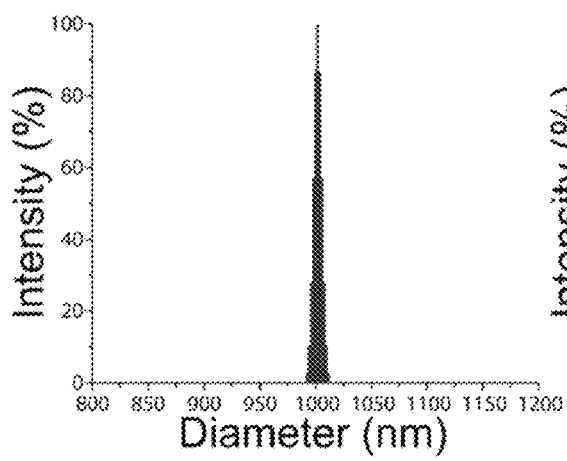
FIGS. 3A-3B. Dynamic light scattering of (A) DgHBP-2 derived peptide coacervates and (B) GOx+insulin loaded coacervates in phosphate buffer. A slight increase in hydrodynamic radius of ~6% (from 1000 to 1060 nm) was observed after encapsulation.
Figure 3B:
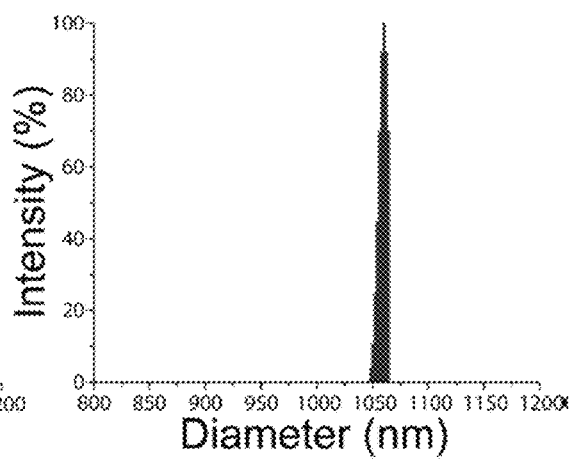

A twenty-six amino acid long consensus peptide was used derived from DgHBP-2 (DgHBP-2 peptide) that includes five GHGXY repeats with a C-terminus tryptophan residue (FIG. 2A). To prepare DgHBP-2 peptide coacervates, buffers of different pH and ionic strength were tested to determine the optimal conditions for coacervation, which was inferred by turbidimetry. Optimal coacervation occurred between neutral (pH 7.4) to slightly alkaline pH (pH 9.5) (FIG. 2B) and the formation of coacervates was confirmed by the presence of liquid-like droplets that could be clearly observed by optical microscopy (FIG. 2C). Surprisingly, even though ionic strength is usually a key factor governing coacervation (Perry et al. (2014) Polymers 6 (6), 1756; Wang et al. (1999) Macromolecules 32 (21), 7128-7134; Joshi et al. (2018) Food Hydrocolloids 74 (Supplement C), 132-138), further increase in ionic strength did not greatly affect DgHBP-2 peptide coacervation. Since DgHBP-2 peptide coacervation did not occur in acidic pH, it was reasoned that the coacervates may serve as a pH-responsive carrier whose release of therapeutic cargo could be triggered by local changes of pH. Through dynamic light scattering (DLS) measurements (FIG. 3A), the average size of DgHBP-2 peptide coacervates was ca. 1 µm and increased by 6% to ca. 1.06 µm after insulin encapsulation (FIG. 3B).

Figure 4:
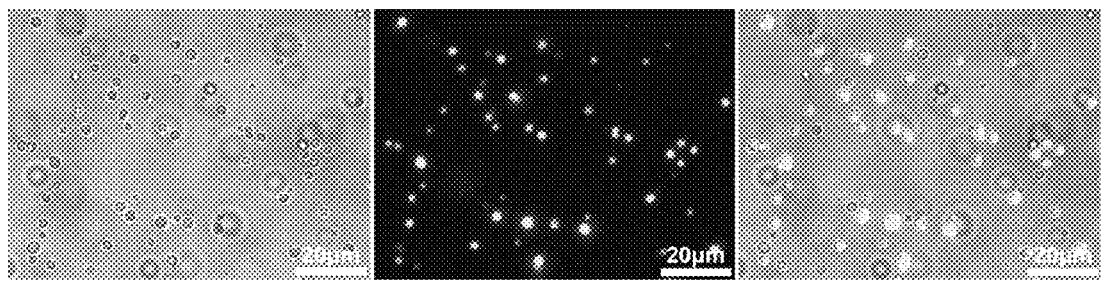
FIG. 4. Microscopy images of DgHBP-2 derived peptide coacervates (1 mg/mL) loaded with FITC-insulin (0.1 mg/mL). Light microscopy image (left); fluorescence image (middle); merged microscopy image (right). The grey droplets and green fluorescence are DgHBP-2 derived peptide coacervates and FITC-insulin, respectively.
Figure 8A:
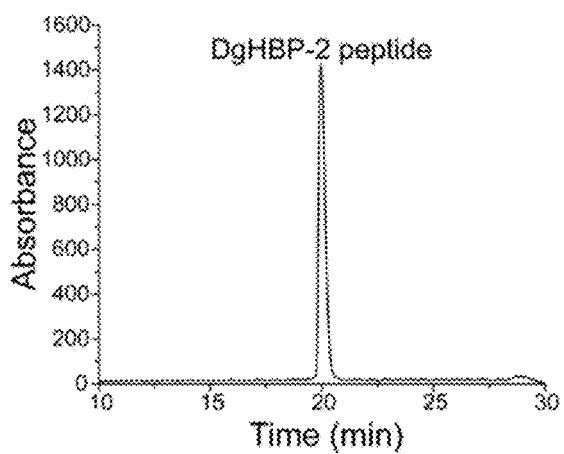
FIGS. 8A-8D RP-HPLC absorbance chromatograms of (A) DgHBP-2 derived peptide (1 mg/mL); (B) native insulin (0.1 mg/mL); (C) supernatant after coacervation; and (D) dissolved coacervates pellet after encapsulation. Black arrow indicates the retention time for native insulin. After encapsulation, almost no insulin was detected in the supernatant, whereas by dissolving the coacervates after encapsulation, insulin was found within the coacervates. These data confirm the high encapsulation efficiency of insulin within the coacervates as measured for FITC-labeled insulin by fluorescence microscopy (FIG. 9A).
Figure 8B:
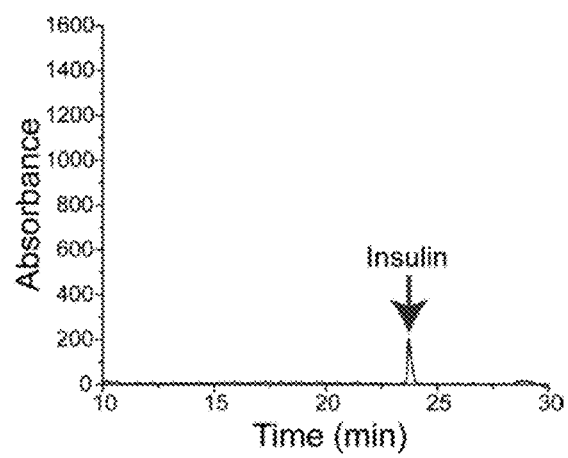
Figure 8C:
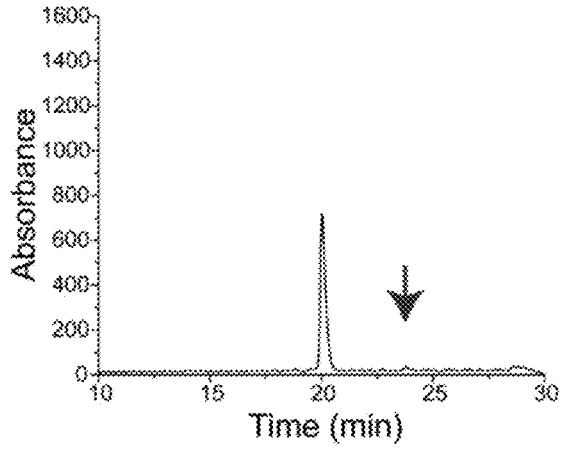
Figure 8D:
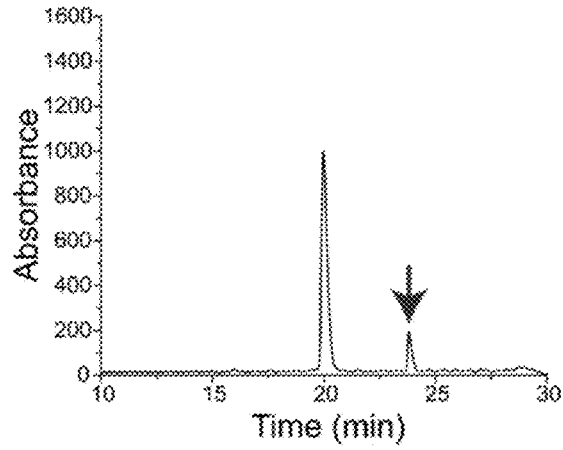

Next, it was elected encapsulating insulin within the coacervate droplets by adding insulin to the phosphate buffer solution. To verify encapsulation, insulin was labelled with fluorescein isothiocyanate (FITC) to obtain FITC-labelled insulin (FITC-insulin). Following coacervation FITC-insulin-loaded coacervates were imaged under an inverted fluorescence microscope. As shown in FIG. 4, the coacervates and green fluorescence completely overlapped with each other, demonstrating successful encapsulation of insulin by coacervates, with nearly 100% efficiency. Also the cytotoxicity of DgHBP-2 peptide in solution and in the coacervate state on mouse fibroblasts was verified using a live/dead cell assay. As shown in FIGS. 5A-B, the cytotoxicity of DgHBP-2 peptide and insulin-loaded coacervates was negligible at the tested concentrations (FIGS. 5A-B). The encapsulation efficiency (EE) was measured at different insulin/peptide ratios. At 1 mg/mL of peptide, a very high EE was found, reaching nearly 100% regardless of FITC-insulin concentration (from 0.01 to 0.4 mg/mL) (FIG. 6). The EE slightly dropped only when DgHBP-2 peptide concentration was below 0.3 mg/mL (FIG. 7). These results demonstrate the very high loading capacity of DgHBP-2 peptide coacervates, which corroborates previous studies conducted with other types of coacervates (Johnson, N. R., and Wang, Y. (2014) Coacervate delivery systems for proteins and small molecule drugs. Expert Opin. Drug Delivery 11 (12), 1829-32). This high EE was further confirmed for labeled-free insulin using reverse phase high performance liquid chromatography, where native insulin was detected only in the coacervates pellet but not in supernatant (FIGS. 8A-D), thus verifying that insulin encapsulation occurs regardless of FITC functionalization. The underlying mechanism behind the very high EE of insulin within the coacervate microdroplets is still unclear. Nonspecific interactions between DgHBP-2 peptide and insulin are likely involved, notably hydrophobic and π-π interactions given the high content of hydrophobic and Tyr residues in DgHBP-2 peptide.

Figure 9A:
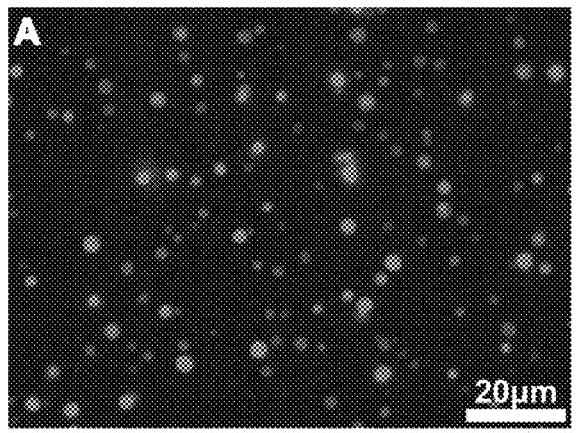
FIGS. 9A-9D. Microscopy images of DgHBP-2 derived peptide coacervates (1 mg/mL) loaded with FITC-insulin (0.1 mg/mL) and RITC-GOx (0.1 mg/mL). (A) Green fluorescence micrograph; (B) red fluorescence micrograph; (C) light microscopy micrograph; (D) merged (green, red, and light) micrograph image. Yellow fluorescence of the droplets indicate co-encapsulation of FITC-insulin and RITC-GOx.
Figure 9B:
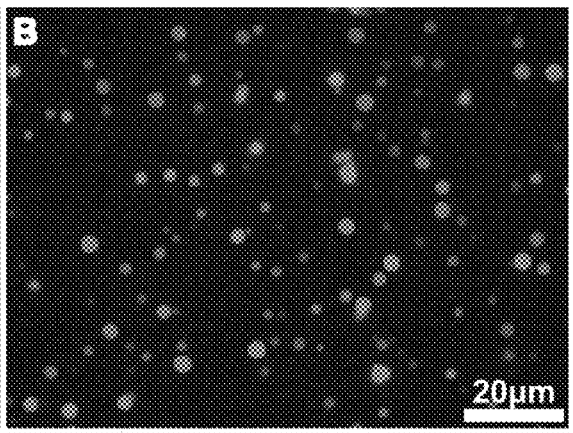
Figure 9C:
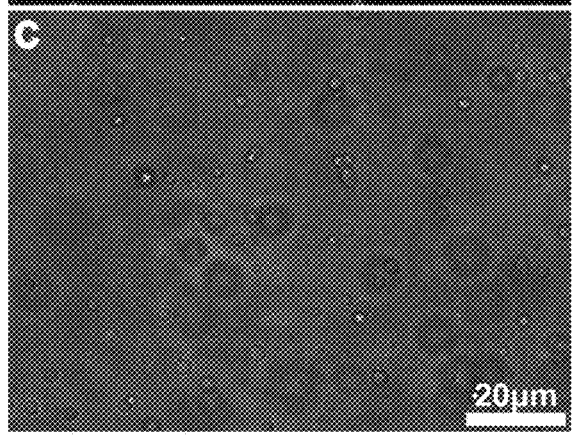
Figure 9D:
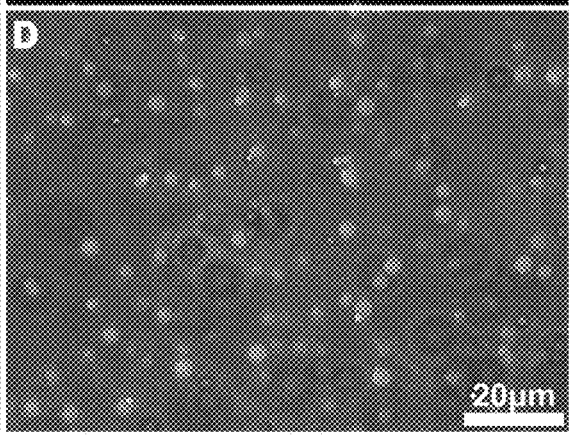

Next, it was tested whether GOx could be co-encapsulated with insulin inside the coacervate droplets. As shown in FIGS. 9A-D, the green fluorescence and the red fluorescence representing FITC-insulin and rhodamine B isothiocyanate-labelled GOx (RITC-Gox), respectively, fully overlapped and yielded yellow fluorescence (FIGS. 9A and B). These results established that both insulin and GOx could be co-encapsulated by DgHBP-2 peptide coacervates with a high efficiency (FIG. 9D).

Figure 10A:
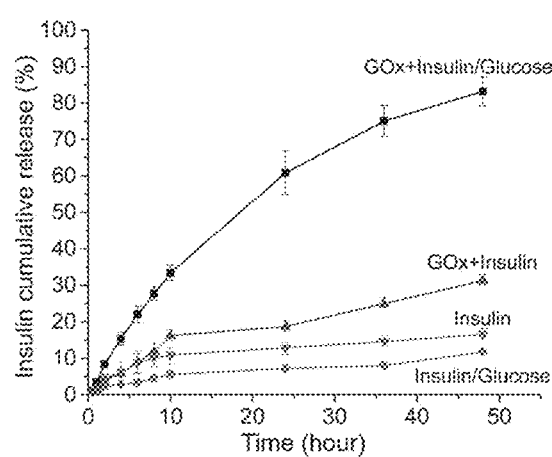
FIGS. 10A-10B In vitro release assay of insulin from coacervates (A) GOx+Insulin with 4 mg/mL of glucose (square, black); GOx+Insulin (triangle, blue); Insulin (inverted triangle, pink) and Insulin with 4 mg/mL of glucose (circle, red). (B) Alternate high glucose (4 mg/mL, blue) and low glucose (1 mg/mL, green) solution (n=3, mean values±S.D.).

To investigate whether insulin release could be triggered from the coacervates by glucose-sensing, $GO_X$+insulin-co-loaded coacervates (1 mg/mL of DgHBP-2 peptide, 0.01 mg/mL of GOx and 0.1 mg/mL of insulin) as well as insulin-loaded (1 mg/mL of DgHBP-2 peptide, 0.1 mg/mL of insulin) coacervates (free of Gox) in phosphate buffer were prepared and the coacervate droplets were exposed to glucose. As shown in FIG. 10A, the insulin release rate was much faster in the presence of both GOx and glucose (FIG. 10A), indicating that glucose readily diffused into the coacervates and converted to gluconic acid by GOx, resulting in local acidification that dissociated the coacervates.

Although some leakage of insulin was observed in the absence of glucose, the rate and the degree of insulin release over 48 hours were substantially higher in the presence of glucose.

Figure 10B:
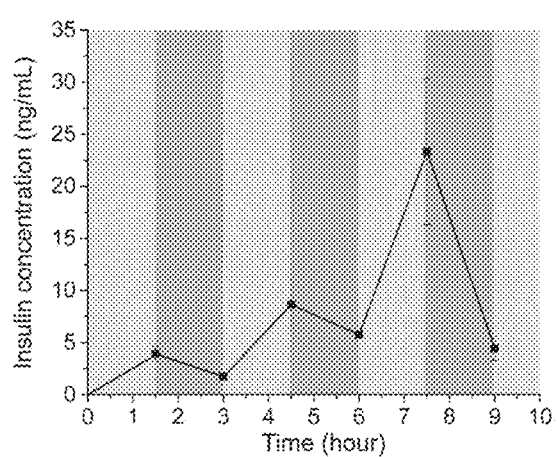

Next, the ability of GOx+insulin coacervates was examined to respond to changes in glucose concentration. The coacervates displayed a pulsatile release of insulin when the glucose concentration was altered between normal (1 mg/mL) and hyperglycemic levels (4 mg/mL) every 1.5 hours (FIG. 10B). The coacervates could reversibly vary the rate of insulin release between higher and slower rates in response to hyperglycemic and normal levels. Such a glucose-triggered insulin release behavior could be repeated for at least 3 cycles.

Figure 11A:
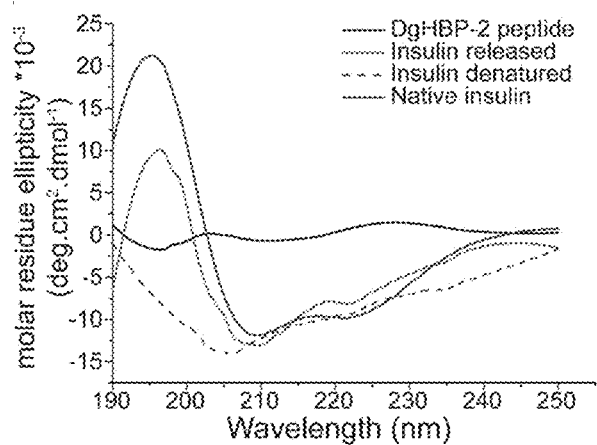
FIGS. 11A-11B. Comparison of released insulin from dissociated coacervates and native insulin. (A) CD spectra of regular insulin, denatured insulin, insulin released from dissociated coacervates, and DgHBP-2 peptide. (B) Enzyme-linked immunosorbent assay (ELISA) of regular insulin and insulin released from dissociated coacervates.
Figure 11B:
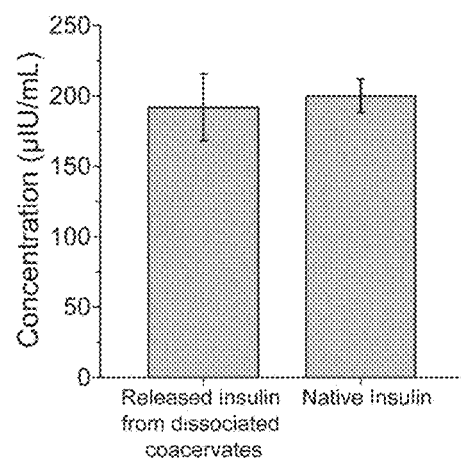
Figure 12:
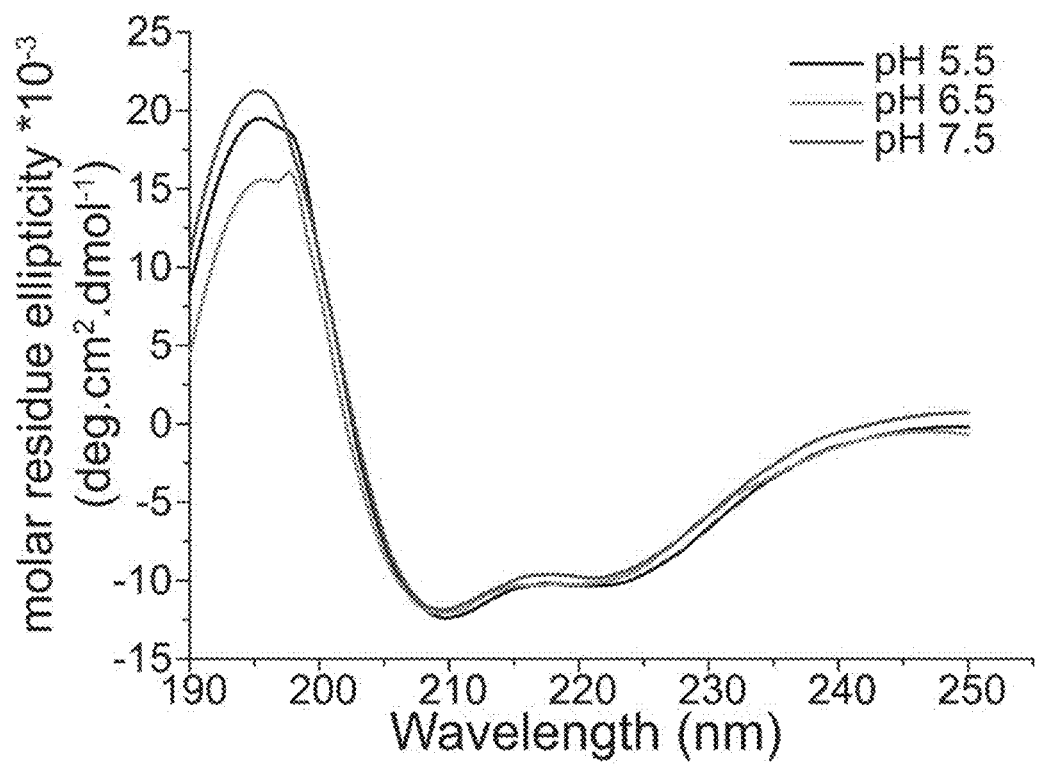
FIG. 12. Circular dichroism spectra of native insulin at different pH (n=3).

An important parameter to ensure that this GRIDS system could be used for glucose management is to verify retention of insulin activity following entrapment within the coacervate droplets (Blocher et al. (2017) Wiley Interdiscip. Rev. Nanomed. Nanobiotechnol. 9 (4), e1442) and subsequent release from the local acidic microenvironment. First, Circular Dichroism (CD) measurements were used to assess possible changes in secondary structure (FIG. 11A). CD spectra of the regular insulin solution displayed the classical α-helical signature (two minima at 208 and 222 nm). After coacervation and release, the CD signature was a mix of insulin and DgHBP-2 peptide, with the slight decrease in intensity attributed to the weaker ellipticity of the peptide. However, the characteristic minima of α-helices at 208 and 222 nm were still visible. In addition, CD spectra of native insulin at pH 5.5 to 7.5 (FIG. 12) indicated that the secondary structure was not disrupted at mild acidic conditions, strongly suggesting that released insulin retained its bioactivity. The CD spectrum of thermally denatured insulin was also measured (FIG. 11A), which exhibited important differences with native/released insulin, specifically the loss of the 195 nm maximum and of the 222 nm minimum, as well as a peak shift of the 208 nm minimum towards lower wavelength. To further verify insulin activity, the insulin-DgHBP-2 peptide solution was subjected after release to an ELISA assay. The released insulin was detected to similar levels compared to native insulin (FIG. 11B), suggesting that the conformational epitope was not disrupted since antibodies could equally recognize the coacervates-released insulin. Together, these data are in agreement with recent studies showing that therapeutic biomacromolecules retain or even exhibit enhanced bioactivity inside the coacervate phase (Blocher et al. (2017) Wiley Interdiscip. Rev. Nanomed. Nanobiotechnol. 9 (4), e1442; Black (2014) ACS Macro. Lett. 3 (10), 1088-1091; Martin et al. (2016) Langmuir 32 (23), 5881-9; Pippa et al. (2015) Int. J. Pharm. 491 (1-2), 136-43), and that folded proteins may be sequestrated within coacervate microdroplets when compared to their unfolded state (Martin et al. (2016) Langmuir 32 (23), 5881-9).

In summary, a simple and efficient GRIDS based on biomimetic peptide coacervates loaded with GOx and insulin was synthesized. The GRIDS can be easily prepared by simply mixing biomimetic DgHBP-2 peptide into aqueous buffer solutions containing insulin and GOx. Coacervation ensues and acts as an insulin reservoir with very high encapsulation efficiency. Under hyperglycemic conditions, glucose molecules diffuse into the coacervates where GOx readily converts glucose into gluconic acid, resulting in a local acidic environment that triggers the dissociation of coacervates and eventually leads to glucose-triggered release of insulin, with a release kinetics that can be altered in response to glucose levels. Furthermore, the secondary structure and the activity of insulin are retained following exposure to acidic microenvironment, which can primarily be attributed to the use of aqueous solvents. Our results indicate that this new GRIDS combine the advantages of both glucose responsiveness and high loading capacity, representing a promising potential for diabetes management. Further optimization to enhance coacervate stability is currently underway, notably to prevent premature leakage in the absence of glucose exposure, which may be achieved by introducing simple mutations in the peptide sequence or by varying the number of tandem pentapeptides.

Encapsulation of Other Therapeutics Agents in DgHBP-2 Peptide Coacervates

Figure 13:
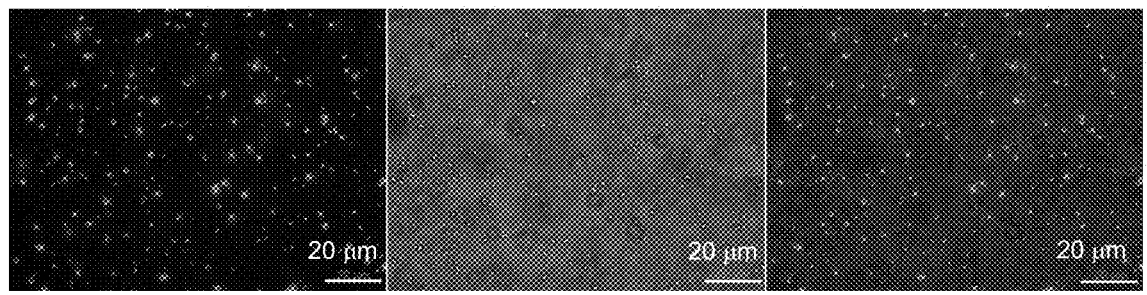
FIG. 13. Microscopy images of DgHBP-2 derived peptide coacervates (1 mg/mL) loaded with BSA-FITC (0.1 mg/mL). Fluorescence image (left); light microscopy image (middle); merged microscopy image (right).
Figure 14:
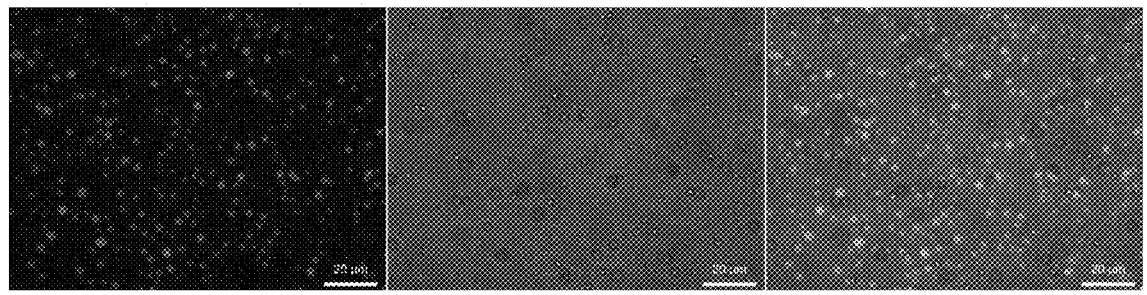
FIG. 14. Microscopy images of DgHBP-2 derived peptide coacervates (1 mg/mL) loaded with GFP (0.1 mg/mL). Fluorescence image (left); light microscopy image (middle); merged microscopy image (right).

Other than insulin and GOx, DgHBP-2 peptide coacervates can encapsulate a wide range of therapeutic or functional biomacromolecules. For example, it can efficiently encapsulate proteins such as Bovine Serum Albumin (BSA) and Green fluorescence protein (GFP) (FIGS. 13 and 14).

Figure 15:
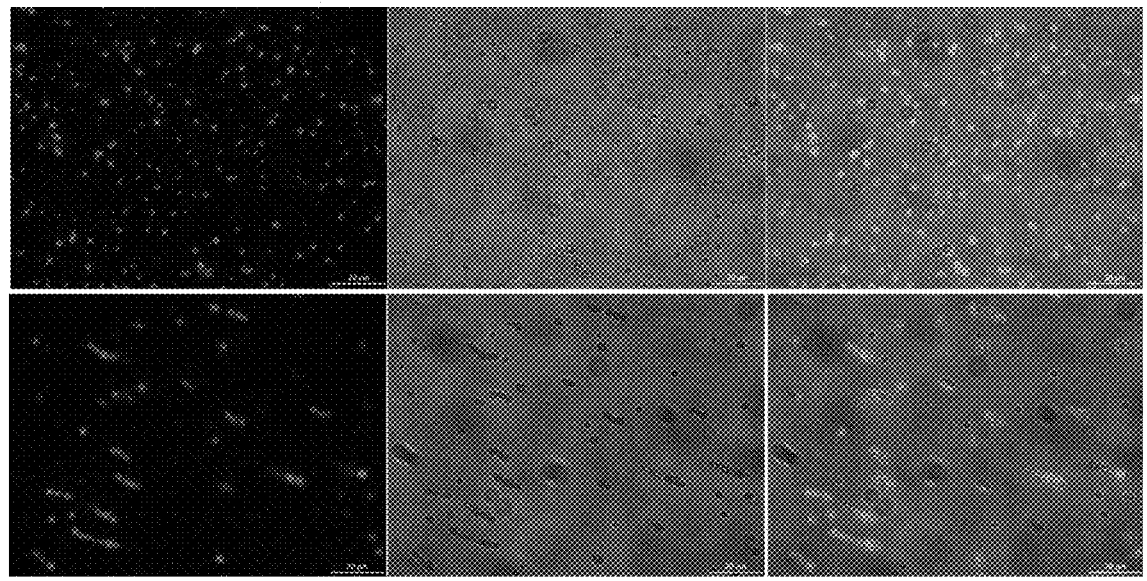
FIG. 15. Microscopy images of DgHBP-2 derived peptide coacervates (1 mg/mL) loaded with DOX (0.04 mg/mL) and MNP (0.002%). Top panel: without magnetic field and bottom panel: with magnetic field. Aligned features on the images indicate that MNPs are encapsulated within the droplets. Fluorescence image (left); light microscopy image (middle); merged microscopy image (right).

In addition, DgHBP-2 peptide coacervates can also be loaded with magnetic nanoparticles (MNP) as well as low molecular weight drugs like Doxorubicin (DOX) (FIG. 15). These DOX+MNP loaded coacervates can be manipulated using magnetic fields, opening up the possibility of magnetic targeting and magnetic field induced drug release for chemotherapy (see also Example 3).

Family of DgHBP-2 with Coacervation Capability

The ability to self-coacervate is not limited to the peptide described above, but can be expanded to a family of Dg-HBP peptides sharing common sequence design and motifs. In a non-limiting embodiment, stimuli-responsive coacervates for therapeutics release may also be achieved with the following family of peptides:

Sub-family 1:
$(GHGXY)_n$ where X can be V, L, or P, and n is the number of repeats, with is n≥4.

Sub-family 2:
$[(GHGXY)_n (GAGFA)_m]_i GHGXY$ where X can be V, L, or P, n is the number of repeats of sub-peptide 1 GHGXY (with n≥1); m is the number of repeats of sub-peptide 2 GAGFA (with m≥1), and i≥2.

Sub-family 3:
[(GHGXY)$_n$ (GHGLH)$_m$]$_i$ GHGXY where X can be V, L, or P, n is the number of repeats of sub-peptide 1 GHGXY (with n≥1); m is the number of repeats of sub-peptide 2 GHGLH (with m≥1), and i≥2.

Examples for each sub-family that have been successfully tested for self-coacervation (using turbidity measurements and observation of droplets by optical microscopy) include the following:

```
For sub-family 1:
                                    (SEQ ID NO: 15)
GHGVY GHGVY GHGPY GHGPY GHGLY For sub-family 2:
                                    (SEQ ID NO: 16)
GHGLY GAGFA GHGLY GAGFA GHGLY For sub-family 3:
                                    (SEQ ID NO: 17)
GHGLY GHGLH GHGLH GHGLH GHGLY
```

Example 2: Aromatic Interactions within Repeat Motifs Trigger pH-Responsive Liquid-Liquid Phase Separation of Intrinsically Disordered Peptides Mutagenesis studies with both solution- and solid-state NMR spectroscopy were combined to investigate the coacervation process of DgHBP-1. A central characteristic of DgHBPs is the presence of repetitive regions in their C-termini that share similarity with the hydrophobic repeats of tropoelastin (Cai et al. (2017) Soft Matter 13, 7740-7752). Thus, DgHBP-1 was selected as a model structural IDP to shed light on sequence motifs that govern LLPS as well as on intermolecular interactions stabilizing the coacervate phase. The DgHBP-1 sequence was systematically explored and it was identified that the motif repeat GHGLY drives LLPS. It was demonstrated that at least two copies of such repeats and a linker sequence must be included, or alternatively at least four tandem repeats must be present in order to trigger coacervation. Within this motif it was shown that His residues serve as a molecular switch: upon pH change, they first undergo deprotonation followed by hydrogen bonding with Tyr. Finally, using solution-, solid-state NMR, and Small Angle X-ray Scattering (SAXS) it was demonstrated that clustering of Tyr residues is critical to stabilize coacervate micro-droplets.

DgHBP-1 is Structurally Disordered in Solution

Figure 16:
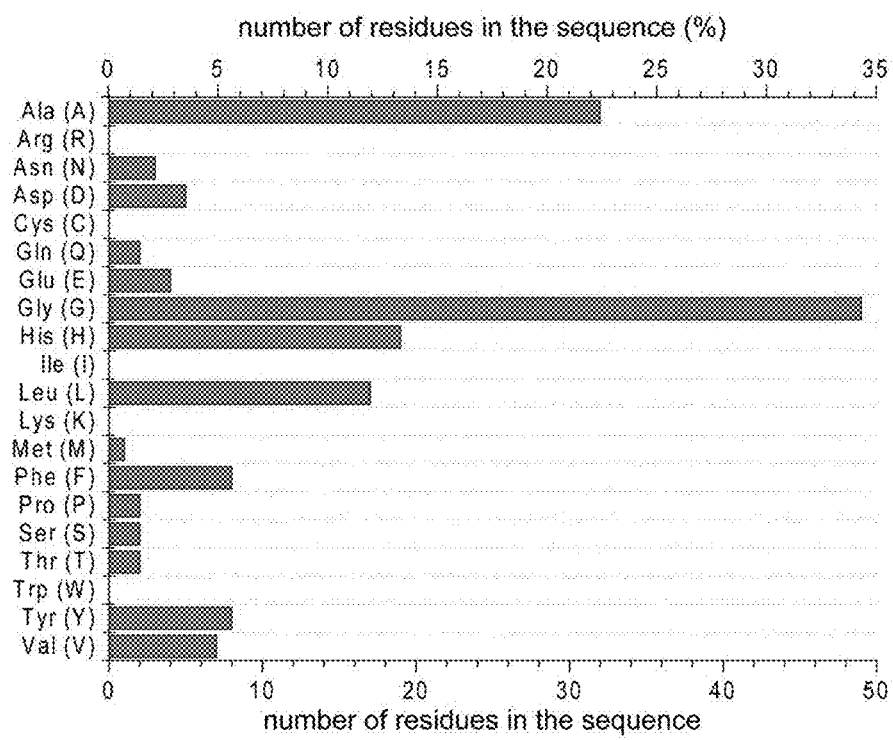
FIG. 16. Recombinant DgHBP-1—amino acid sequence (SEQ ID NO:1 with additional N-terminal M) and composition. DgHBP-1 possesses sequence features characteristic for IDP exhibiting LLPS properties. It has low sequence complexity that lacks Cys, Ile, Lys, and Met (added as a starting amino acid in recombinant form of the protein), Arg, and Trp residues. The N-terminus contains negatively-charged residues (Glu, Asp) distributed along His-rich and Ala-rich clusters. The C-terminus lacks acidic residues and contains region of hydrophobic modular penta-repeats (marked in shades of blue and red) that are enriched mainly with Ala, Gly, His, Leu, Phe and Tyr residues.
Figure 17A:
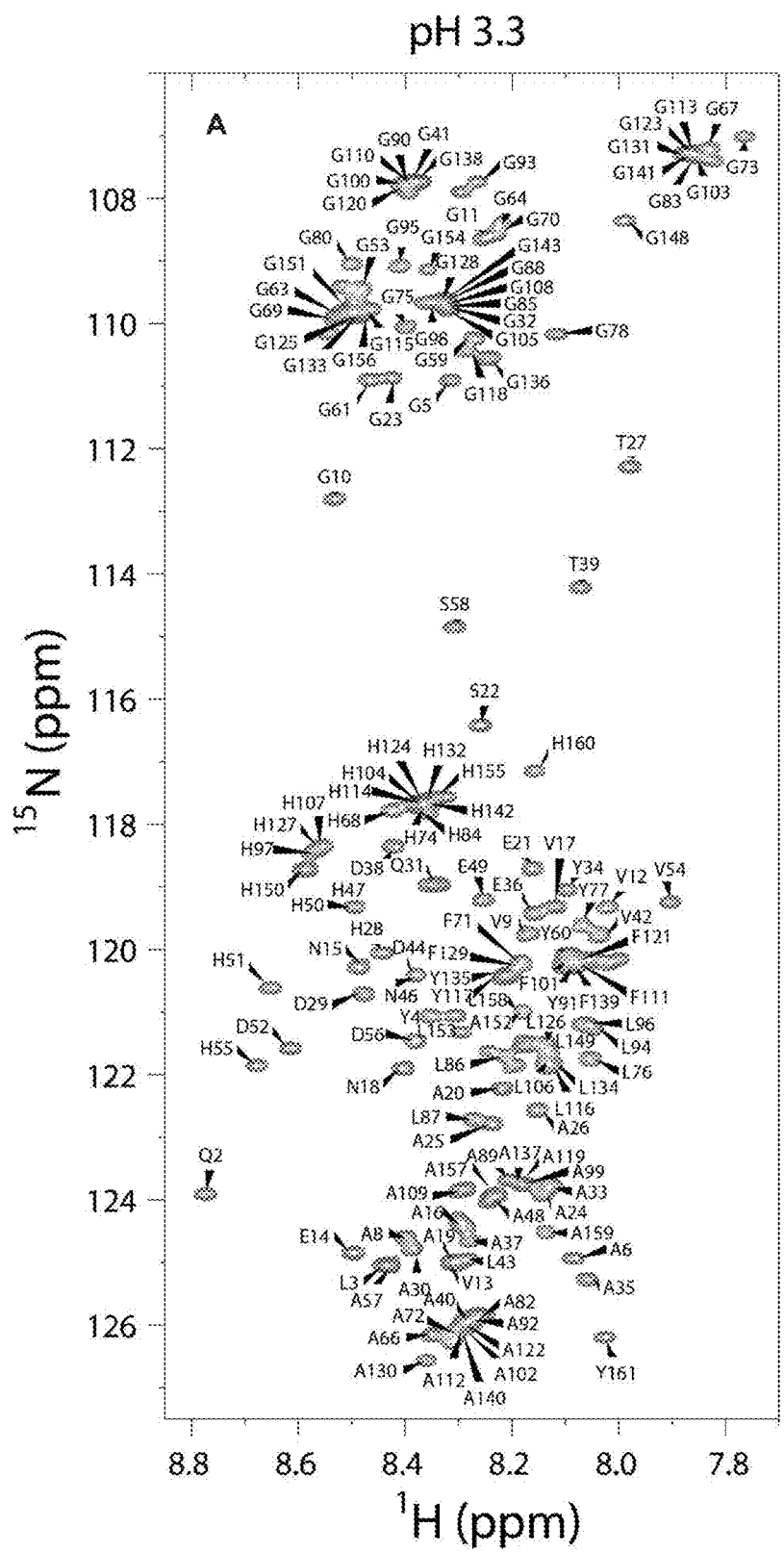
FIGS. 17A-17C. $^{1}$H-$^{15}$N-HSQC spectra of DgHBP-1 at different pH values. (A) DgHBP-1 in the initial solution state at pH 3.3. (B) Dilute phase after LLPS at pH 6.5 (after sedimentation of coacervate micro-droplets). (C) Overlay of the two spectra. Spectra acquired at 298° K. and a protein concentration of 2 mg/ml (130 µM).
Figure 18:
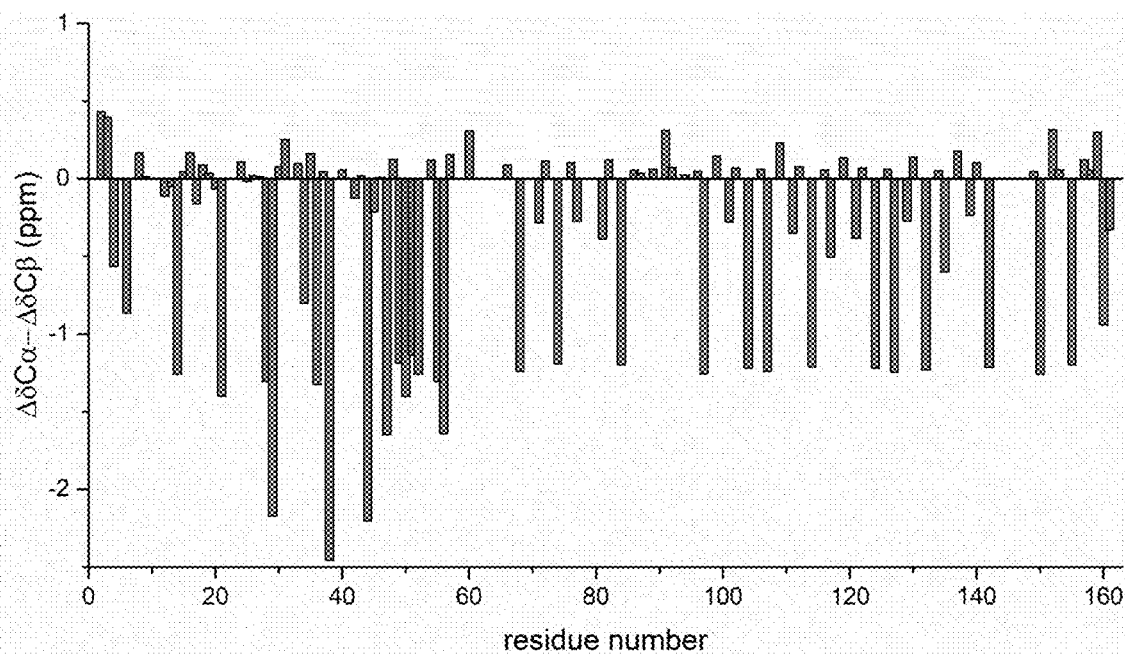
FIG. 18. Residue-specific secondary structure propensity of DgHBP-1. Secondary shifts ($\Delta\delta C_{\alpha}$-$\Delta\delta C_{\beta}$) indicate lack of secondary structure formation.

DgHBP-1 possesses primary structure features characteristic of IDPs with LLPS properties (FIG. 16). In a recent study, it was shown using Circular Dichroism (CD) and SAXS that it has a dynamic, disordered molecular structure in solution that transitions to a more ordered form in the coacervate state, and it was proposed that hydrophobic modular penta-repeats from the C-terminus are key to the coacervation process (Cai et al. (2017) Soft Matter 13, 7740-7752). To verify these assumptions and investigate the structural features of the protein, a standard set of double- and triple-resonance NMR experiments with soluble recombinant DgHBP-1 was carried out. As predicted, NMR results indicated that the protein lacked a defined three-dimensional structure in solution: the $^1$H-$^{15}$N heteronuclear single quantum coherence (HSQC) spectrum (FIG. 17A) showed narrow distribution of the amide proton chemical shifts, which is typically observed for IDPs with LLPS properties (Conicella et al. (2016) Structure 24, 1537-1549; Brady et al. (2017) Proc. Natl. Acad. Sci. 201706197. doi:10.1073/pnas.1706197114; Burke et al. (2015) Mol. Cell 60, 231-241). Analysis of Cα and Cβ chemical shifts of assigned residues did not show significant deviations from random coil values, validating that the monomeric DgHBPs are uniformly disordered (FIG. 18).

Residues Located at C-Terminus of DgHBPs are Involved in the pH Dependent LLPS

Figure 17B:
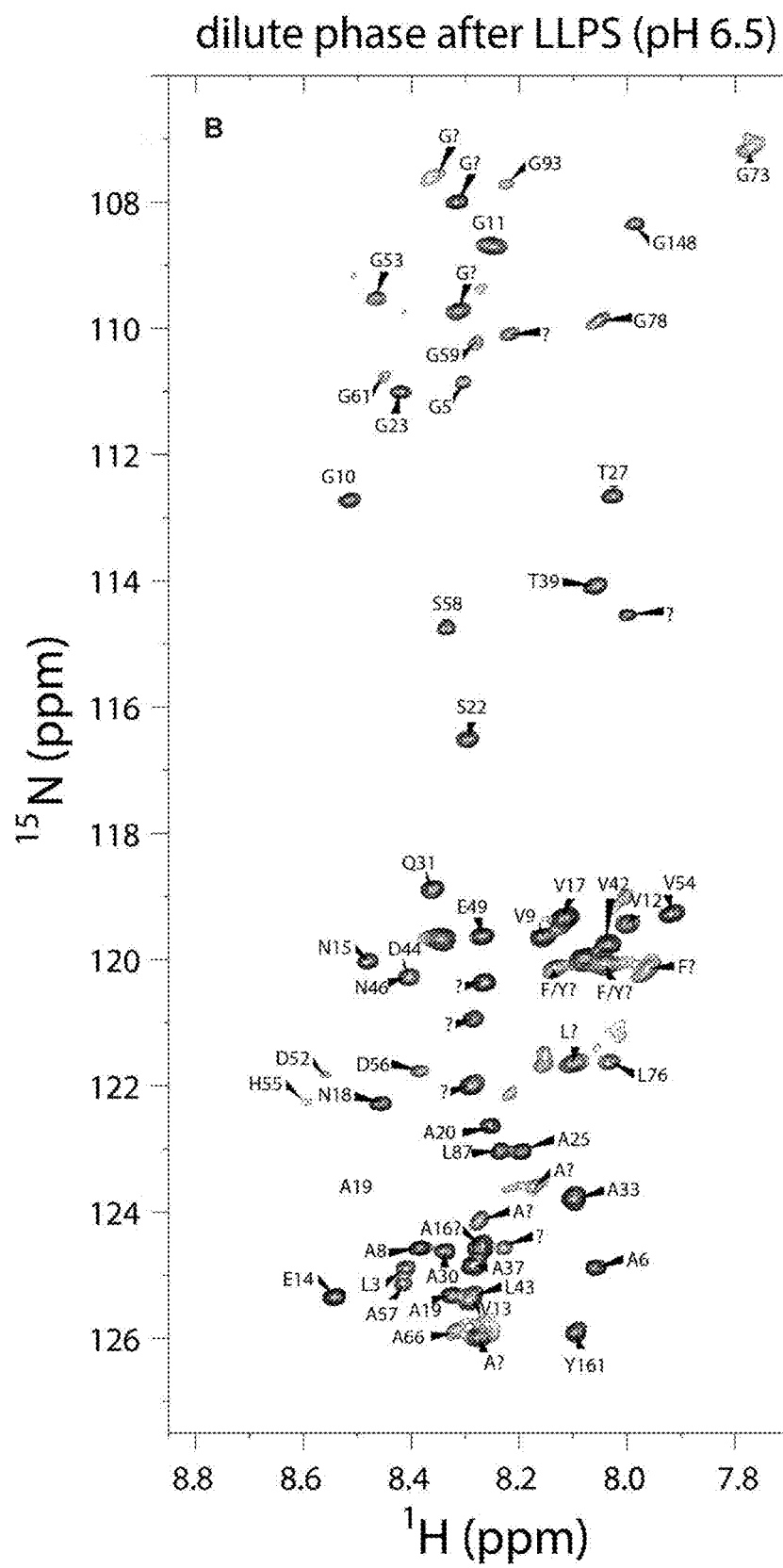
Figure 17C:
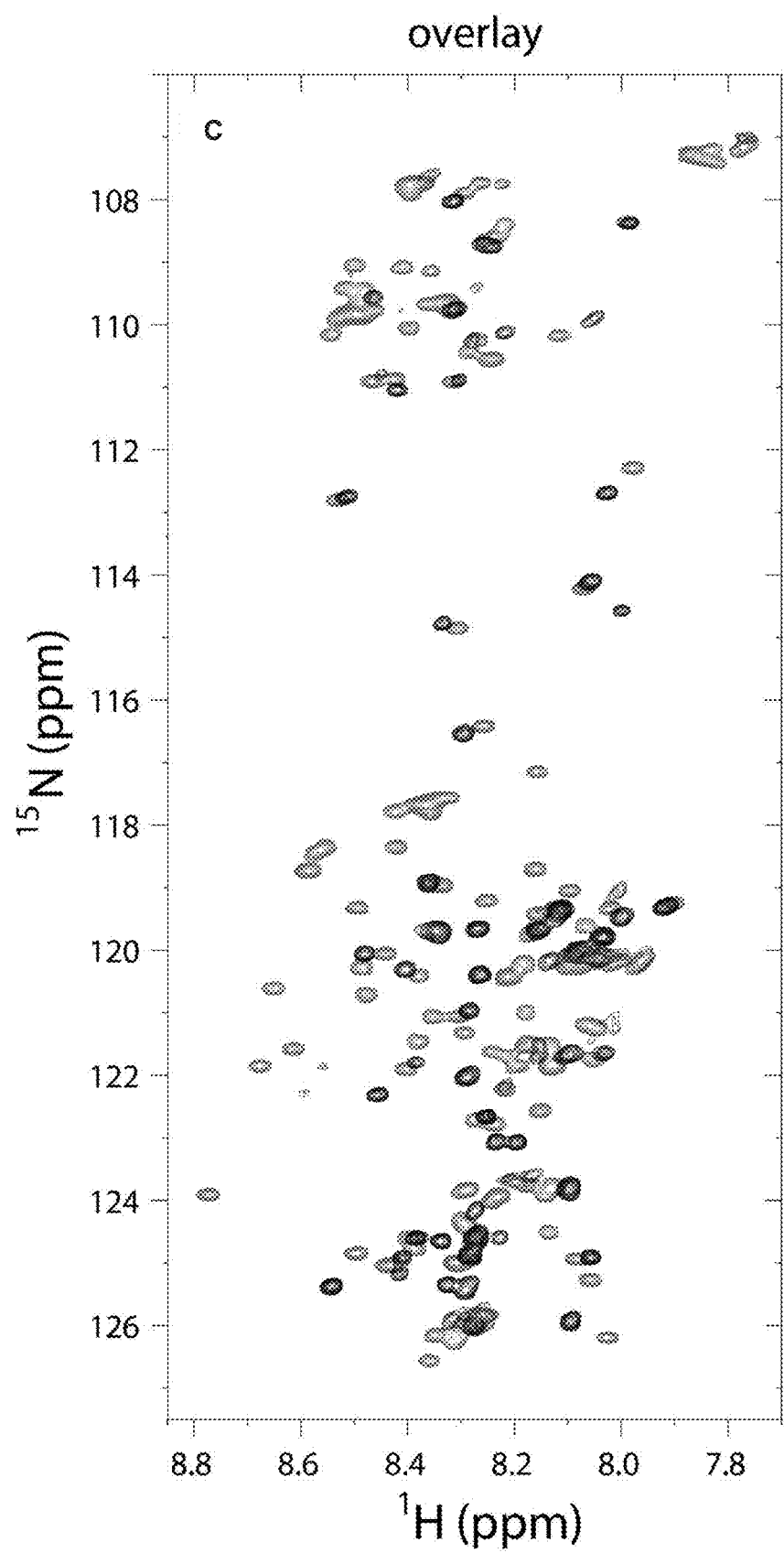
Figure 19:
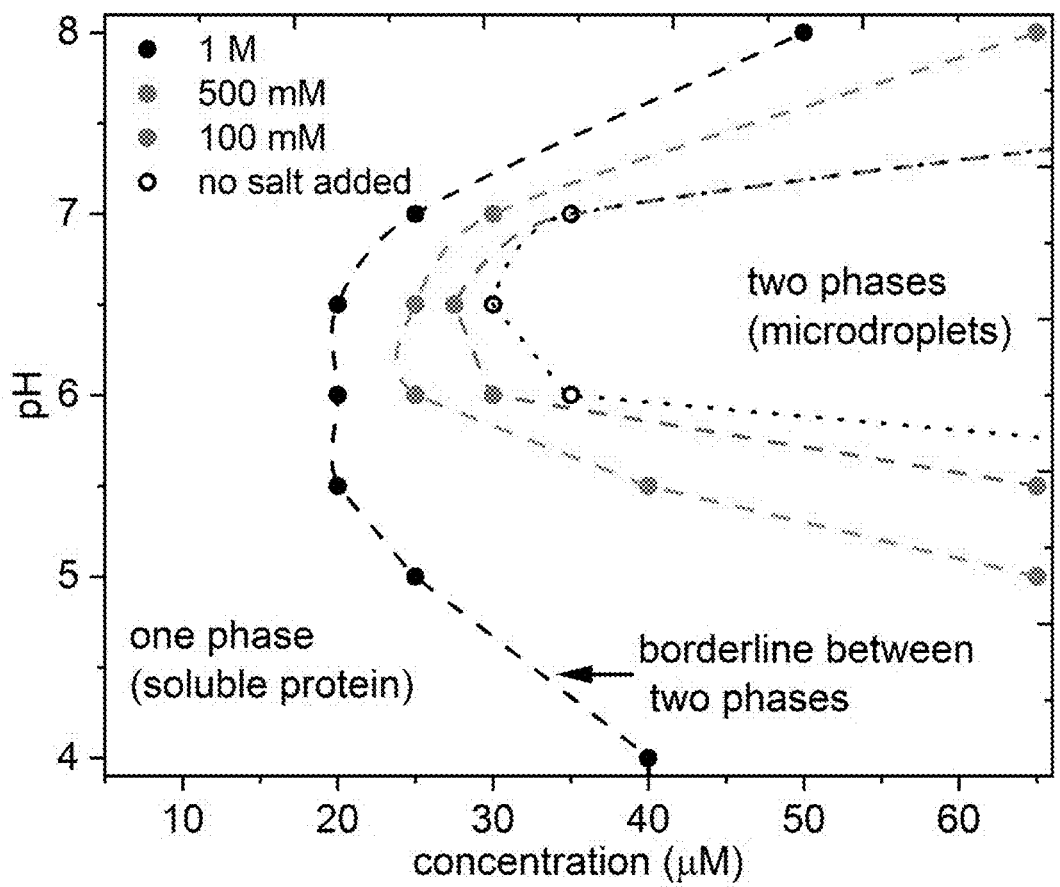
FIG. 19. Phase diagrams of DgHBP-1 at different pH values as a function of protein concentration and ionic strength. The estimated boundary lines determine the pH at which LLPS (micro-droplets) was first observed. Ionic strength of the buffers (FIG. 35) adjusted with NaCl.
Figure 20A:
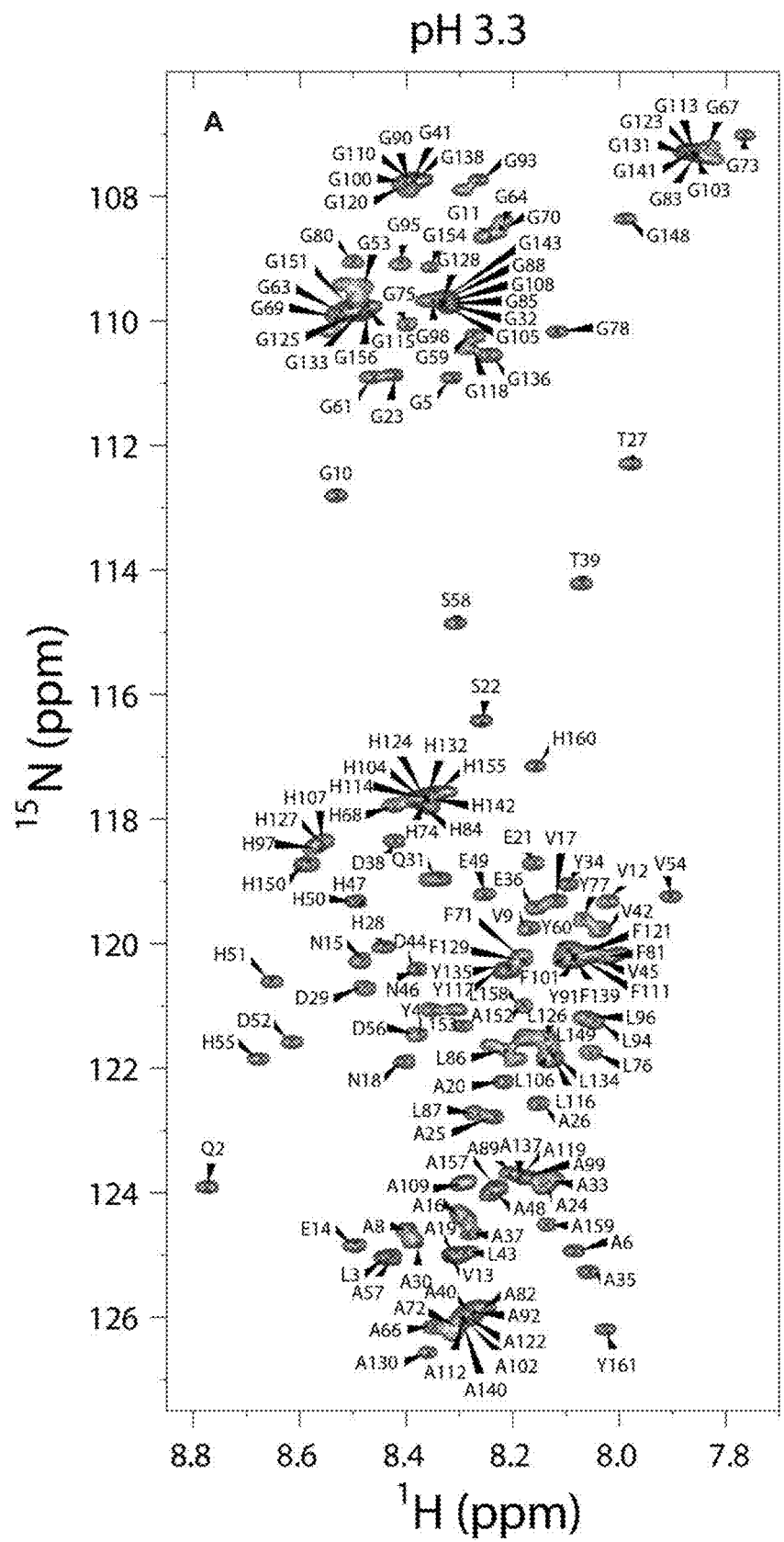
FIGS. 20A-20E. $^{1}$H-$^{15}$N Heteronuclear Single Quantum Coherence (HSQC) spectra of HBP-1 at different pH values ((A) pH 3.3, (B) pH 4.5, (C) pH 5.5, (D) pH 6.5, (E) dilute phase after LLPS (pH 6.5)). Spectra acquired at T=298° K. and a protein concentration of 2 mg/ml (130 µM).
Figure 20B:
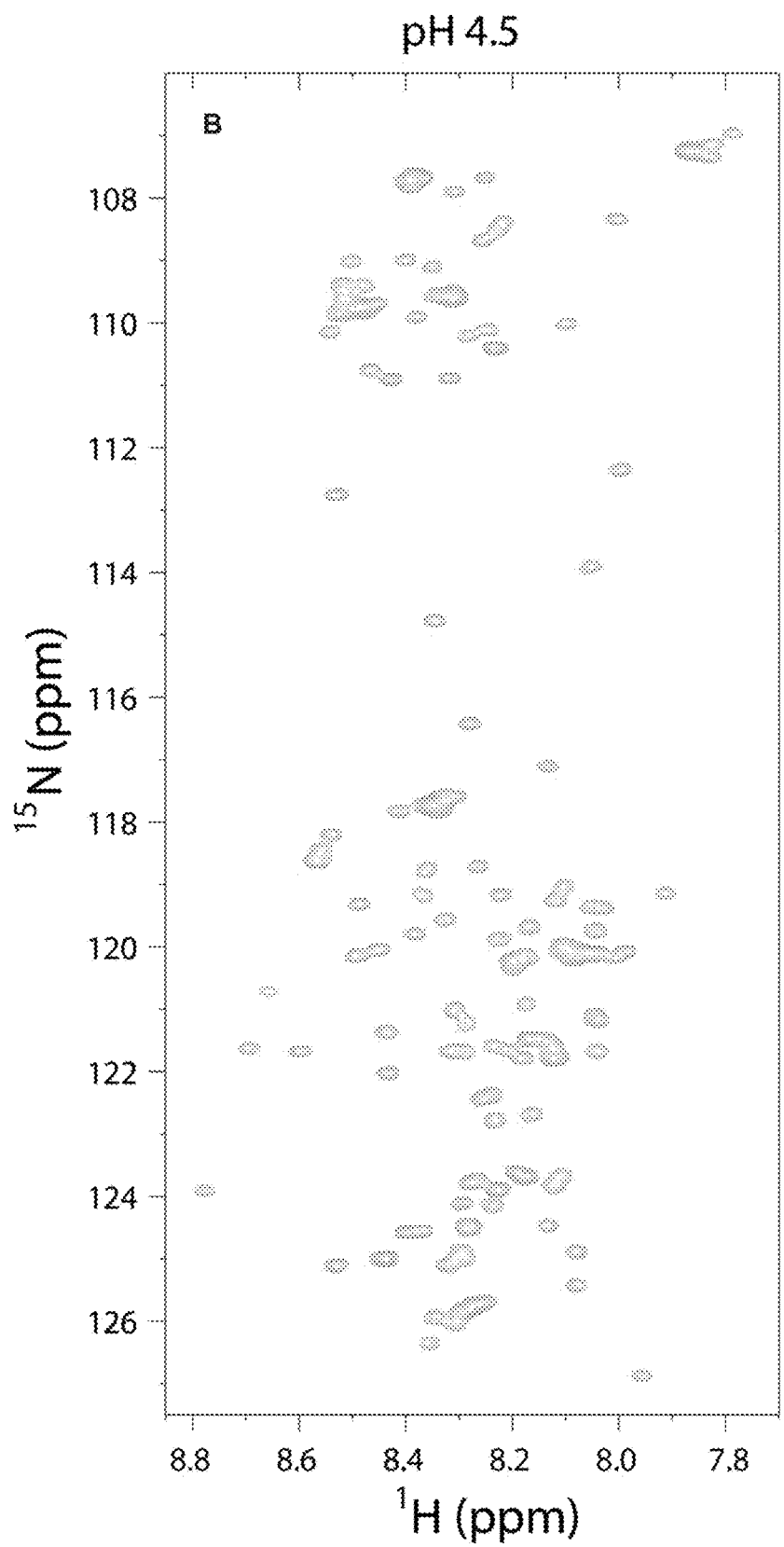
Figure 20C:
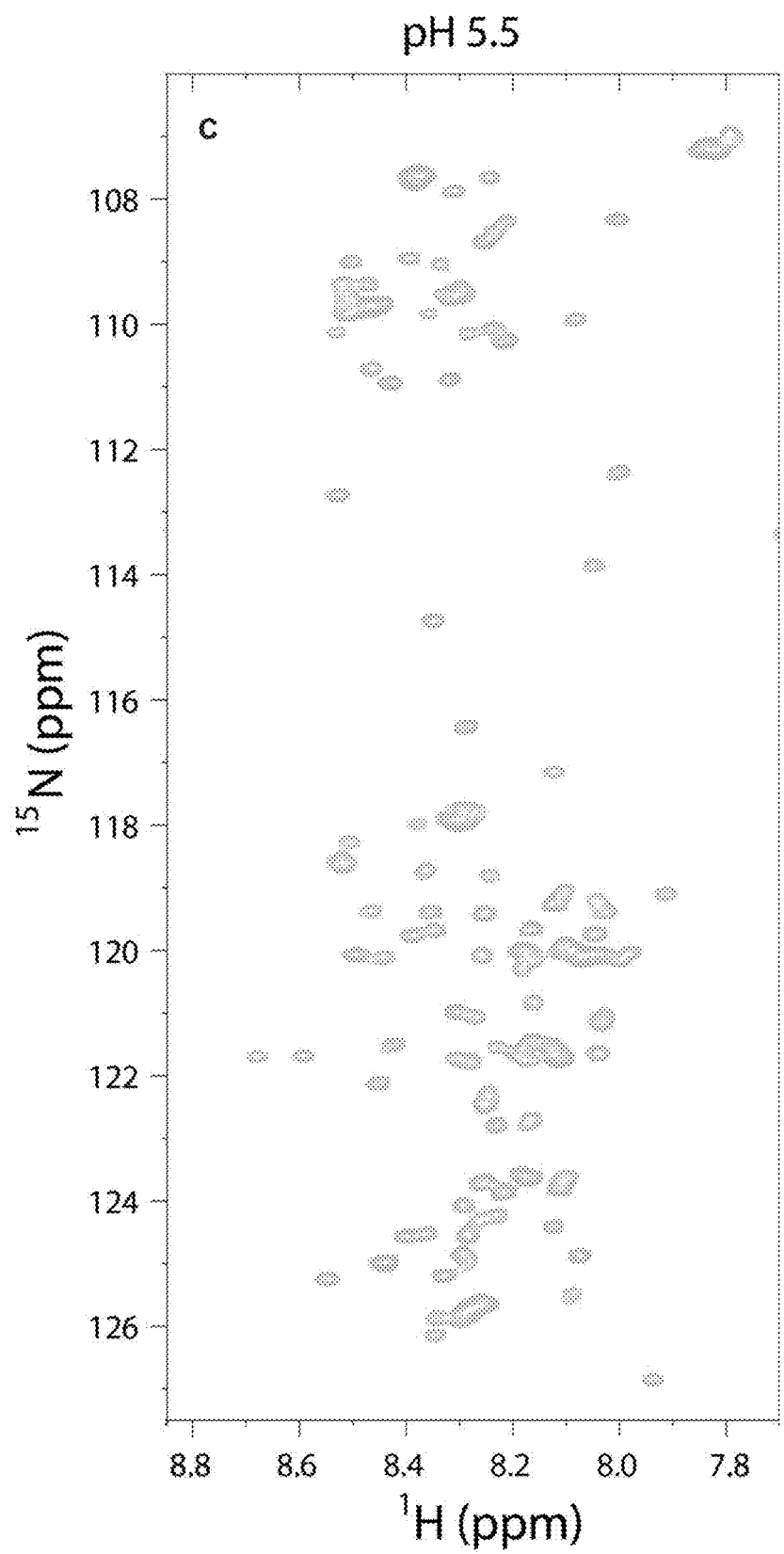
Figure 20D:
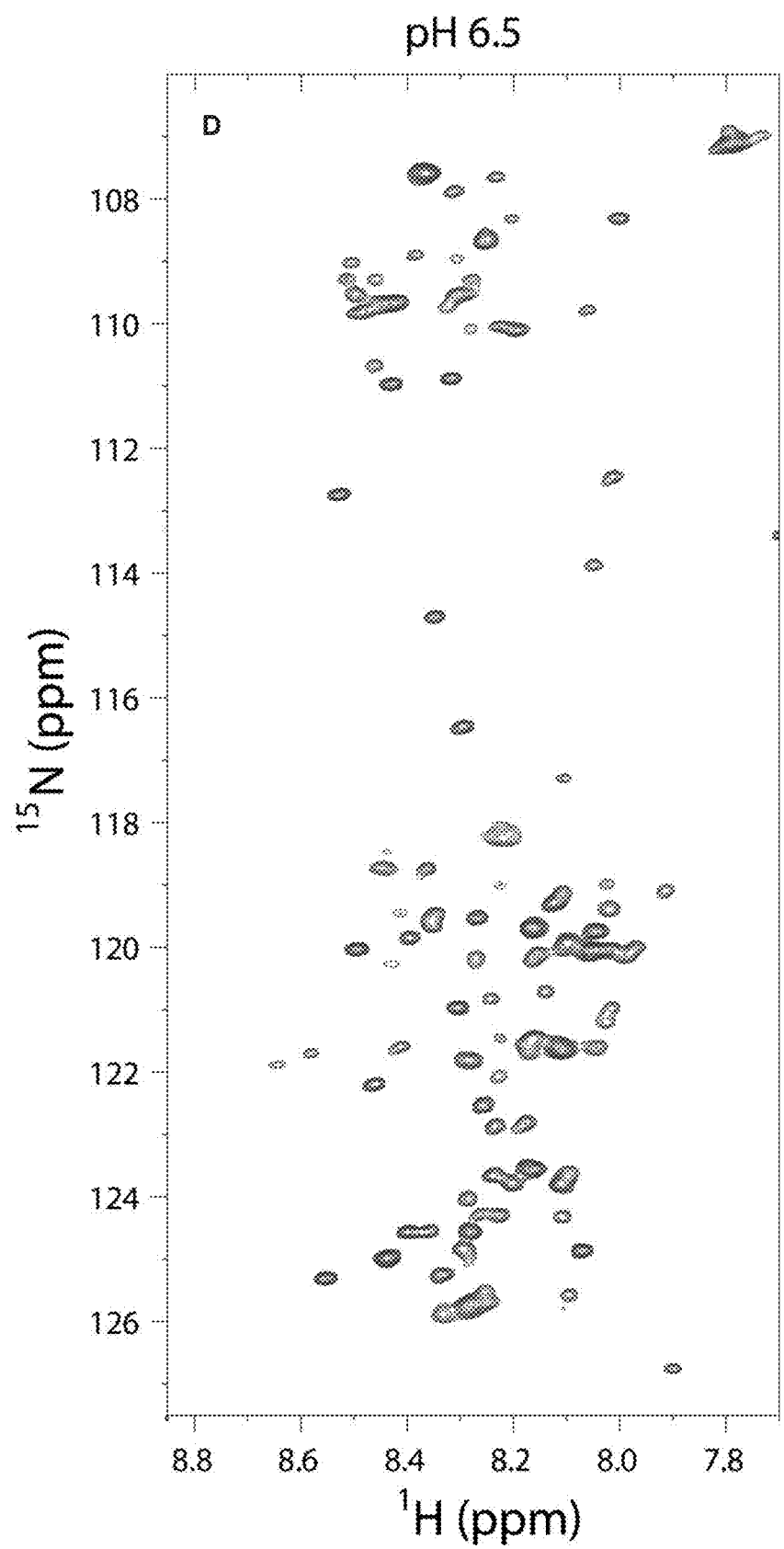
Figure 20E:
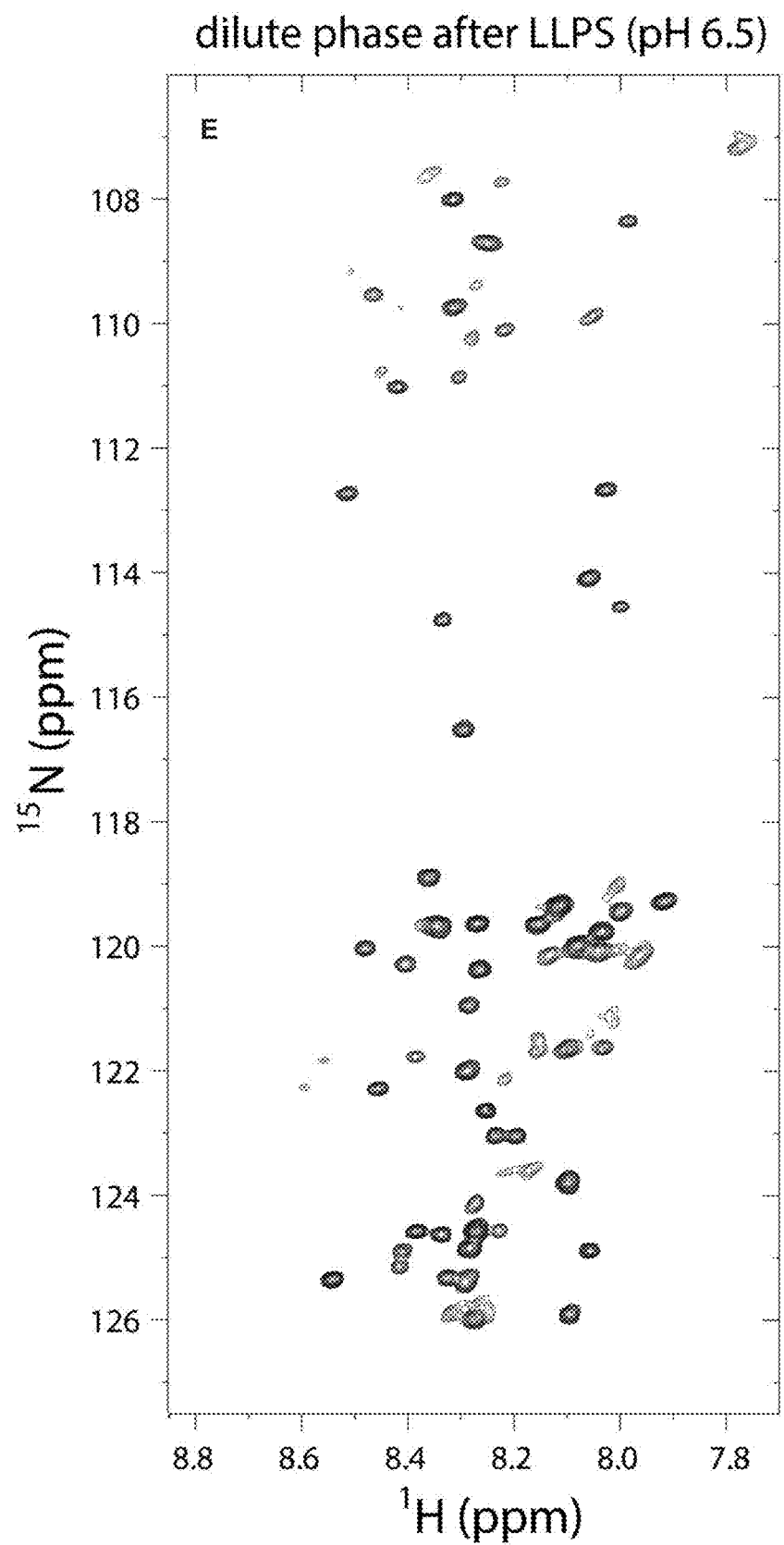
Figure 21A:
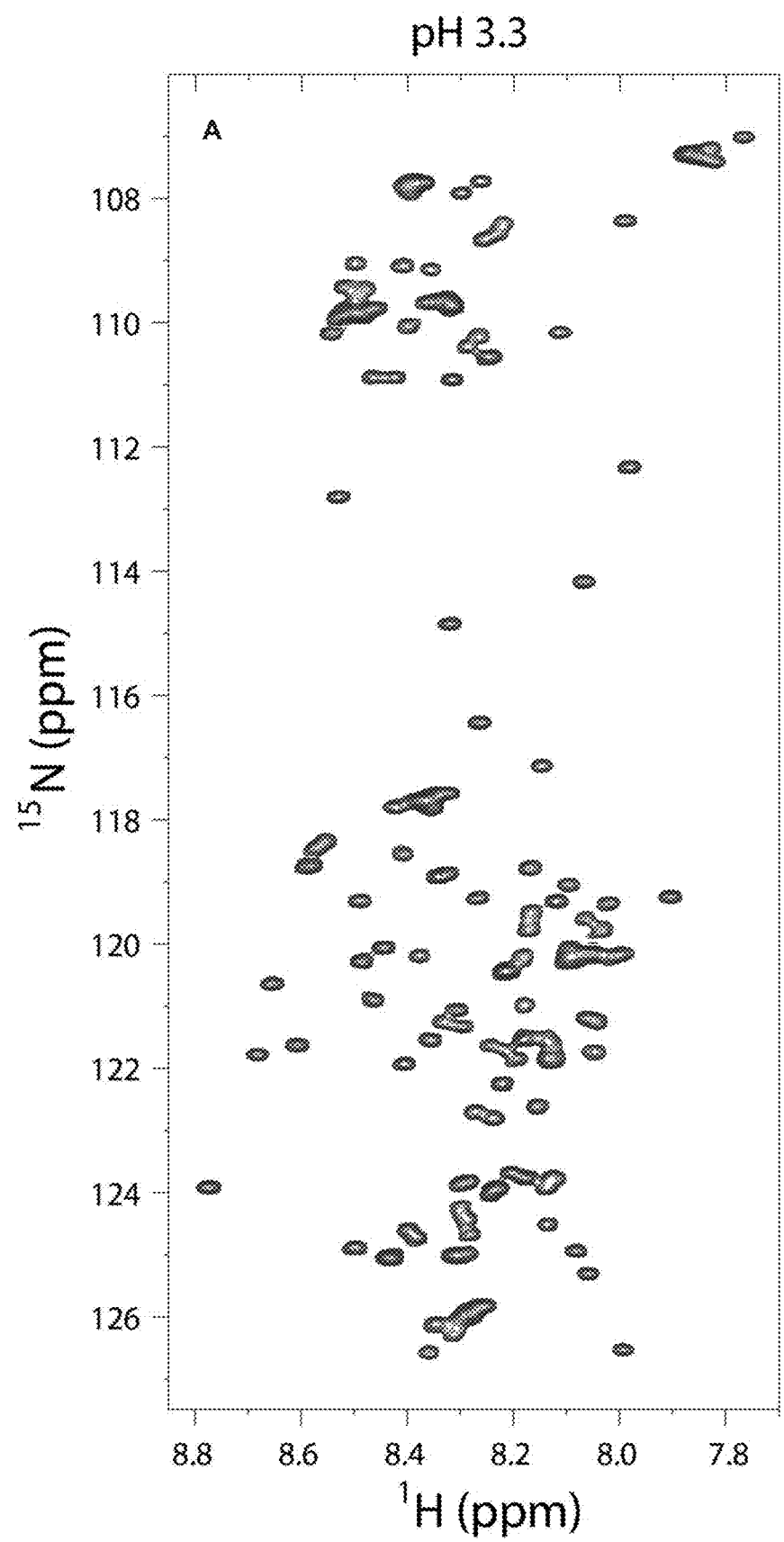
FIGS. 21A-21D. HSQC spectra of DgHBP-1 at different pH values ((A) pH 3.3, (B) pH 4.5, (C) pH 5.5, (D) dilute phase after LLPS (pH 6.5)) acquired at a lower protein concentration compared to initial conditions (FIGS. 20A-20E). Spectra acquired at T=298° K. and a protein concentration of 0.5 mg/mL (32 µM).
Figure 21B:
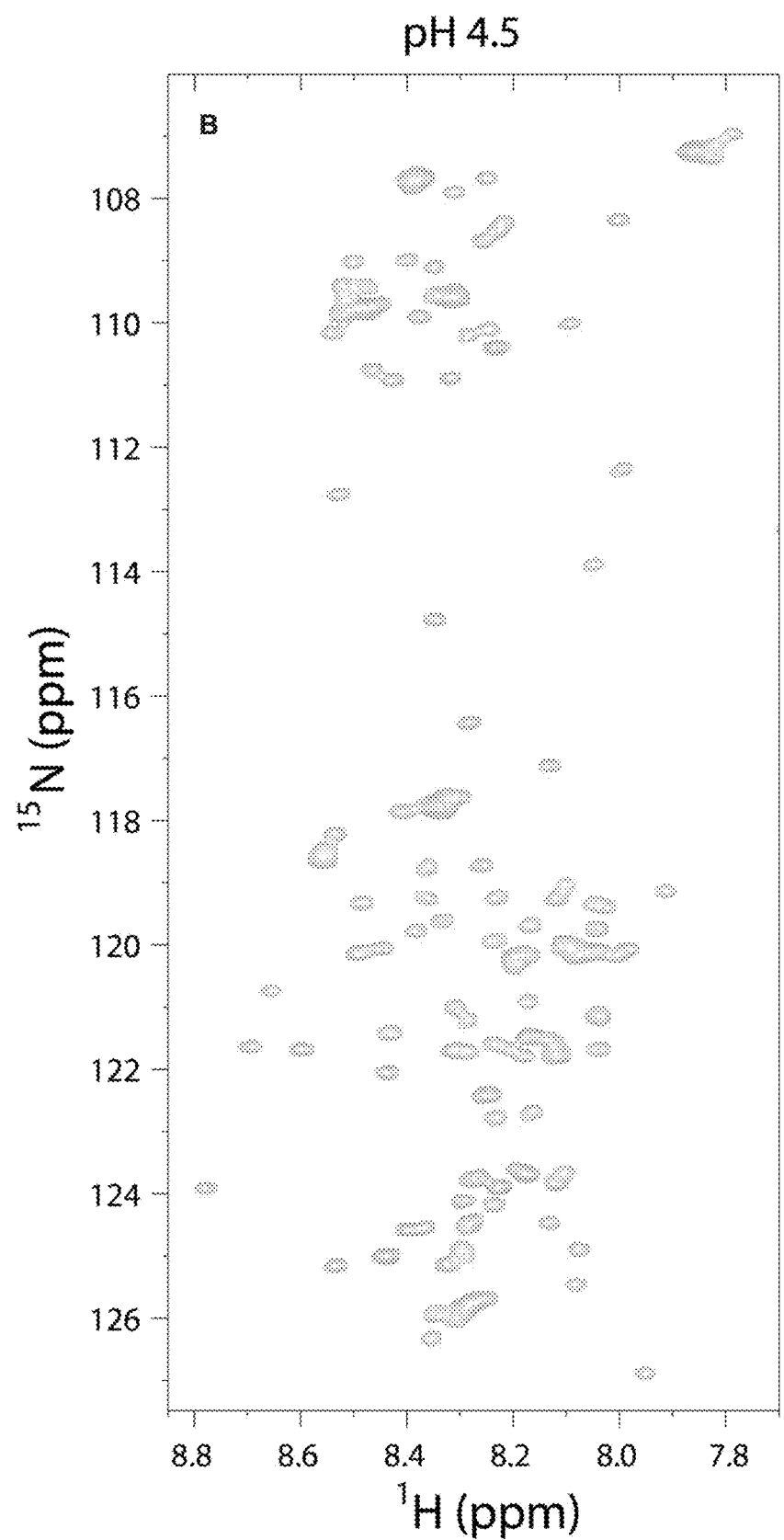
Figure 21C:
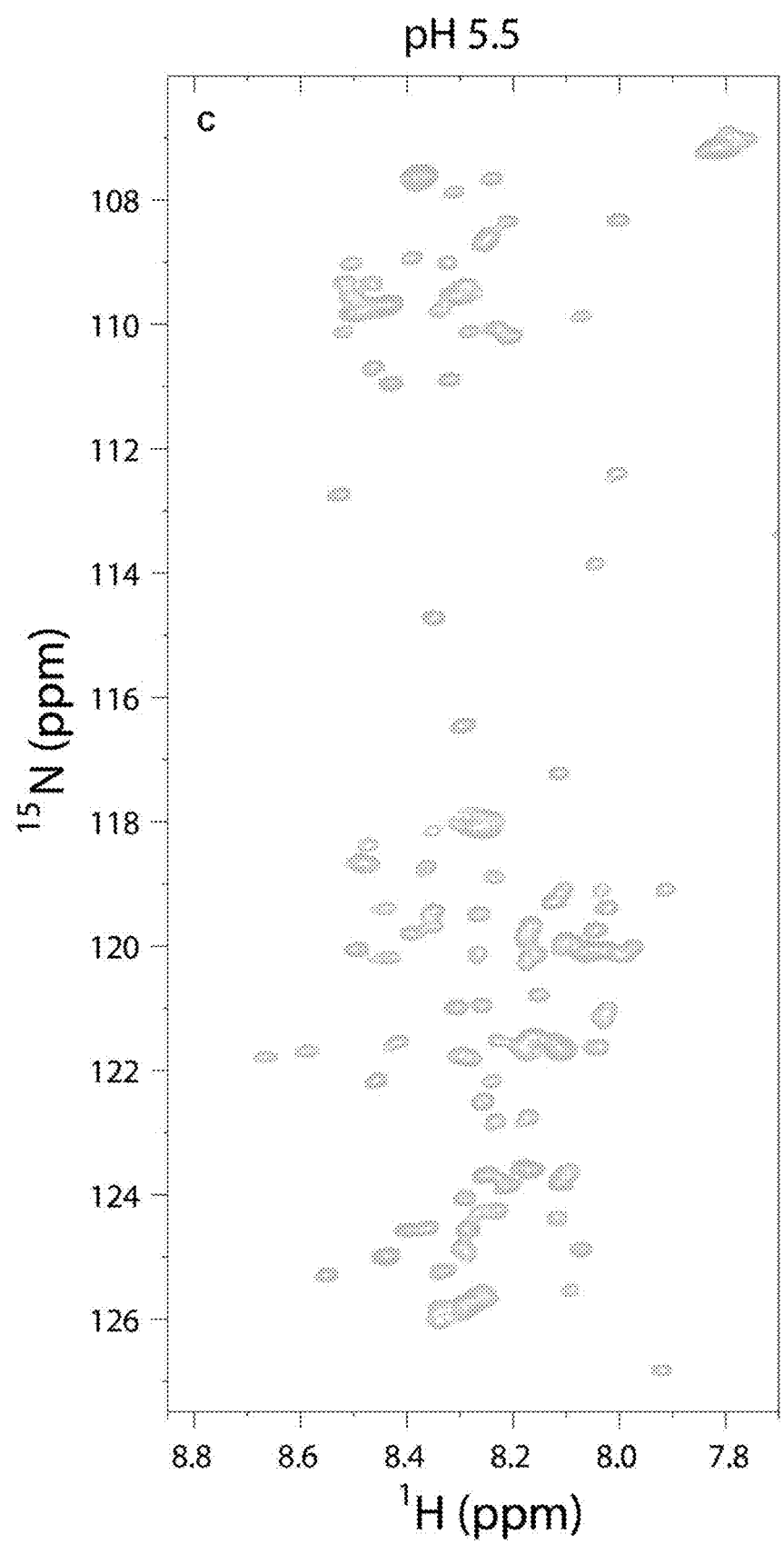
Figure 21D:
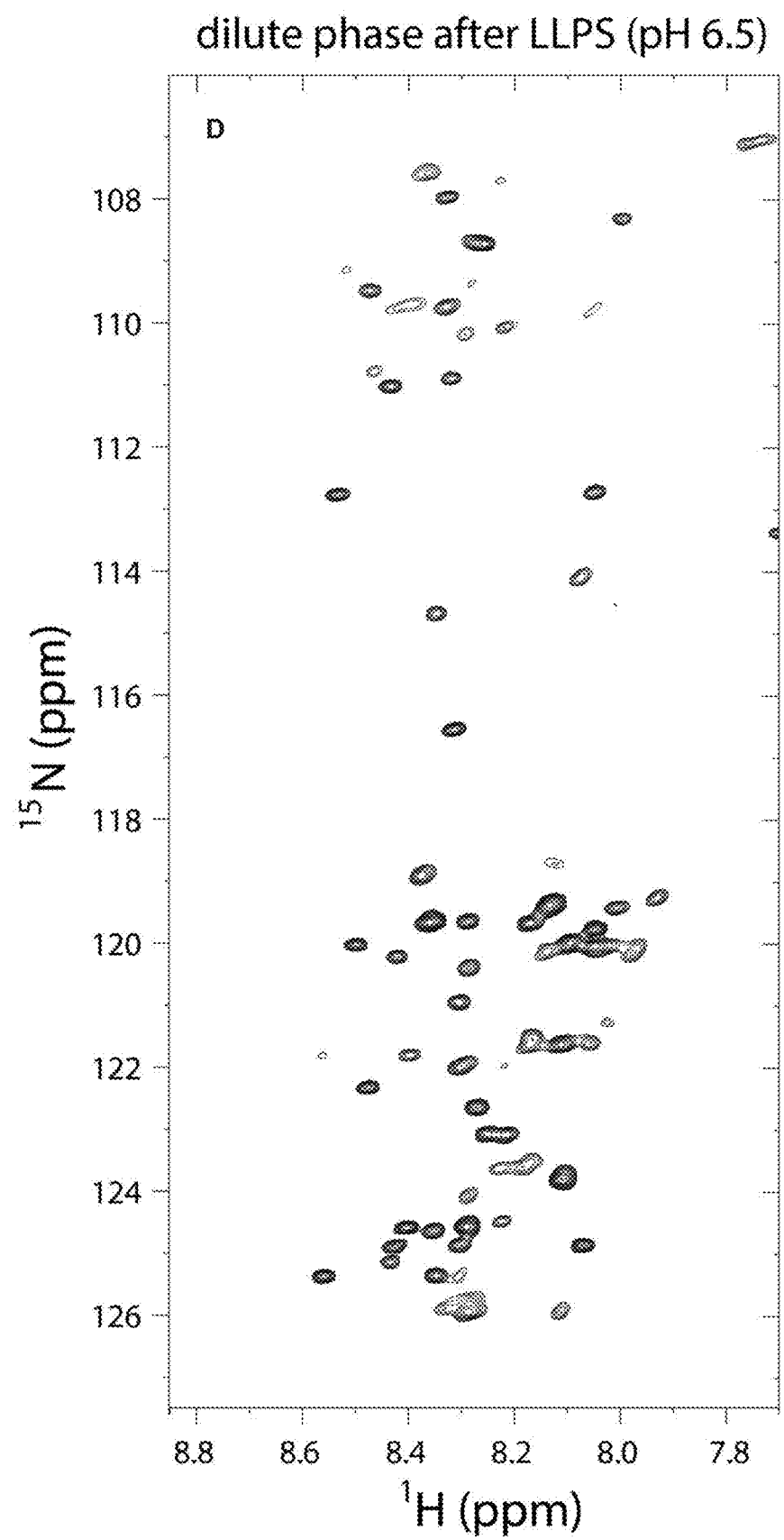
Figure 22A:
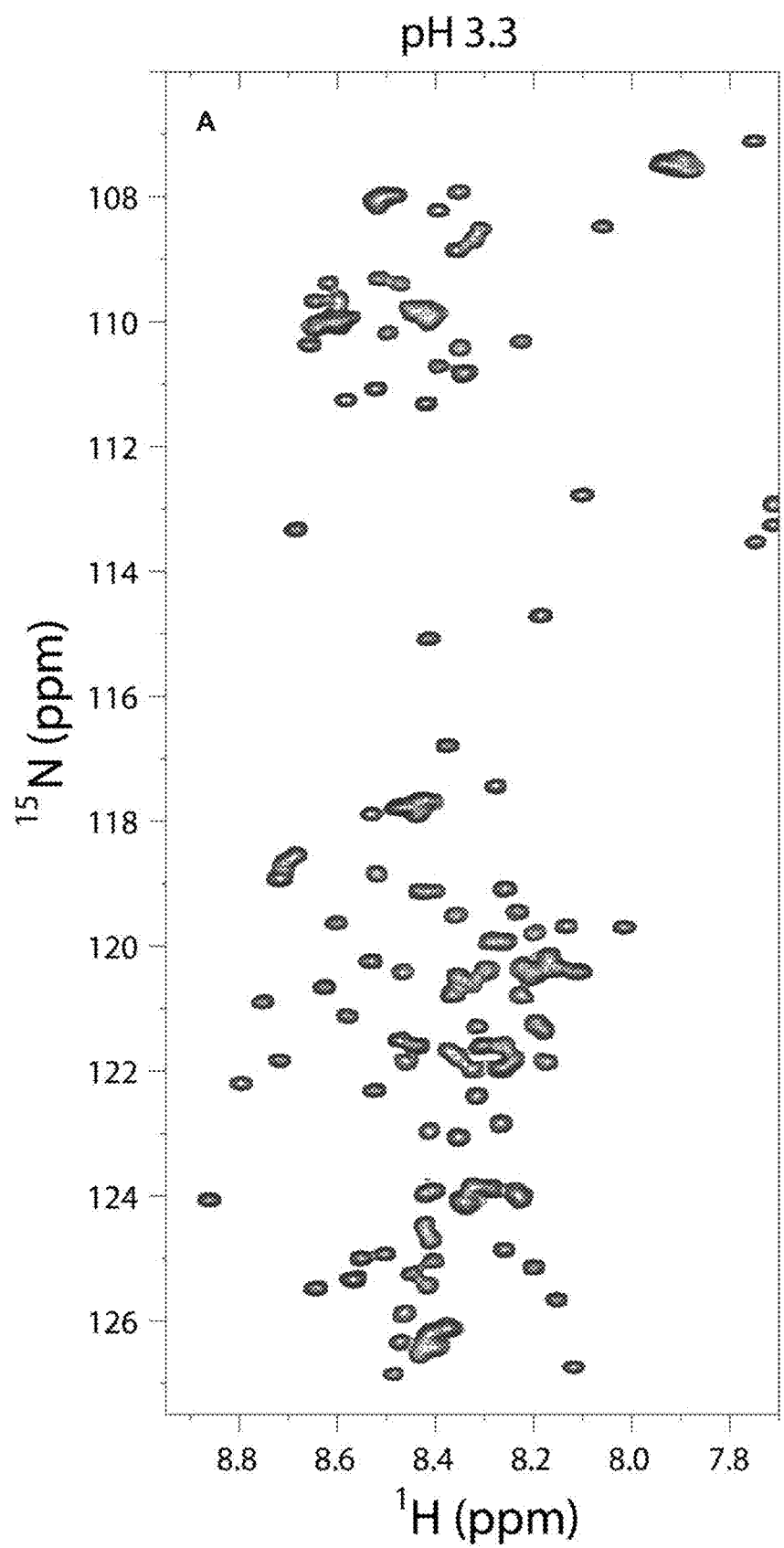
FIGS. 22A-22D. HSQC spectra of DgHBP-1 at different pH values ((A) pH 3.3, (B) pH 4.5, (C) pH 5.5, (D) dilute phase after LLPS (pH 6.5)) acquired at a lower temperature (T=279° K.) and a lower protein concentration of 0.5 mg/mL, 32 µM) compared to initial conditions (FIGS. 20A-20E).
Figure 22B:
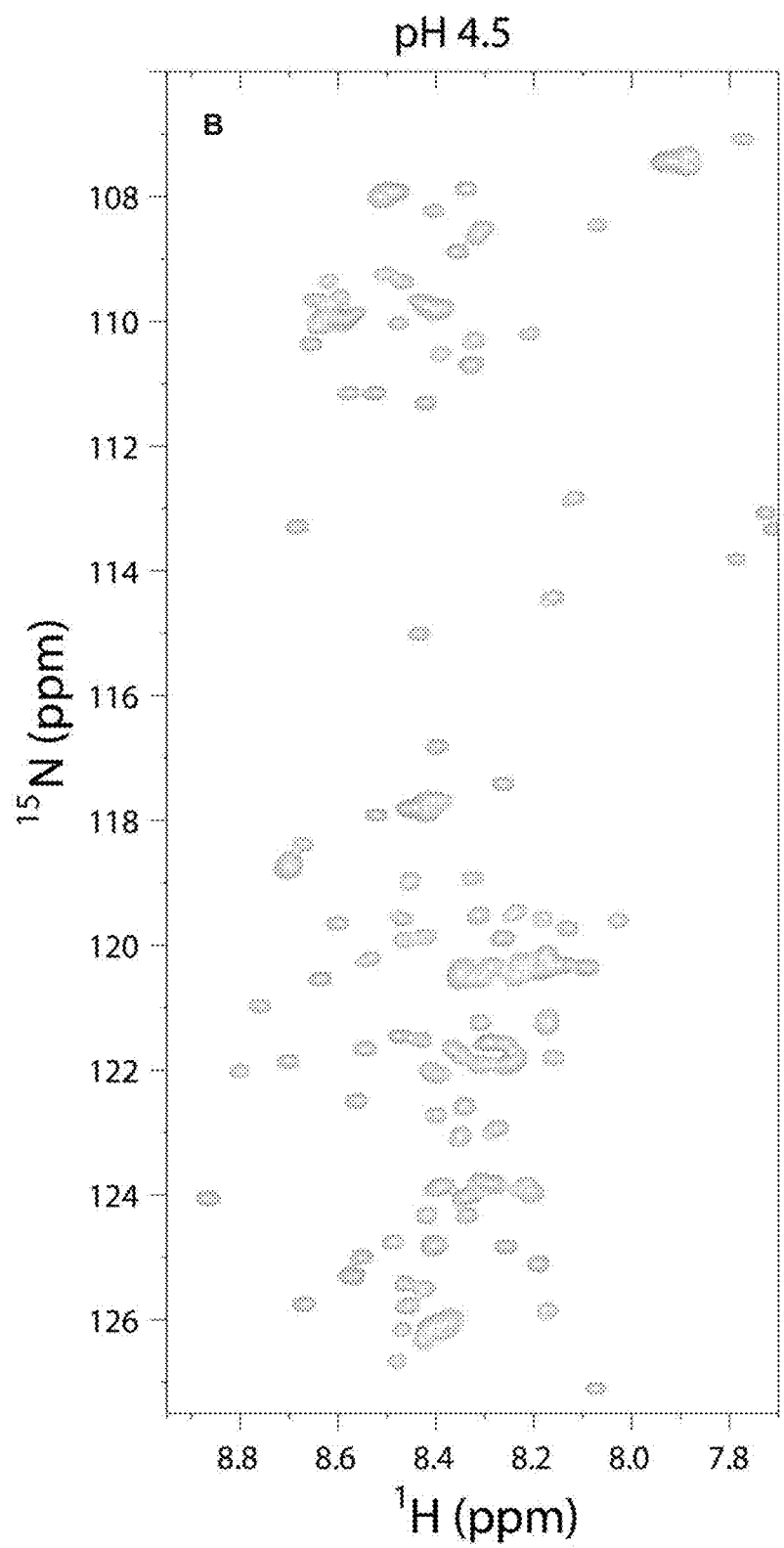
Figure 22C:
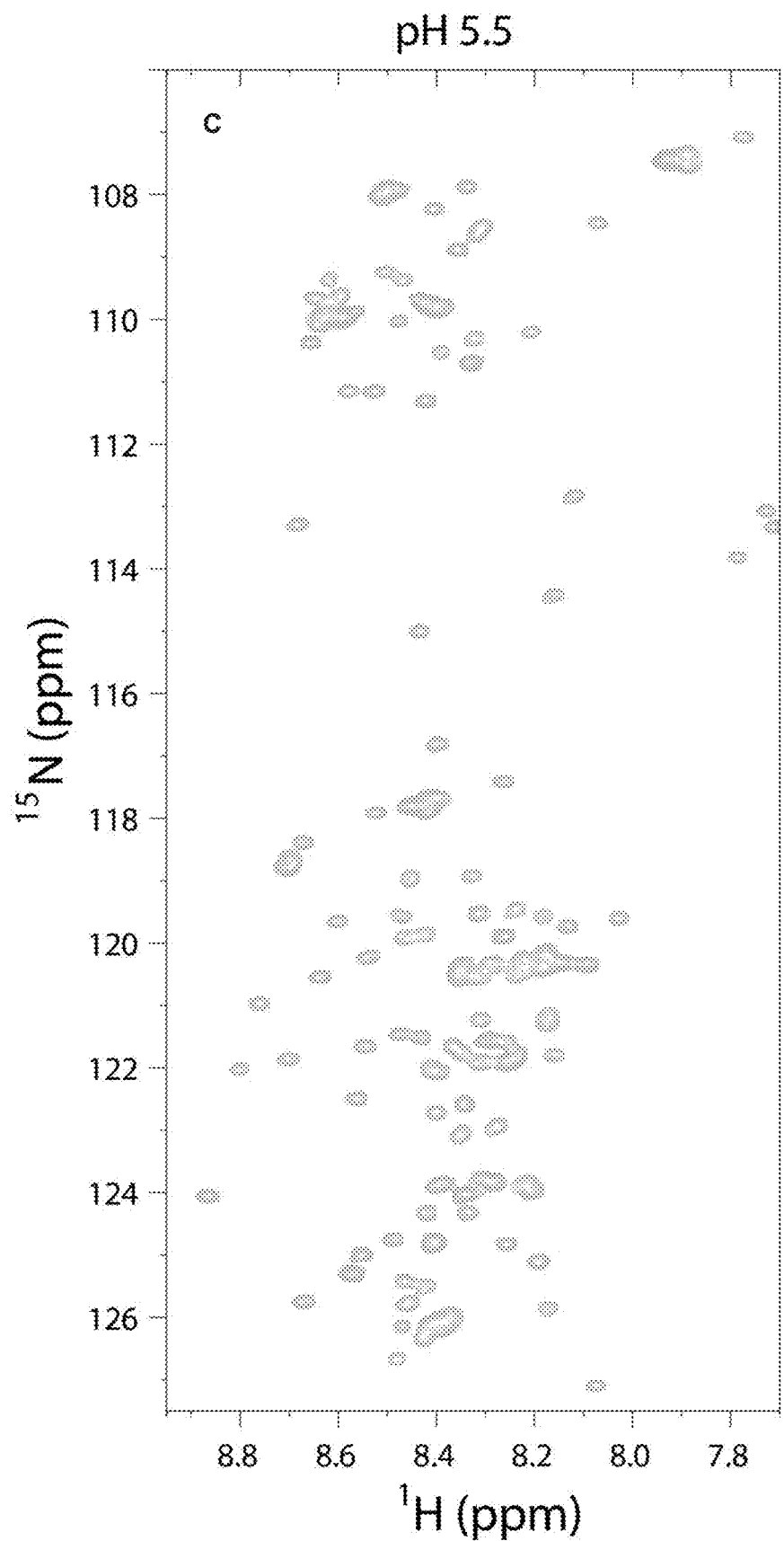
Figure 22D:
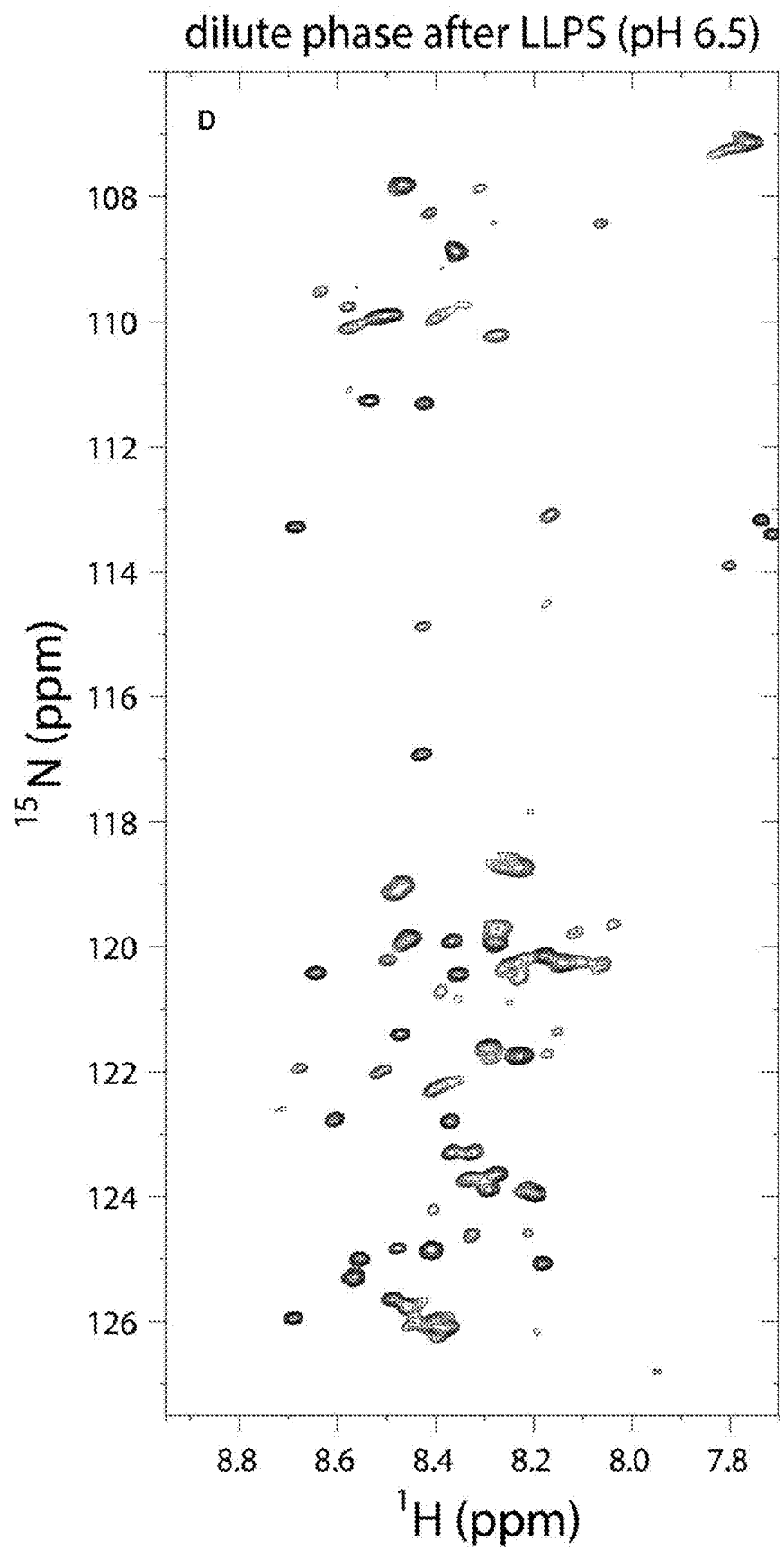

LLPS of DgHBPs is triggered by changes in pH and ionic strength. DgHBP-1 underwent LLPS at a minimal concentration of 20-30 µM in a narrow pH range 6.5-7.5, which is close to the proteins' isoelectric point (predicted pI=6.03) and could be broadened by increasing protein and salt concentration (phase diagrams presented in FIG. 19). To precisely probe the residues involved in LLPS of HBP-1, a set of $^1$H-$^{15}$N-HSQC spectra with a gradual increase of the pH from 3.3 (soluble state) (FIG. 17A) to 6.5 (at which point LLPS was initiated (FIGS. 20A-E)) was recorded. Finally, the spectrum from the diluted phase after LLPS was measured, when the coacervate micro-droplets had sedimented (FIG. 17B). The overlay with the spectrum acquired in initial conditions (FIG. 17C) indicated the absence of resonances assigned to glycine (Gly), His, alanine (Ala), and leucine (Leu) residues located mainly in the C-terminal modular repetitive region, suggesting that these residues were involved in transient interactions that were absent at acidic pH. As a control a set of spectra at 75% lower concentration compared to the initial conditions (FIGS. 21A-D) and at lower temperature (279° K. vs. 298° K. in initial conditions, FIGS. 22A-D) was acquired to probe possible exchange between monomeric and oligomeric states or exchange with water molecules, respectively. For both experiments at pH 6.5, the intensity losses of the same cross-peaks were detected, confirming the specific involvement of these residues (located mostly in the modular repeats of DgHBP-1) during LLPS.

Analysis of Modular Repeats Driving Phase Separation of DgHBPs—Key Role of GHGxY Motifs To study how the C-terminal modular domains' arrangement influences self-coacervation of HBP-1, a series of sequence variants was designed (FIG. 23A-D, full sequences in FIGS. 24A-C; SEQ ID Nos. provided in Figure description) and their ability to phase separate at various pH and salt (NaCl) concentration was investigated using optical microscopy (FIGS. 23E-F). First, a protein mutant lacking the first 66 amino acids but containing all modular repeats of the C-terminus (V1-C) was created. This mutant underwent phase separation and formed coacervates at similar protein concentration and pH range compared to the full-length protein, confirming hypothesis that C-terminal modular repeats are responsible for its phase separation behavior. Next, a variant lacking the first 31 amino acids of the repetitive region (V2-C) was studied. This variant formed coacervates similarly to V1-C and DhHBP-1 wild type but required a slightly higher protein concentration (ca. 30 µmol), indicating that the full length of the modular region was not required to induce phase separation.

To map out the minimal sequence length required for phase separation, a series of DgHBP-1 mutants with various lengths of the repetitive region was designed. The mutants were created by introducing a single Lys at different preselected locations, allowing to utilize trypsin cleavage to tune the length of the cleaved fragments following enzyme digestion as well as to obtain variants exhibiting different lengths of the repeating domains (FIG. 23C and FIG. 24B).

Figures 23E, 23F:
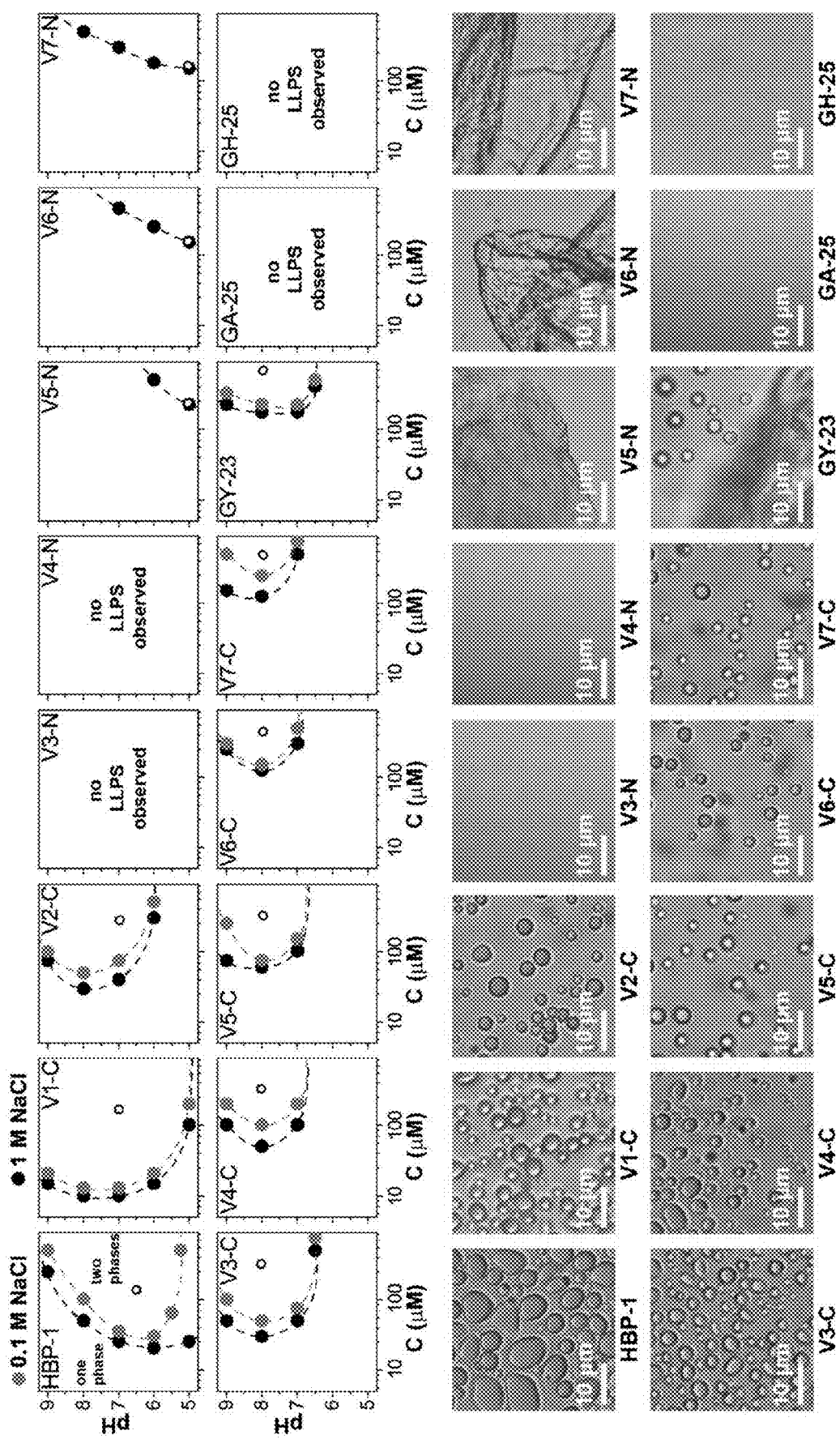

Then the LLPS behavior of all variants as a function of protein concentration and pH was analyzed, and at various salt concentrations and drew the phase diagrams shown in FIG. 23E. For N-variants, LLPS occurred for V5-N to V7-N only at high salt concentrations. On the other hand, LLPS could not be induced for V3-N and V4-N at all tested conditions. It was also observed that as peptide length increased, LLPS occurred over a broader range of conditions. Thus, for V7-N LLPS could be induced at pH as high as 8 provided the peptide concentration was at least 500 µM. For V6-N, the highest pH at which LLPS was observed was 7 (and a minimal peptide concentration of 400 µM), whereas for V5-N no LLPS occurred above pH 6. Correlating the results with the peptide design point out towards the importance of the GHGLY motif and the peptide length. For the longer V6-N and V7-N peptides containing two GHGLY motifs, LLPS could be induced over a wider range of conditions, whereas for the shorter V3-N and V4-N variants containing only one copy of GHGLY, no LLPS was observed no matter the conditions. And for the intermediate length V5-N with one GHGLY motif, LLPS could be induced but only under narrow conditions. Moreover, the separated phases of the longer variants exhibited a different morphology compared to the full-length protein (FIG. 23F), forming dense hydrogel-like structures that did not disperse into the surrounding buffer. This behavior may be linked to the stronger hydrophobicity of V5 to 7-N compared to other variants, which may favor hydrogel formation by hydrophobic interactions.

A similar trend was observed for the C-terminus variants. V3-C, which contained the longest section of the repetitive region, phase-separated at the lowest protein concentration (30 µM at pH 8) and in the broadest pH range among all tested variants. On the other hand, the shorter Vx-C variants exhibited LLPS under a narrower range of conditions and required higher protein concentrations.

To further assess the role of the GHGLY motif, the coacervation ability of the DgHBP-1 derived GY-23 peptide (containing two GHGLY copies) was compared with two other synthetic peptides made of very similar fragments of HBP-1 repeats (GA-25 and GH-25), but harboring only one GHGLY motif (FIGS. 23D and 24C). Only GY-23 phase-separated, forming coacervate micro-droplets suspended in solution as well as a dense hydrogel-like structure (condensed, solid-like coacervates, FIG. 23F). In contrast, GA-25 and GH-25 remained in solution in all tested buffer conditions (FIG. 23F). It should be noted that sequence motifs similar to GHGLY are also present in the C-terminal of DgHBP-2 protein, which contains seven copies of the GHGxY motif (where x can be Val, Pro, Leu) arranged in tandem (FIGS. 25A-C). A peptide (DgHBP-2-pep) composed of 5 copies of GHGxY was previously shown to phase separate and form coacervates in the same way as the full-length protein.

In order to confirm the central role of GHGxY motifs on LLPS of DgHBP-2, trypsin cleavage was utilized to obtain shorter fragments of DgHBP-2 and their ability to phase-separate was tested. Since the protein possesses only two trypsin recognition sites at positions R81 and R172, we obtained the N-terminal (M1-R81) fragment that lacked the modular repeats, the C-terminal (A82-R172) containing the whole repetitive region, and a short G173-Y175 peptide that was discarded (FIG. 25B). As expected only the C-terminal fragment phase-separated into coacervates (FIG. 25C). Next, a series of short peptides containing different arrangement of repetitive units present in DgHBP-1 and DgHBP-2 (FIG. 26A) we designed and their phase separation behavior was analyzed in the same way as for DgHBP-1 variants. Phase separation was observed for all 25-mer peptides containing two GHGLY motifs flanking the central region composed of 3 copies of the GAGFA or GHGLH sequences, as well as for a 20-mer peptide (GY-20) made of four copies of GHGLY motif arranged as tandem repeats. In contrast, no phase separation was observed when the peptide length was reduced to 15 amino acids, for example when 3 copies of the GHGLY motif were arranged in tandem (GY-15-V1) or when the GAGFA motif was flanked by GHGLY (GY-15-V2). Similarly, no phase separation was observed for deca-peptides composed of one or two GHGxY motifs or for pentapeptides GHGLY or GAGFA, respectively. Moreover, peptides with LLPS ability exhibited various rheological characteristics of the separated phase. GY-25-V1 peptide containing 3 copies of hydrophobic GAGFA motif phase-separated into a dense and compact hydrogel. On the other hand, GY-25-V2 and GY-20 peptides composed of less hydrophobic, His-rich motifs, only formed micro-droplets (FIG. 26B), while GY-23 peptide containing both types of motifs separated into micro-droplets as well as hydrogel-like condensed coacervates (FIG. 23F).

Taken together these results indicate that when at least two copies of the GHGLY motif are present in the tandem repeats, the phase separation ability is greatly enhanced. However, this condition is not sufficient and GHGLY copies must additionally be separated by a spacer composed of at least 3 copies of GAGFA or GHGLH motifs, or a combination of GAGFA/GFA and GHGLH motifs. Alternatively, the peptide must contain at least four tandem repeats of GHGLY motif to phase-separate. To corroborate the role of Tyr in phase separation, two GY-23 variants in which one of two Tyr was substituted with Ala (FIG. 26D) were prepared. Phase separation did not occur in both cases and in all tested conditions, further pointing out to the critical role of Tyr-Tyr interactions in driving phase separation.

Modular Interactions Initiating LLPS—Solution-State NMR Spectroscopy

Subsequently, NMR spectroscopy studies were carried out to assess the role of Tyr residues and to identify the detailed molecular interactions triggering and stabilizing LLPS. First, the $^1$H-$^{15}$N-HMQC spectrum in solution as well as a set of triple-resonance NMR spectra for peptide backbone assignment of soluble GY-23 at pH 3.3 was acquired. The $^1$H-$^{15}$N-HMQC spectrum yielded well-resolved peaks that could be fully assigned based on the carbon chemical shifts values obtained from the 3D experiments (FIG. 27A). Observed Cα and Cβ chemical shifts showed no significant differences from the average values of random coil structures (FIG. 28), confirming that the peptide displayed no propensity towards a specific secondary structure.

Figure 29:
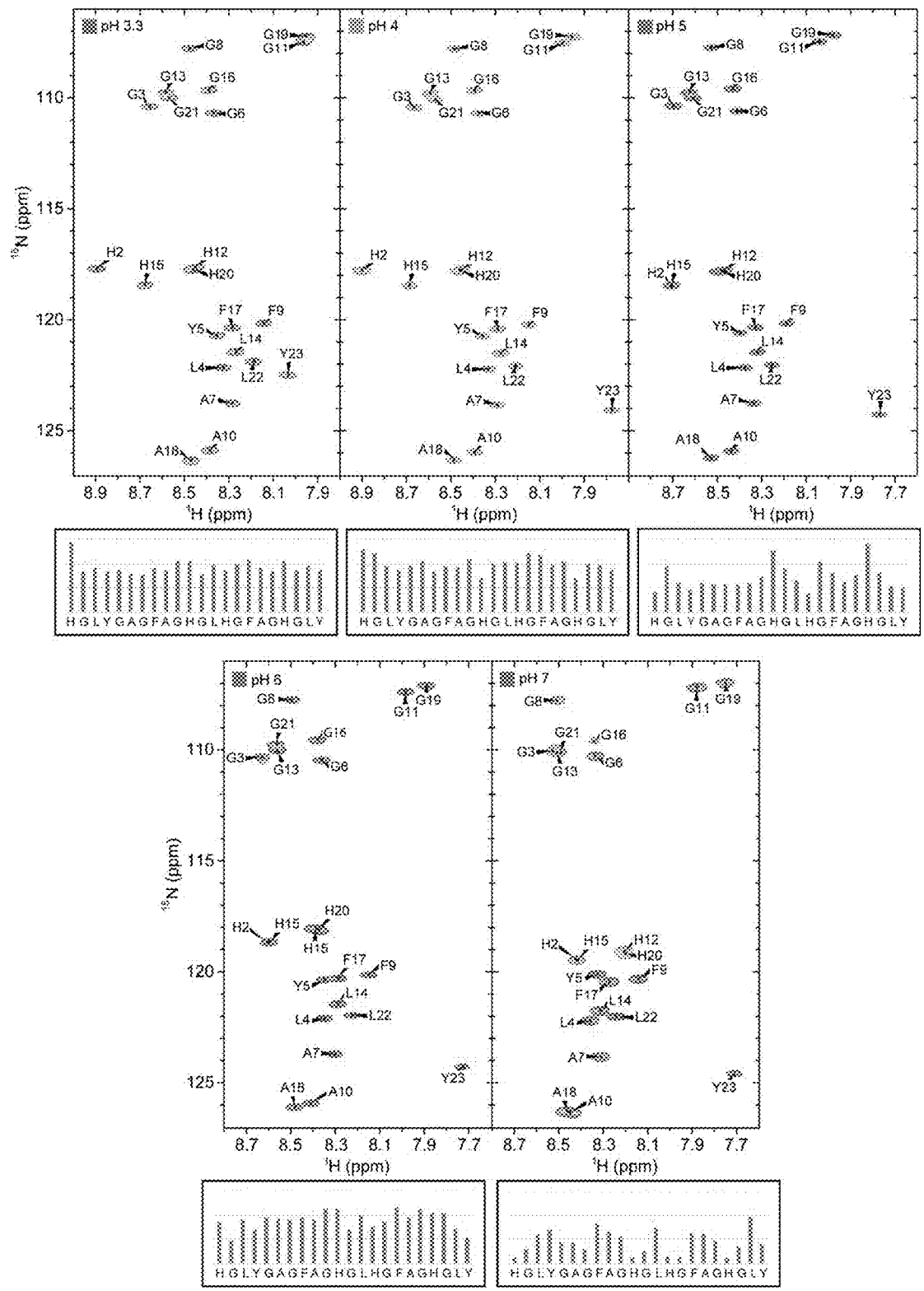
FIG. 29. $^{1}$H-$^{15}$N-HMQC spectra of GY-23 at different pH values. Bar graphs represent relative peak intensity for the assigned residues. Spectra acquired at 298° K. and a peptide concentration of 1.5 mM.
Figure 30A:
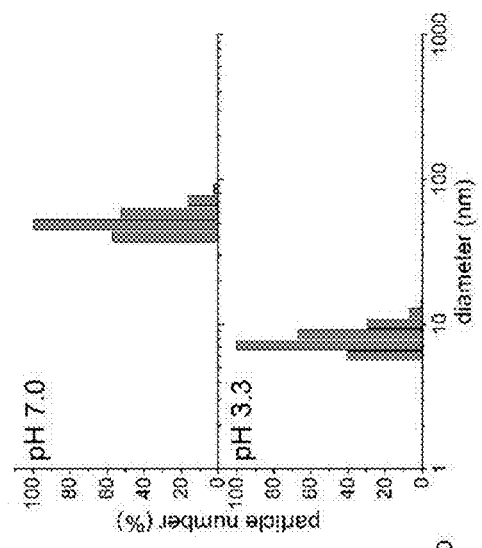
FIGS. 30A-30C. SAXS and DLS of GY-23 peptide. (A) SAXS experimental curves of the peptide before and after coacervation. After LLPS, the dilute and coacervate-rich phases were measured following centrifugation. The q-3 power-law region of the scattering data is highlighted, with the black line a guide for the eye. The calculated fit for the peptide assemblies from the IFT method is also presented as a continuous red line. (B) Corresponding p(r) profile calculated from the SAXS data in (A) using Eq. 1 (materials and methods). (C) Hydrodynamic diameter (DH) measured by DLS of GY-23 in acetic acid (pH 3.3) and after coacervation (pH 7.0). Correlation functions showing the 'raw' data are presented in FIGS. 34A-B.

Next, the pH of the peptide solution has been titrated and changes in the $^1$H-$^{15}$N-HMQC have been monitored (FIG. 27B). Major variations in the peak distribution and relative intensity at pH 4-6 were not observed (FIG. 29) compared to the initial state (pH 3.3, FIG. 30A), since in these conditions the peptide remained fully soluble. However, close to the LLPS point between pH 6-7, there was an observable major shift and decrease in the relative intensity of all cross-peaks assigned to His residues (FIG. 29) as well shifts in the positions of all Gly peaks flanking them. In addition, shift of the cross-peak assigned to Y5 was observed (FIG. 27B).

Figure 27F:
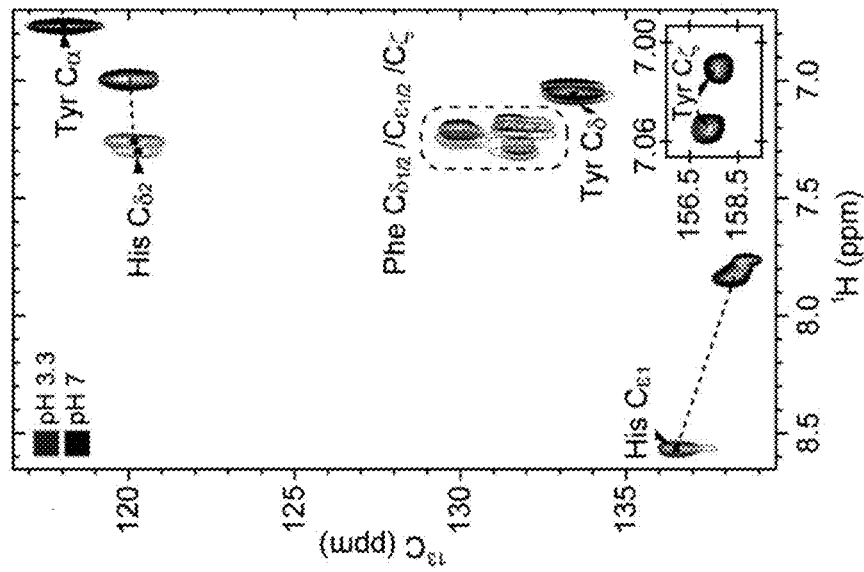
Figure 27E:
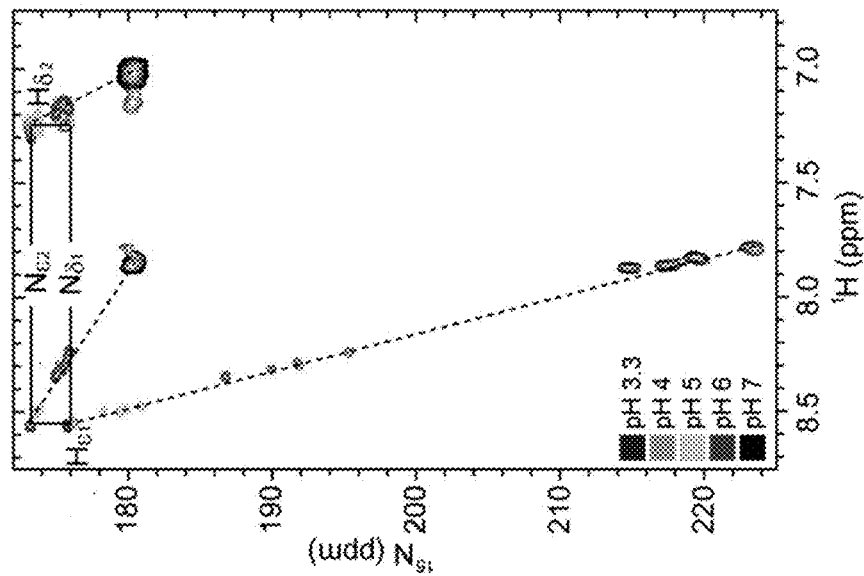
Figure 27D:
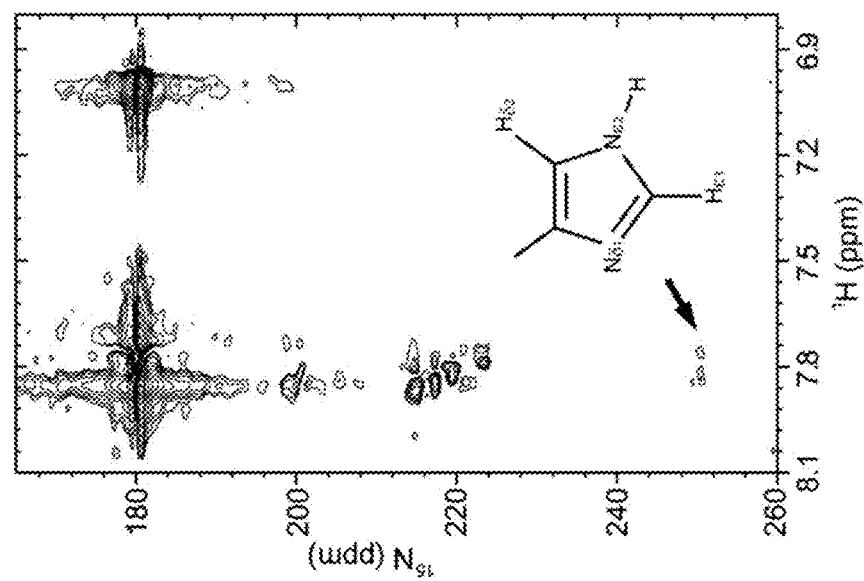
Figure 28:
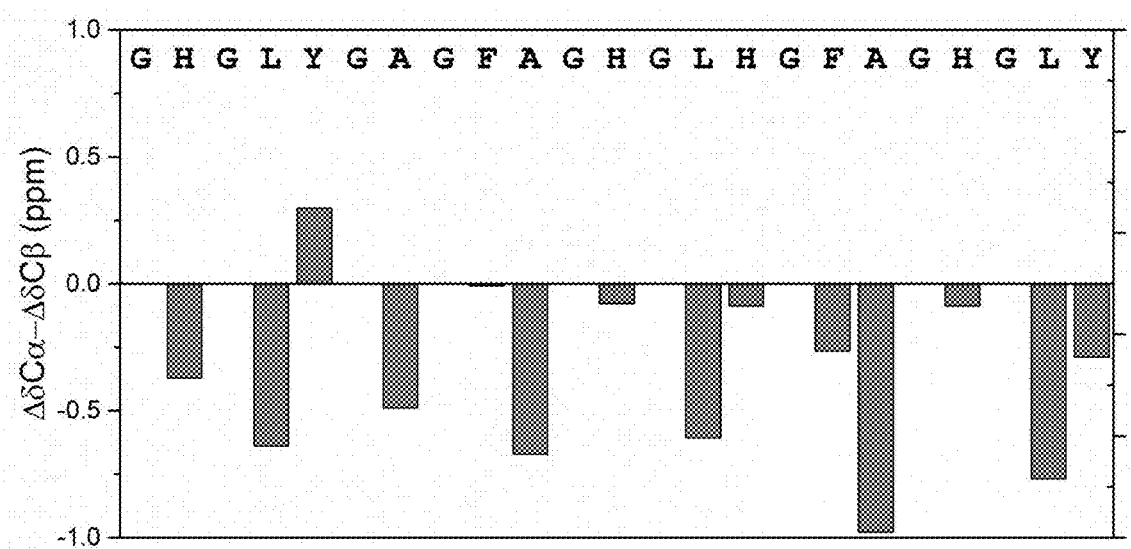
FIG. 28. Residue-specific secondary structure propensity of GY-23 peptide. Secondary shifts ($\Delta\delta C_{\alpha}$-$\Delta\delta C_{\beta}$) indicate lack of secondary structure formation.

These results indicate that His and Tyr residues may be involved in initiating LLPS. To investigate their role in initial steps of aggregation, pH titration experiments on GY-23 have been carried out, where $^1$H-$^{13}$C-HSQC spectra of aliphatic (FIG. 27C) and aromatic (FIG. 27D) side chains of all residues were recorded, as well as the long range $^1$H-$^{15}$N-HMQC spectrum to monitor the protonation state of nitrogen atoms in the imidazole ring of His (FIGS. 27E-F and FIGS. 31A-B). Increasing the pH led to gradual changes of chemical shifts of His $^{13}C_\alpha$ and $^{13}C_\beta$ atoms (upfield in the $^1$H dimension and downfield in the $^{13}$C dimension), as well as $^{13}C_\delta$ and $^{13}C_\epsilon$ atoms of the imidazole ring (FIG. 27D). In addition, resonances assigned to $^{13}C_{0\alpha}$ and $^{13}C_\beta$ of C-terminal Y23 residue significantly shifted upfield in the $^1$H dimension and downfield in the $^{13}$C dimension when the pH raised from 3 to 4, suggesting that the shift is caused by deprotonation of the C-terminal carboxylic group. A major shift of the $^{13}C_\alpha$ cross-peak assigned to G1 was observed as well (FIG. 27C).

$^1$H-$^{13}$C-HSQC spectra of aromatic side chains showed that increasing pH resulted in gradual shifts of resonances assigned to $^{13}C_{\delta2}$ and $^{13}C_{\epsilon1}$ of His residues, which is related to deprotonation of the imidazole ring. Resonances assigned to Tyr and Phe remained unaffected by pH change between 3.3 and 6. However, when the pH increased from 6 to 7 a split of Tyr $^{13}C_\delta$ resonances into two peaks and a minor upfield shift in $^1$H-dimension of all Phe resonances were observed. In addition, chemical shifts of $^{13}C_\zeta$ atoms of Y5 and Y23 at pH 7 were split (FIG. 27D, inset), suggesting that they were in different chemical environments. FIG. 27E shows changes in chemical shifts of $^{15}$N atoms of His imidazole ring during pH titration. At pH 3.3 and 4 all His were fully protonated (since the $^{15}N_{\alpha2}$ and $^{15}N_{\delta1}$ exhibited typical chemical shift values for the protonated state, i.e. 173 ppm and 176 ppm, respectively) (Pelton, J. G., Torchia, D. A., Meadow, N. D. & Roseman, S. (1993) Tautomeric states of the active-site histidines of phosphorylated and unphosphorylated IIIGlc, a signal-transducing protein from *Escherichia coli*, using two-dimensional heteronuclear NMR techniques. Protein Sci. 2, 543-558). Increasing the pH from 4 to 7 led to the gradual deprotonation of the imidazole rings of all His and co-existence of the fully protonated state with two tautomeric forms of the imidazole ring. Critically, it was observed that immediately after raising the pH from 6 to 7, only one of four His residues showed transient stabilization of its ε tautomer state since the $^{15}N_{\delta1}$ peak appeared also at 250 ppm within 5 min after pH adjustment (FIG. 27F). However, the cross-peak intensity was significantly reduced 30 min following pH adjustment (FIGS. 31A,B), indicating that only one His residue underwent transient stabilization of the tautomeric state, which is likely caused by hydrogen bonding. Since at pH 7 chemical shifts of Tyr $^{13}C_\zeta$ atoms were also shifted, this suggests that hydrogen bond interaction is taking place between the hydroxyl group of Tyr and $^{15}N_{\delta1}$ of His, which may be the first step in the oligomerization cascade. Moreover, 3D $^{15}$N- and $^{13}$C-NOESY experiments with long mixing times were carried out and NOEs between His and Tyr were not observed, further supporting the transient character of the Tyr/His interaction.

GY-23 Peptide Shows Partially Ordered Structures after LLPS

Although IDPs do not exhibit well-defined tertiary structures, there are evidences that coacervate micro-droplets of IDPs contain short-range order[10]. To further study the coacervation at the nanostructural level and assess whether GY-23 coacervate micro-droplets exhibited such internal ordering, we investigated their structural features using Small Angle X-ray Scattering (SAXS). Scattering profiles of GY-23 in acetic acid (pH 3.3) before LLPS and in the coacervate buffer (pH 7.0) after LLPS (both the coacervate and the coexisting dilute phases) are presented in FIG. 30A and were very distinct from each other. The scattering intensity of GY-23 in acetic acid and of the dilute phase after centrifugation had a very low signal-to-noise ratio. Nevertheless, for GY-23 in acetic acid, a weak low-q upturn with an indication of a broad correlation peak between 0.3 and 2 nm$^{-1}$ was observed, which may be attributed to nanometer-sized peptide oligomers. Dynamic light scattering (DLS) analysis of the peptide in acetic acid (FIG. 30C) indicated the presence of structures with a hydrodynamic diameter ($D_H$) of ca. 8 nm, corroborating the presence of small oligomeric units (assuming $D_H$ on the order of 4-8 nm for the 23 residue-long monomeric peptide). As expected, $D_H$ increased drastically to around 50 nm at pH 7.0 due to initiation of LLPS.

Figure 32A:
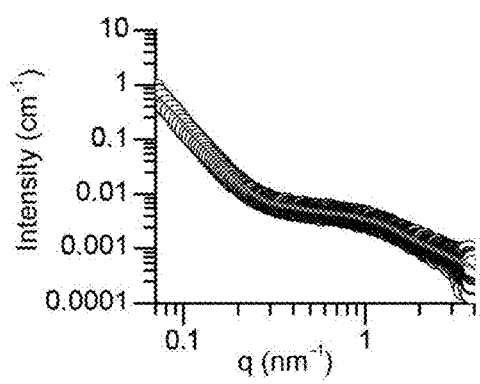
FIGS. 32A-32B. Additional SAXS experiments with a synchrotron x-ray source. (A) SAXS experimental curve. The calculated fit for the peptide assemblies from the IFT method is presented as the full red line. (B) Corresponding p(r) profile calculated from the SAXS data in (A) using Eq. 1 (materials and methods). The arrow and the zoom-in view (inset) indicates that coacervate micro-droplets contain self-assembled sub-units of ca. 2 nm, which may be attributed to peptide oligomeric units.
Figure 32B:
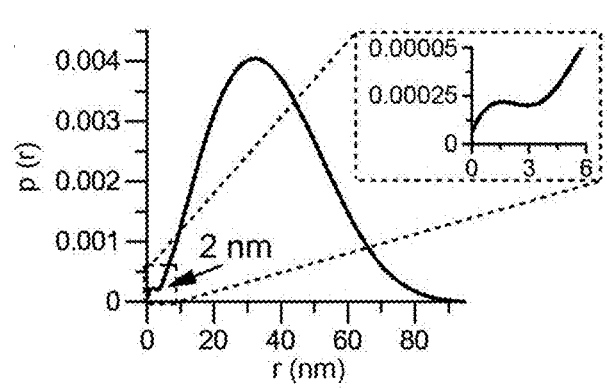

In contrast, the scattering profile of GY-23 in the coacervate phase (FIG. 30A) indicated the presence of much larger peptide aggregates in the form of coacervate micro-droplets with overall dimensions that exceeded the resolution limit of the SAXS set-up. An indication of a broad correlation peak in the q-region of ~1.5 nm$^{-1}$ suggested structural features from peptide self-assemblies within the coacervate micro-droplets. The low signal-to-noise ratio in this q-region makes it difficult to analyze this feature in detail (however this correlation peak was confirmed using a more intense synchrotron x-ray source, FIGS. 32A-B). At q<1 nm$^{-1}$, on the other hand, the scattering curve showed an approximate power-law dependence over at least an order of magnitude in the q-range, indicating fractal scattering from the dense peptide assemblies within the coacervate phase.

Figure 30B:
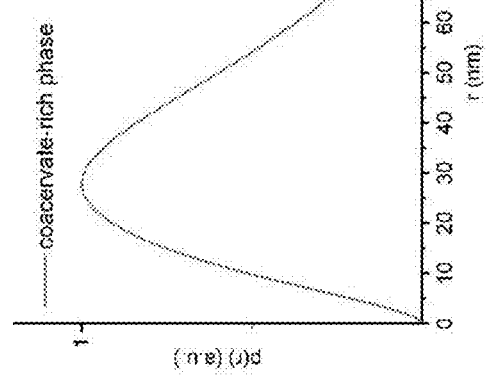
Figure 30C:
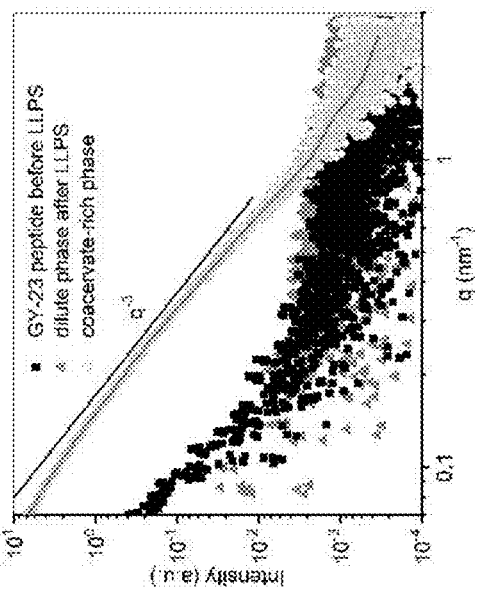
Figure 31A:
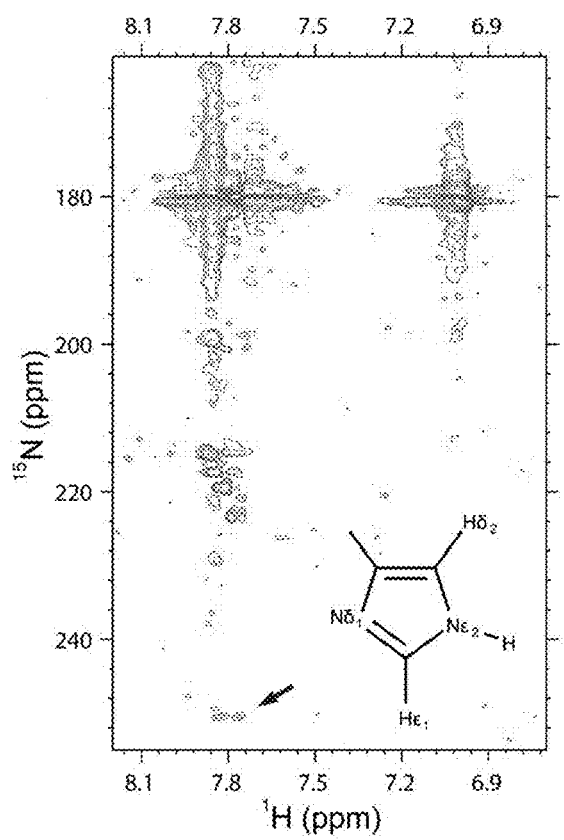
FIGS. 31A-31B. Time-dependent comparison of the long-range $^{1}$H-$^{15}$N-HMQC spectra of His imidazole ring. (A) Spectrum acquired within 5 min after pH adjustment to 7.0 (point of coacervation). (B) Spectrum acquired within 30 min after pH adjustment. The characteristic resonance for ε-tautomer at approximately 250 ppm in the N-dimension (marked with the arrow in panel (A) is present in the time frame of a few minutes shortly after pH adjustment to the coacervation point, indicating the transient nature of the interaction. Spectra acquired at T=298° K. and a peptide concentration of 1.5 mM.
Figure 31B:
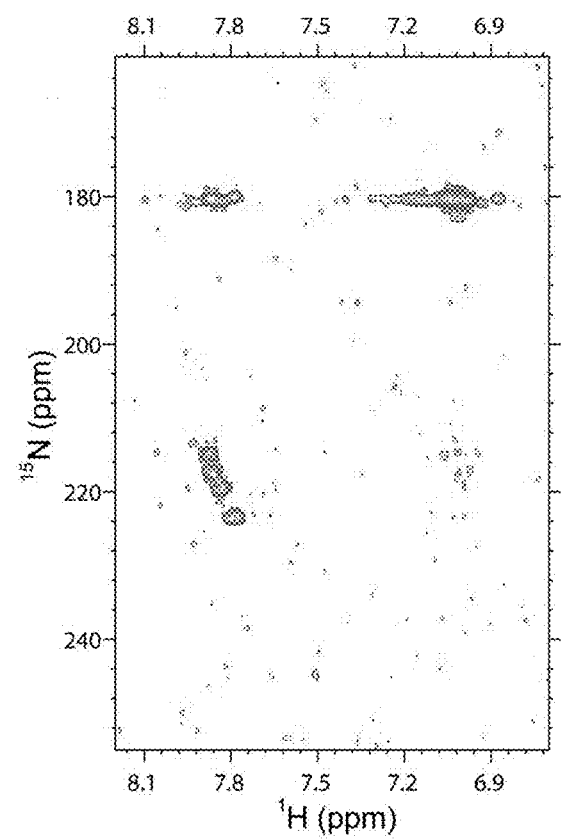

To further investigate the internal structure of coacervate micro-droplets, the pair distance distribution function p(r) was calculated from the SAXS curve using the indirect Fourier transformation (IFT) method (FIG. 30B). The p(r) function reflected large peptide aggregates in the micro-droplets with dimensions well-beyond the resolution limit of the SAXS set-up in this study (around 50 nm in real space). Hence, the p(r) was mathematically forced to 0 at r around 100 nm, but this does not represent the overall dimension of the coacervate micro-droplets. The analysis of the corresponding SAXS data of the coacervate droplets in buffer at a higher signal-to-noise ratio, recorded at the synchrotron, is presented in the FIGS. 32A-B. The results indicated that the coacervates micro-droplets contained nanostructural features of ca. 2 nm. These features are most likely attributed to oligomeric peptides forming the internal domain structures of the coacervate micro-droplets.

Analysis of Tyrosine-Tyrosine Interactions by ssNMR

Since site-directed mutagenesis experiments suggested a critical role of Tyr residues, GY-23 containing uniformly labeled ($^{13}$C and $^{15}$N) Tyr residues (Y5 and Y23) were synthesized and possible Tyr-Tyr interactions in the condensed coacervate phase by solid-state NMR were analyzed. FIGS. 33A-B show a comparison between 1D direct and $^1$H-$^{13}$C CP-based carbon spectra. Both spectra contained relatively broad lines, indicating that Try residues were present in heterogeneous conformational environments since multiple peaks for each Tyr carbon were observed. For example, $^{13}C_\alpha$ resonances at 53.0, 57.5, 58.7 ppm, and carbonyl $^{13}$C at 173.3, 176.8, 180.8 ppm, respectively, were detected. The presence of strong signals in CP-based spectrum indicated that most of Tyr moieties were locked in the rigid structure with high dipolar order. No extra sharp peak was observed in the direct-polarization $^{13}$C spectrum compared with the CP-based spectrum, indicating the absence of highly flexible Tyr residue, hence further supporting that Try residues were rigidly locked. Two-dimensional $^{13}$C-$^{13}$C Dipolar Assisted Rotational Resonance (DARR) (FIG. 33C) shows correlations between the two Tyr residues of the peptide, demonstrating that they interacted with each other. Moreover, the DARR data clearly indicated that Tyr residues were in heterogeneous chemical environments, implying clustering of Tyr residues close to each other. Tyr-Tyr direct interactions were also corroborated by the heteronuclear correlation (HETCOR) spectrum (FIG. 33D), which shows correlations between aliphatic and aromatic carbon atoms of Tyr attributed to the stacked clustering of two or more tyrosine side groups.

Example 3: Doxorubicin (Dox)-Loaded Magnetic Coacervates for Chemotherapy

Dox-Loaded Magnetic Coacervates

Figure 36A:
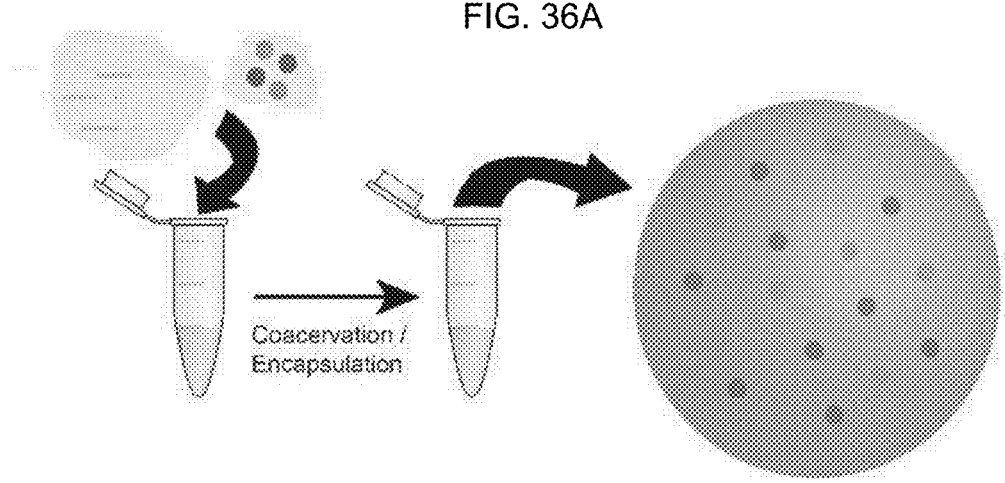
FIGS. 36A-36B. (A) Illustration of the coacervation and Doxorubicin (Dox)+magnetic nanoparticles (MNP) encapsulation process. Dox and MNP are first added to buffer, followed by additional of peptide stock solution to initiate coacervation and encapsulation. (B) Dox+MNP loaded coacervates can be directed away from health tissue and accumulated at tumour site using directional magnetic field. Once the coacervates reaches the target site, heat generated from MNP under alternating magnetic field (magnetic hyperthermia) induces the release of Dox. Heat generated can also enhance the cytotoxic activity of Dox.

Dox and MNP are first added to buffer, followed by additional of peptide stock solution to initiate coacervation and encapsulation (FIG. 36A).

Figure 36B:
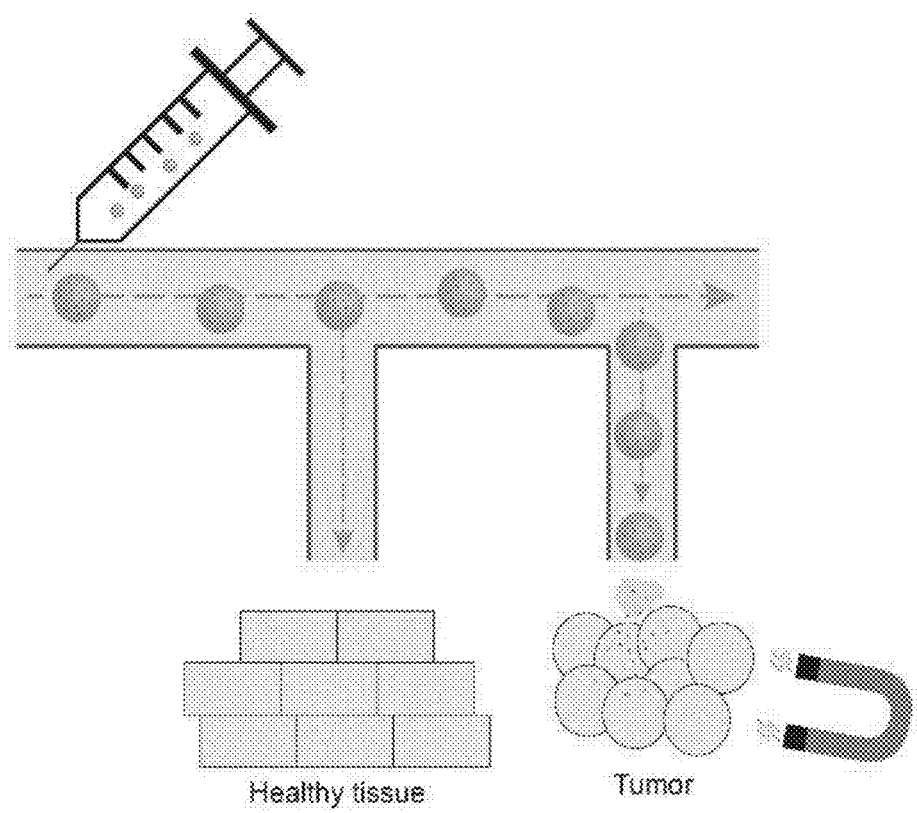

Dox+MNP loaded coacervates can be directed away from health tissue and accumulated at tumour site using directional magnetic field. Once the coacervates reach the target site, heat generated from MNP under alternating magnetic field (magnetic hyperthermia) induces the release of Dox. Heat generated can also enhance the cytotoxic activity of Dox (FIG. 36B).

Heat Dissociation of Coacervates

One of the best known proteins that can be used for coacervates is tropoelastin. However, tropoelastin is not suitable in this case because it requires heat to drive coacervation. The level of tropoelastin coacervation will increase with magnetic hyperthermia, making release of therapeutics difficult.

Figure 37:
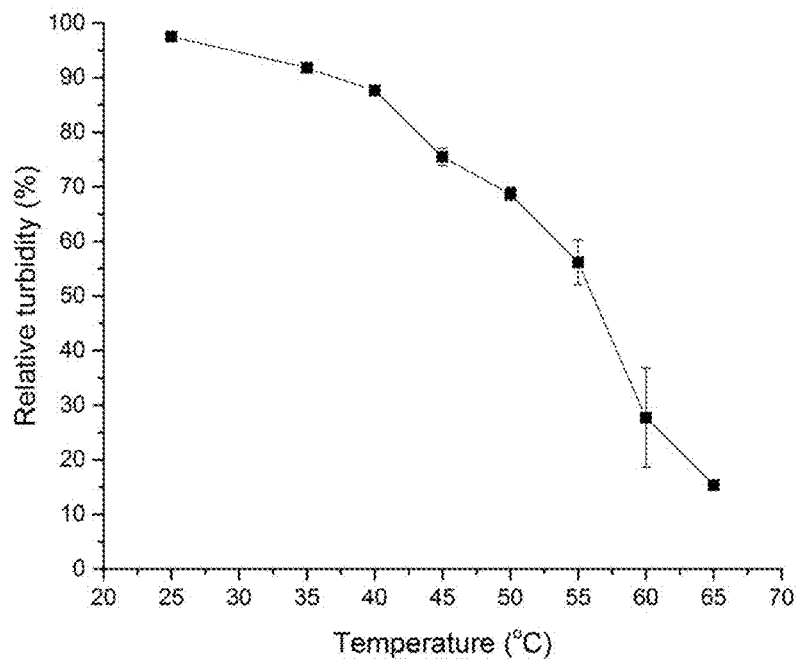
FIG. 37. Dissociation of DgHBP-2 peptide coacervates (1 mg/mL) at different temperature. This is to simulate the dissociation of coacervates by magnetic hyperthermia. Relative turbidity of coacervates decreased with increasing temperature. A rapid decrease was seen at temperature higher than 40° C. (magnetic hyperthermia for chemotherapy is usually between 42° C. to 48° C.).

DgHBP-2 peptide coacervates dissociate upon heating. Therapeutics that are loaded inside DgHBP-2 peptide coacervates are released, which is stimulated by magnetic hyperthermia. By controlling the duration of magnetic hyperthermia, the rate of therapeutics release can be controlled (FIG. 37).

Dox+MNP Loaded Coacervates

Figure 38:
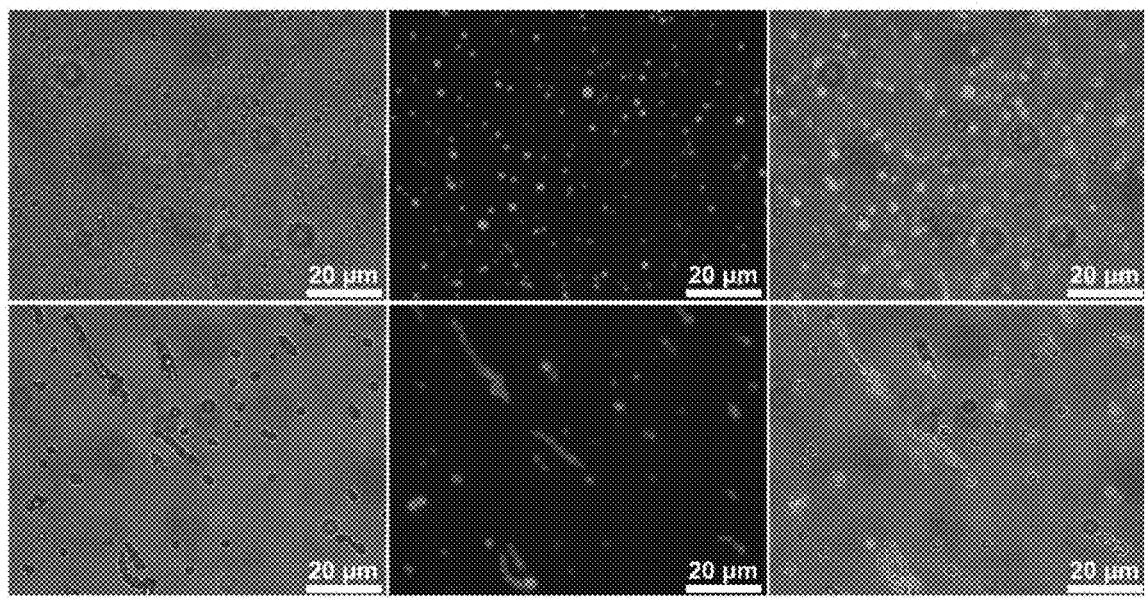
FIG. 38. Microscopy images of DgHBP-2 peptide coacervates loaded with Dox and MNP. Top panel: without magnetic field; Bottom panel: with magnetic field. DgHBP-2 peptide coacervates can be loaded with both Dox+MNP and are magnetic-responsive.

Dox has a natural red fluorescence, allowing the detection of Dox under fluorescence microscopy. From the microscopy images, the co-localisation of red fluorescence and droplets-like coacervates indicated that Dox has been encapsulated successfully (FIG. 38).

Without magnetic field, Dox+MNP loaded coacervates were randomly deposited to the glass slides. Upon exposure to magnetic field, the coacervates lined themselves along the magnetic field and formed strings of coacervates (FIG. 38).

Encapsulation Efficiency of Different Concentrations of Dox by DgHBP-2-Peptide Coacervates.

Only ~40% of Dox is being encapsulated (FIG. 39), therefore unencapsulated Dox (60%) need to wash off. However, once coacervates are centrifuged, they cannot be retrieved (stick to Eppendorf tube after centrifugation). To wash off excess Dox, coacervates have to be first stabilised. Stabilisation can be done by crosslinking the coacervates.

One possible reason for the difference in encapsulation efficiency of insulin (>99%) and Dox (~40) could be due to charge difference. Insulin has an isoelectric point of 5.4 and is negatively charged at physiological pH. Dox has a pKa value of ~8.46 and is positively charge at physiological pH. However, the effect of charge on encapsulation in coacervates is currently unknown and remains to be verified.

Covalent Crosslinking of Catechol

Figures 39, 40:
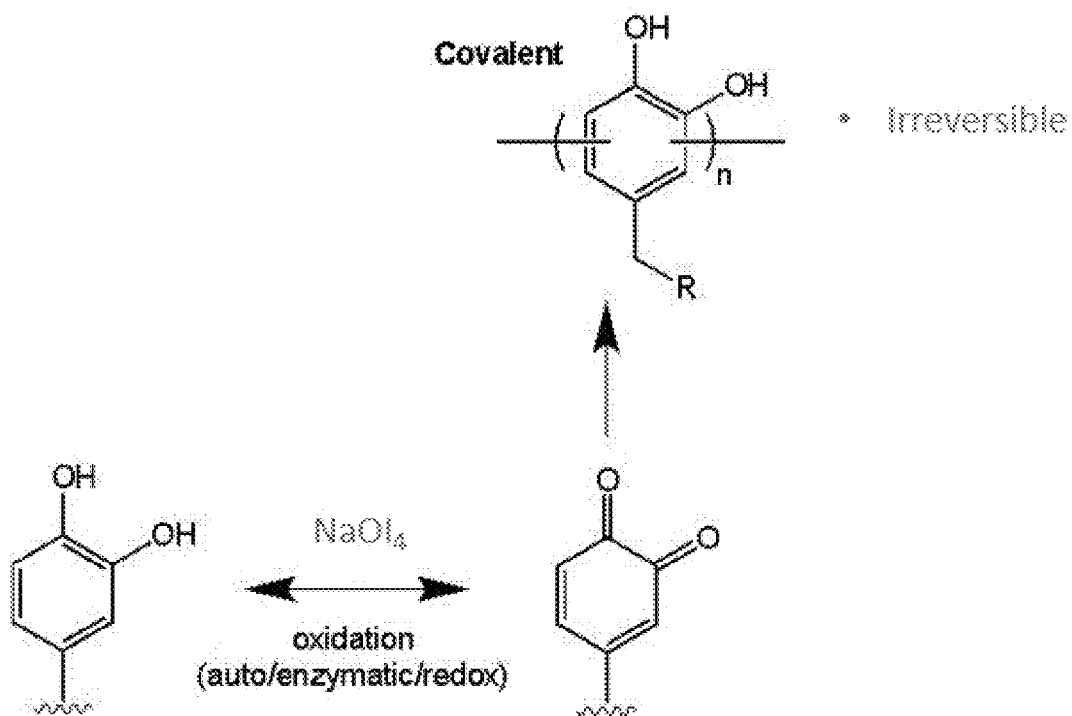
FIG. 39. Encapsulation efficiency of different concentration of Doxorubicin by DgHBP-2-peptide coacervates.
FIG. 40. Covalent crosslinking of catechol.

Catechols can be oxidised to quinones for covalent crosslinking. There are two main methods of oxidation: chemically and enzymatically. A common chemical oxidant, sodium periodate (NaIO4) was used in this project to convert catechols to quinones (FIG. 40). Quinone are extremely reactive and can react with different chemical groups in the peptide e.g. amines and imidazoles to form covalent bonds.

4-Methylcatechol (MC)/NaIO4 Crosslinked Coacervates

The co-localisation of red fluorescence and 4-MC/NaIO$_4$ coacervates indicated that Dox still retains within the coacervates after crosslinking. Under a directional magnetic field, the 4-MC/NaIO$_4$ coacervates lined themselves along the magnetic field and formed strings of coacervates. These results show that by using a magnetic field, the coacervates can be directed towards tumour site or to accumulate at tumour site and away from healthy tissue. The level of crosslinking can be fine tuned between stabilisation and Dox release by changing 4-methylcatechol concentration (FIGS. 41A-D).

Heat Induced Release of Dox

The rate of Dox release at different temperatures from 4-MC/NaIO$_4$ crosslinked coacervates was measured. Rate of Dox release at 37° C. was measured to determine the leakiness of coacervates in normal body temperature. Rate of Dox release at 42° C. and 45° C. was assessed to simulate magnetic hyperthermia temperatures. From the data, the rate of release at 42° C. and 45° C. is much higher compared to 25° C. and 37° C. This confirms that release of Dox can be triggered by heating from magnetic hyperthermia. Without magnetic hyperthermia, the release of Dox is minimum (FIGS. 42A-B).

Cell Viability Assay (MTT Assay)

Figure 43A:
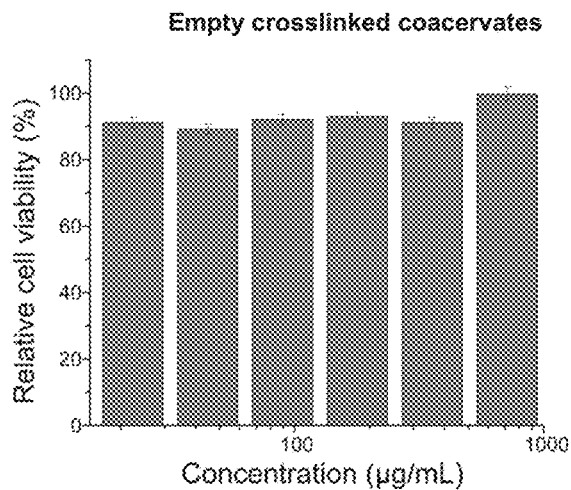
FIGS. 43A-43B MTT assay is a colorimetric assay for assessing cell metabolic activity, using metabolic rate to infer cell survivability. (A) 4-Methylcatechol/NaIO$_4$ crosslinked coacervates (B), Dox-loaded 4-methylcatechol/NaIO$_4$ crosslinked coacervates (MTT:(3-(4,5-dimethylthiazolyl-2)-2,5-diphenyltetrazolium bromide), NIH3T3 fibroblast cells).
Figure 43B:
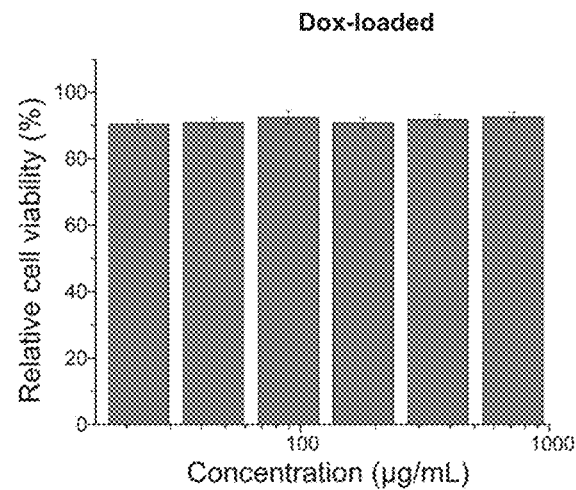

NaIO$_4$ and 4-MC are toxic chemicals that may be harmful to cells. After crosslinking, excess unreacted chemicals must be washed off. MTT assay was used to test for toxicity of crosslinked coacervates and remnants of toxic chemicals. The results reveal that the crosslinked coacervates by itself were nontoxic and excess chemicals have been removed after crosslinking (FIG. 43A). This shows that Dox leakage from coacervates is minimum and does not affect the viability of cells (FIG. 43B) (MTT: (3-(4, 5-dimethylthiazolyl-2)-2, 5-diphenyltetrazolium bromide)).

Figure 44A:
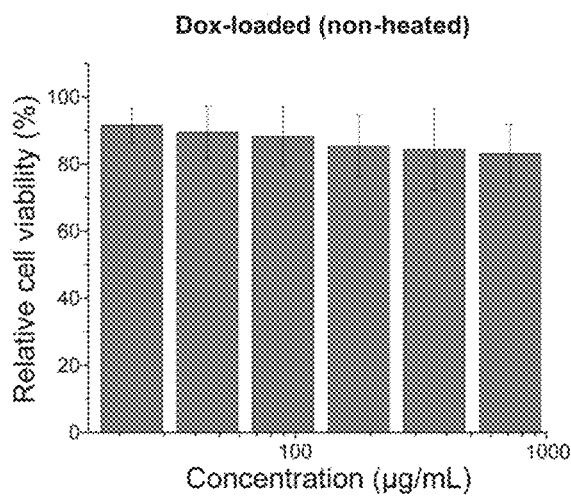
FIGS. 44A-44B. Relative cell viability of Dox-loaded 4-MC/NaIO$_4$ coacervates treated HEPG2 cells. After heating, Dox is released from the coacervates and reduces the viability of HEPG2 cells. (A) Dox-loaded coacervates in PBS without heat treatment. (B) Dox-loaded coacervates in PBS were heated at 45° C. for 30 min, before adding to cells (measurements at 570 nm).
Figure 44B:
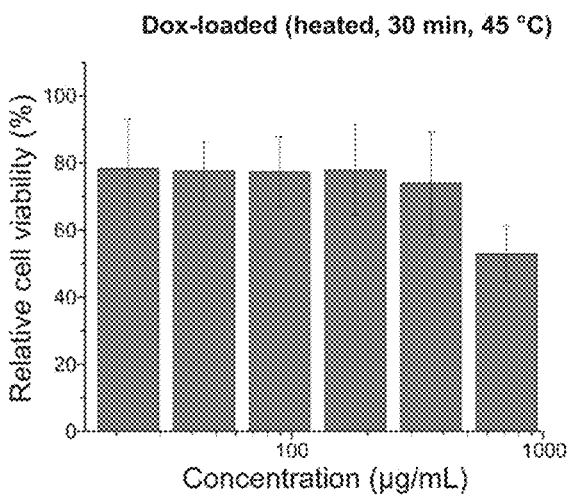

Dox loaded coacervates were incubated with HEPG2 liver cancer cells to assess its cytotoxic properties. FIG. 44A: Dox-loaded coacervates in PBS without heat treatment, FIG. 44B: Dox-loaded coacervates in PBS were heated at 45° C. for 30 min, before adding to cells (measurement at 570 nm). This heating is to induce the release of Dox. The relative cell viability of non-heated coacervates treated cells is more than 80%, whereas relative cell viability of heated coacervates treated cells decrease to ~50%. This indicates that Dox still retains its cytotoxic properties after its encapsulation and release from coacervates. Relative cell viability of heated coacervates treated cells increases as the concentration of coacervates decreases. This is because as the concentration of released Dox decreases, the cytotoxic properties of Dox also decrease.

GFP Loaded Coacervates

Figure 45A:
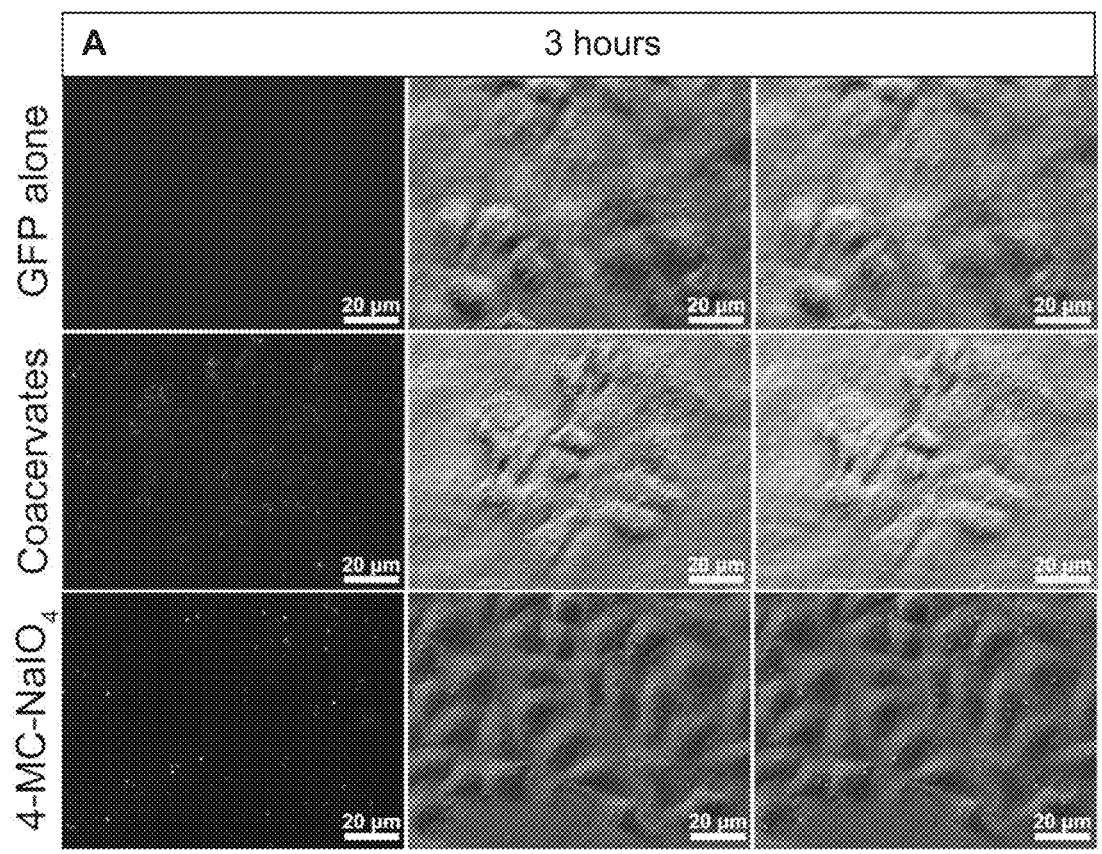
FIGS. 45A-45C. GFP-loaded coacervates (C) were used to determine if coacervates can enter HEPG2 liver cancer cells. Within 3 hours of incubation (A), most of the GFP-loaded coacervates co-localized with the HEPG2 cells. After 24 hours of incubation (B), GFP-loaded coacervates were still visible. The coacervates seem to have merged and became bigger compared to 3 hour incubation.
Figure 45B:
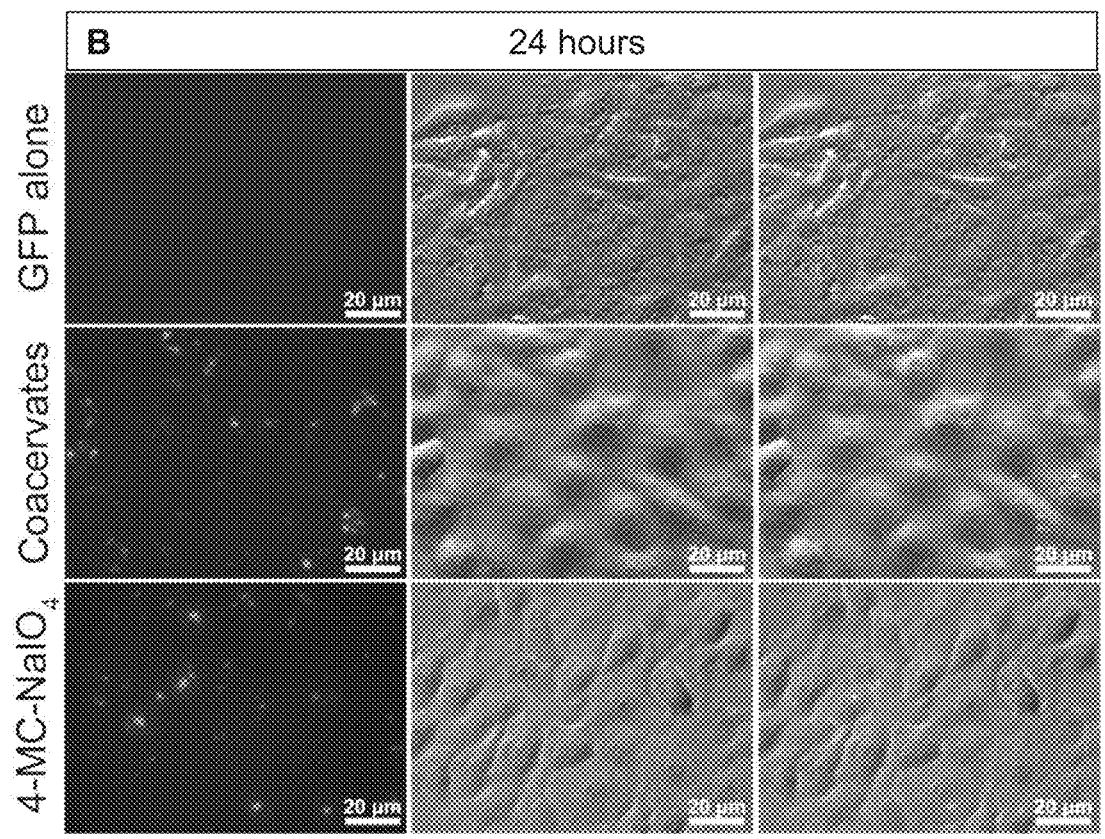
Figure 45C:
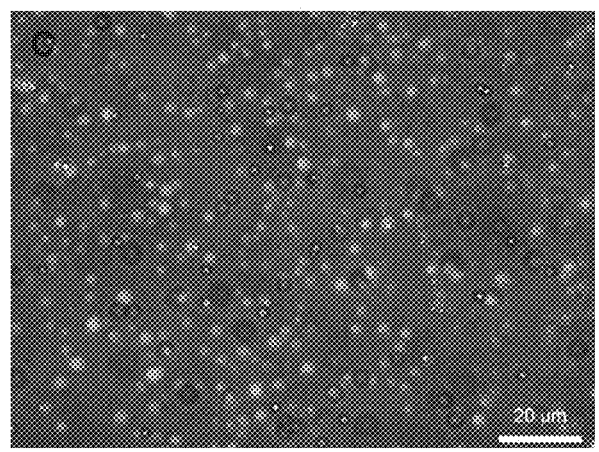

Despite the size of coacervates (~1 µm), they were able to enter HepG2 cells within 3 hours and remained stable inside the cells for at least 24 hours. The coacervates were not broken down in lysosomes or by other enzymes present in cytosol. They were also unlikely to be trapped in organelles like endosomes, as coacervates were still able to coalescence. The stability of coacervates inside the cells implies that any Dox will remain encapsulated until magnetic hyperthermia occurs. The release of Dox can be controlled in a more precise manner (FIGS. 45A-C).

Endosomes Staining (Endocytosis)

Figure 46:
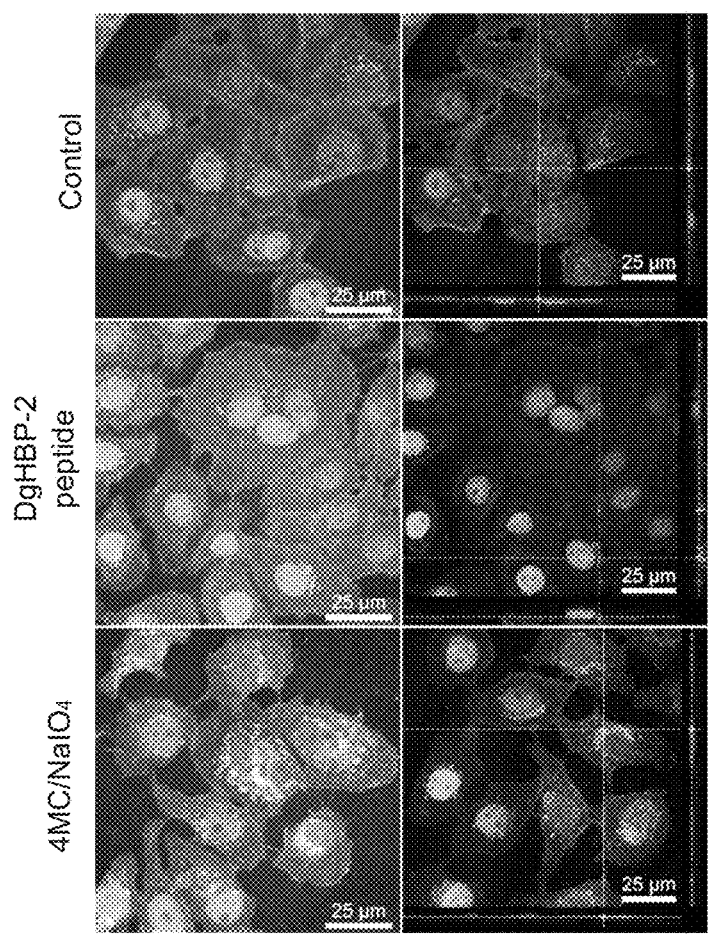
FIG. 46. Endosomal staining of GFP-loaded coacervates treated HEPG2 cells. Left column: z-stack merged image and right column: orthographic view. Green and red fluorescence does not co-localize, indicating that coacervates were not taken up through endocytosis process (Lysotracker: GFP (green) (coacervates), Hoechst 33342 (blue) (nucleus), LysoTracker Red DND-99 (red) (endosomes/lysosomes), wheat germ agglutinin (yellow-orange) (cell membrane)).

Endocytosis is a kind of active cell uptake process where particles e.g. parts of cells, or nutrients are taken into cell. During this internalisation process, cell membrane invagination occurs to form a membrane-bound compartment called endosomes. Since endocytosis is one of the main cell uptake processes, endosomes staining is done to determine if coacervates are inside endosomes after cell uptake. Lysotracker is a dye that stains acidified endosomes. Green fluorescence of GFP does not co-localize with the red fluorescence of Lysotracker. These results showed that coacervates are not in the endosomes, therefore they are unlikely to enter through endocytosis. Another possibility is that the coacervates enter cells through endocytosis pathway, but escape from the endosomes before the latter fuses with lysosomes. The orthographic views reveal that coacervates were inside cells and not sticking to the cell membrane (FIG. 46).

Figure 47:
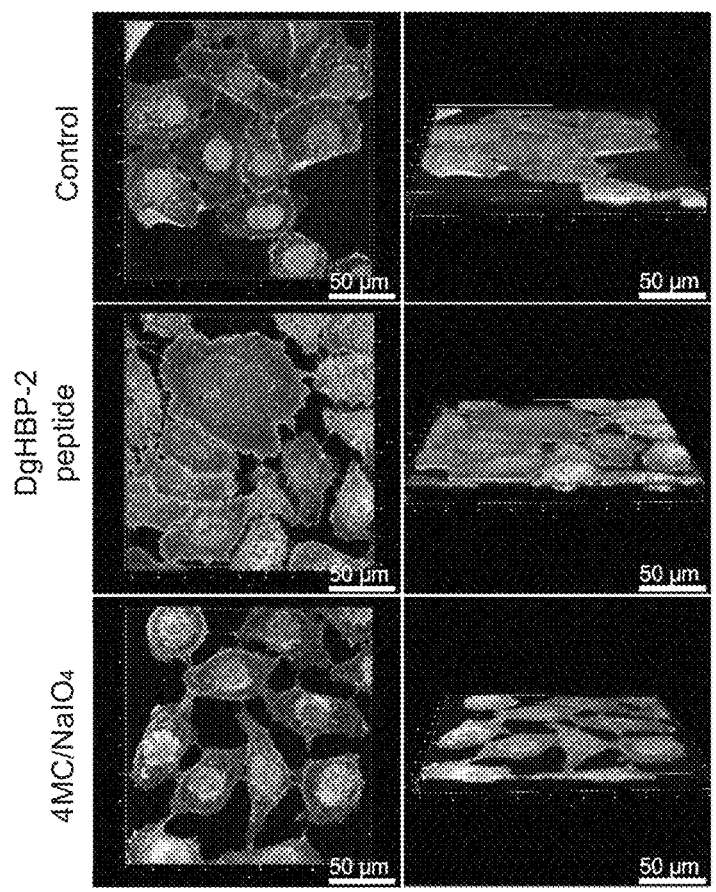
FIG. 47. 3D image GFP-loaded coacervates treated HEPG2 cells. The GFP-loaded coacervates were located between the cell membrane and nucleus, indicating that the coacervates had successfully entered the cell (Lysotracker: GFP (green) (coacervates), Hoechst 33342 (blue) (nucleus), LysoTracker Red DND-99 (red) (endosomes/lysosomes), wheat germ agglutinin (yellow-orange) (cell membrane)).

The GFP-loaded coacervates were located between the cell membrane and nucleus, indicating that the coacervates had successfully entered the cell (3D image GFP-loaded coacervates treated HEPG2 cells, FIG. 47).

Heating of Dox+MNP Loaded Coacervates by Alternating Magnetic Field (AMF)

Figure 48:
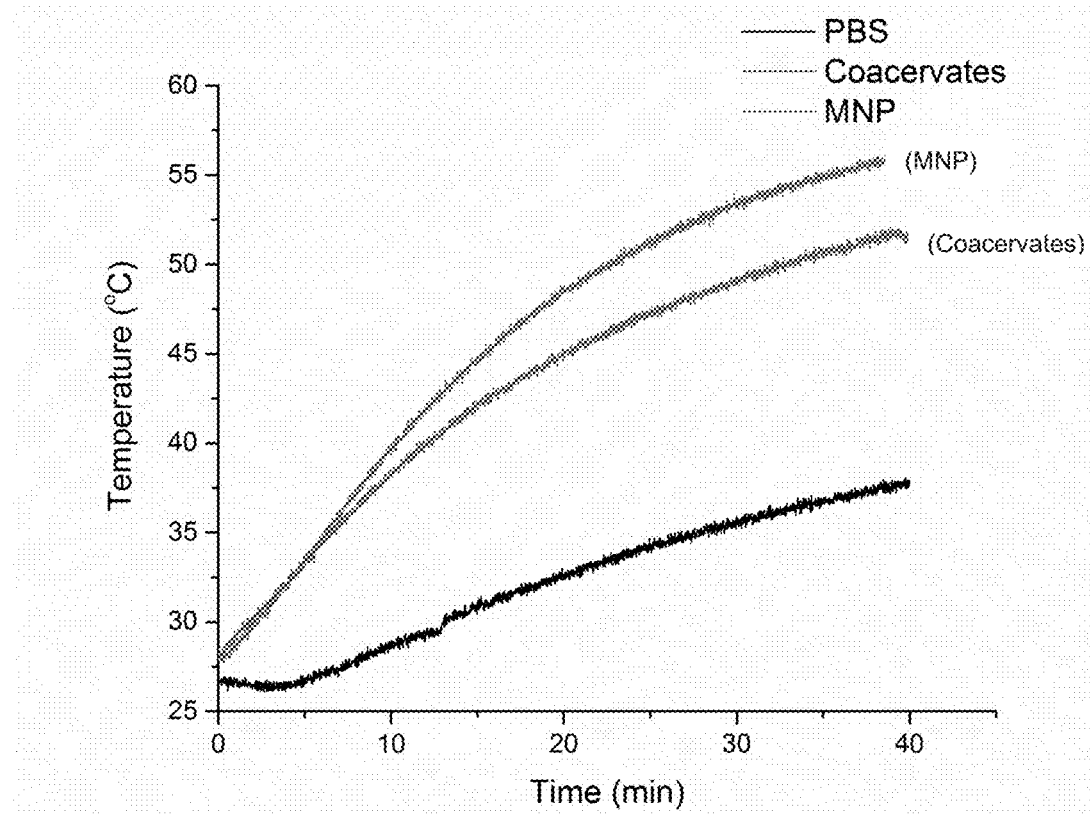
FIG. 48. Heating of Dox+MNP loaded coacervates by alternating magnetic field (AMF). Under AMF, MNP and Dox+MNP loaded coacervates were heated to more than 50° C., whereas PBS (without any MNP) was heated to only 38° C.

Under alternating magnetic field, MNP and Dox+MNP loaded coacervates were heated to more than 50° C., whereas PBS (without any MNP) was heated to only 38° C. (FIG. 48). This slight increase in temperature for PBS was due to the heat generated from the AMF generator.

MHT Triggered Release of Dox

Figure 49A:
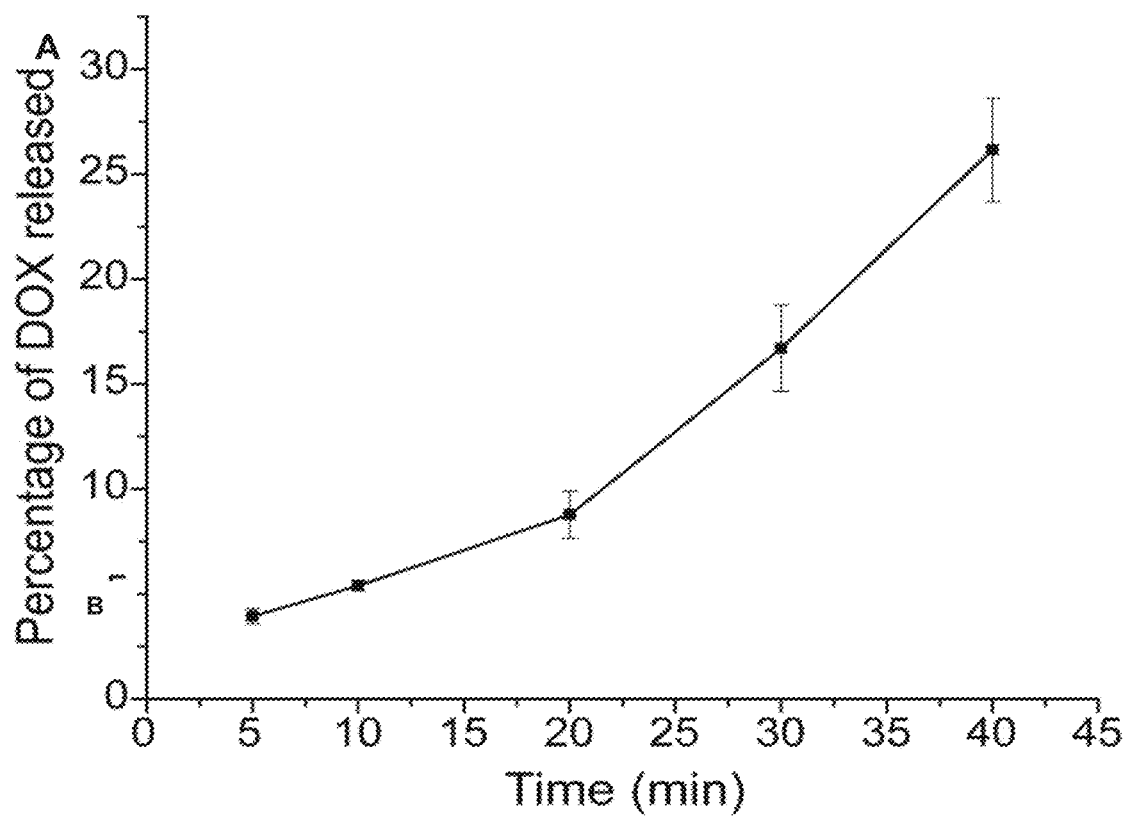
FIGS. 49A-49B. Release of Dox from Dox+MNP loaded, 4-MC/NaIO$_4$ coacervates under alternating magnetic field (AMF). (A) Release of Dox under AMF over 40 min. (B) Pulse release of Dox over 5 times of AMF treatment, with each treatment 20 mins long to reach a temperature of 45° C.
Figure 49B:
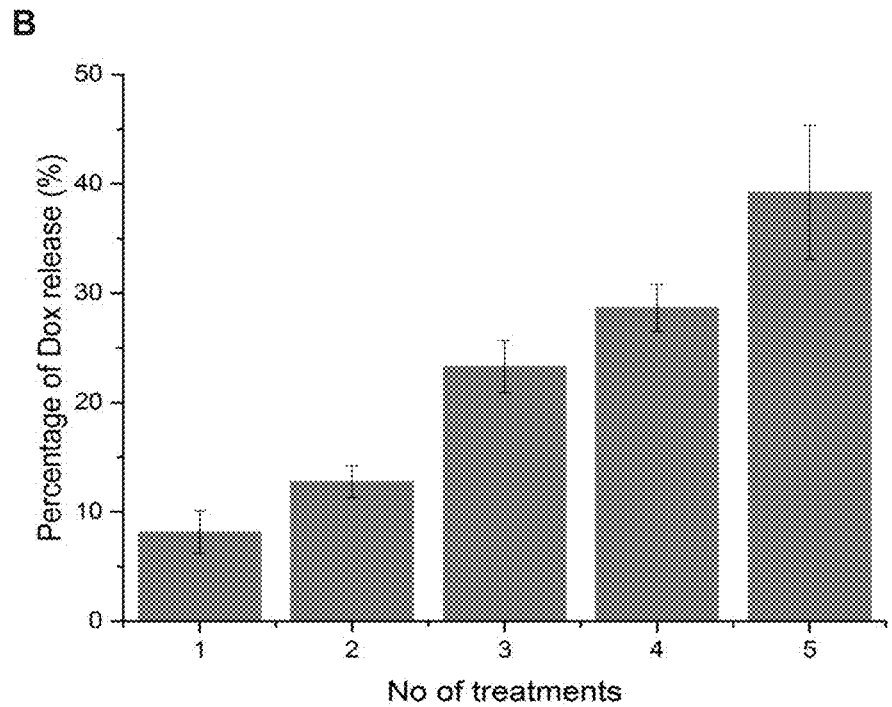

Dox+MNP loaded, 4-MC/NaIO$_4$ coacervates were placed in alternating magnetic field to induce magnetic hyperthermia. The heat from magnetic hyperthermia is used to trigger the release of Dox. From the data, the amount of Dox released increases with the duration of magnetic hyperthermia. At 40 min, ~25% of Dox in coacervates were released. Since not all the Dox is released, multiple treatments can be done with single injection (FIGS. 49A-B).

Preliminary Animal Studies
In Vivo Work-Mouse (Biodistribution)

Figure 50A:
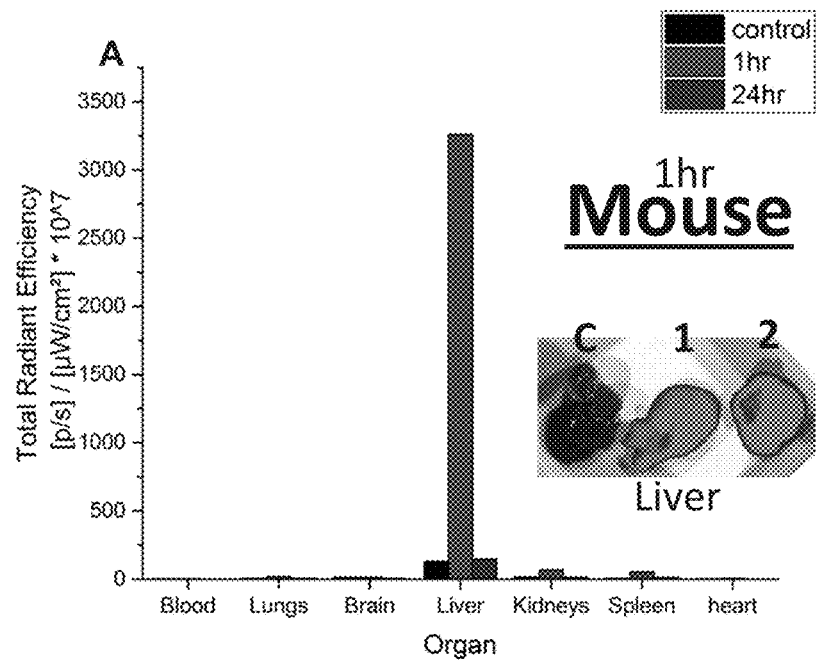
Figure 50B:
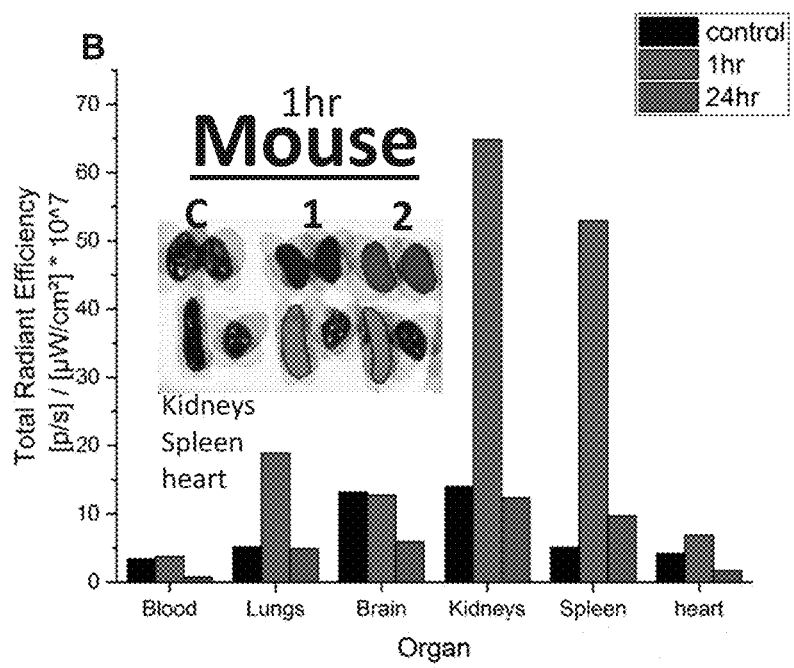
Figure 50C:
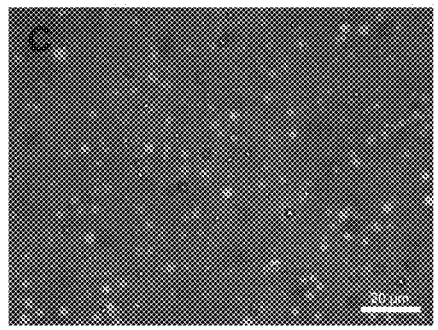
Figure 50D:
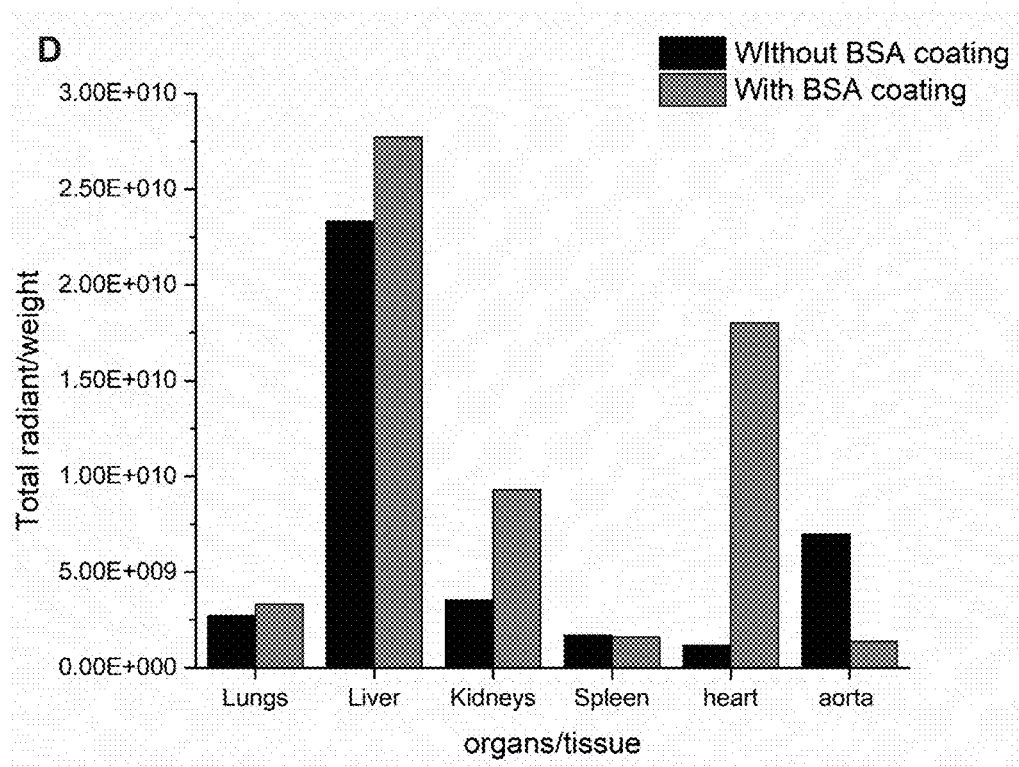

Free cy5.5 dye is clear mainly through kidneys. Since highest radiant was observed in liver, this suggests that the coacervates are stable in vivo as the cy5.5 dye still remained inside the coacervates. The rapid clearance of coacervates by liver can be due to the size of coacervates (BL6 female mice: FIGS. 50A, B, C, apolipoprotein E knockout (APOE KO) mouse: FIGS. 50D and E). The APOE KO mice do not have apolipoprotein E in their body and are more susceptible to plaque formation in their aorta. The first set of mouse work data (FIGS. 49A and 49B) used wildtype mice whereas the second set of mouse work (FIGS. 49D and 49E) used APOE KO mice. The reason for switch in the type of mice used was to test if the coacervates could attached to the plaques for prospective plaque-targeted delivery therapies.

Figure 51:
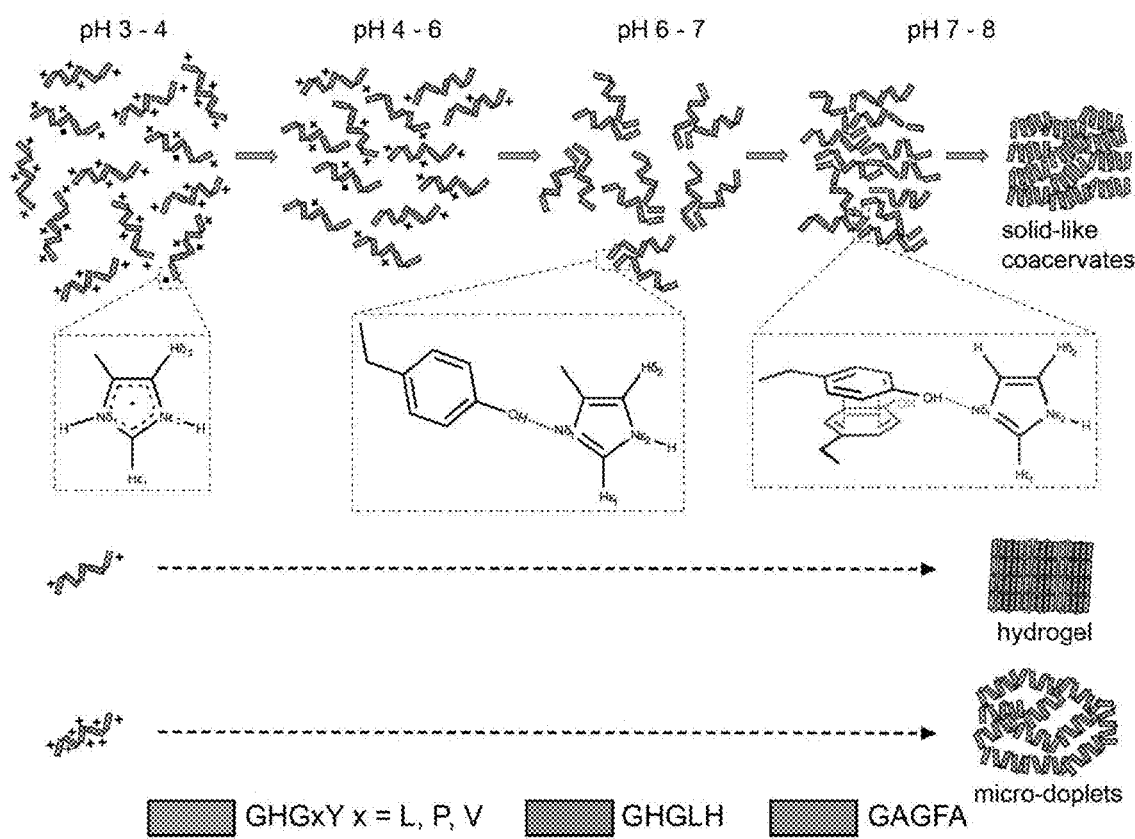
FIG. 51. Proposed model of pH-dependent LLPS of HBP-derived peptides. At pH 3-4 His residues are protonated, and the peptides form soluble oligomeric units due to electrostatic repulsion between positively charged His side chains. At pH 4-6 gradual deprotonation of His residues occurs, repulsive forces are weaker but still strong enough to keep the peptide oligomers soluble. At pH 6-7 transient interactions take place between His and Tyr residues located within GHGxY repeats leading to specific peptide-peptide interactions that act as nuclei for LLPS. Further increase of pH above 7 leads to Tyr-Tyr inter-molecular stacking and intra-molecular interaction of hydrophobic residues that all together trigger LLPS and the formation of micro-droplets. If the central domain of the peptide is enriched with the hydrophobic motif GAGFA or with the His-rich motif GHGLH, LLPS is driven by the same sequence of molecular events but eventually leads to the formation of either a hydrogel or coacervate micro-droplets, respectively.

There has been growing recognition that LLPS is involved inside cells via membrane-less organelles as well as in the processing of extra-cellular load bearing structures and bioadhesives of various organisms. However, sequence motifs and associated inter- and intra-molecular interactions driving phase separation remain sparsely understood. It was shown that phase separation of DgHBPs is mediated though specific GHGXY modular repeats that must be arranged in a specific configuration. It was also shown that the morphology and rheology of separated phases can be tuned from dispersed coacervate micro-droplets to hydrogels by incorporating hydrophobic GAGFA repeats in a peptide sequence. Based on solution-state NMR measurements, LLPS of DgHBPs is a multi-step process initially triggered by deprotonation of His residues upon pH increase, followed by stabilization of His ε tautomeric state by transient hydrogen bonding with OH group of Tyr residues. Without wishing to be bound to any particular hypothesis, it is believed that these events eventually promote hydrophobic intermolecular interactions largely controlled by Tyr residues, as well as hydrophobic collapse of the peptides' central domains as schematically illustrated in FIG. 51. Investigations of the GY-23 coacervate phase by SAXS and solid-state NMR showed that it possesses partial internal ordering in the nanometer range that is stabilized by hydrophobic interactions, in particular clustering of Tyr residues. These findings concur with earlier biophysical studies on the full length DgHBPs showing that a certain degree of protein folding is achieved in the coacervate state (Cai, H. et al. (2017) Soft Matter 13, 7740-7752).

There are a few reports providing a full picture of molecular events leading to LLPS of IDPs (Reichheld et al. (2017) Proc. Natl. Acad. Sci. 114, E4408-E4415). The study by Reichheld et al. showed that LLPS of ELPs is an entropy-driven mechanism mediated by transient interactions between the highly dynamic and disordered hydrophobic domains of ELPs. Hydrophobic interactions led to gradual exclusion of water and salt molecules, eventually allowing chemical crosslinking of ELP monomers to form an elastic network. Without wishing to be bound to any particular theory, it is assumed that a similar process takes place during LLPS of DgHBPs. According to the current model of squid beak processing, DgHBPs coacervates condensate and dehydrate chitin nanofiber scaffold and finally undergo chemical crosslinking (Tan, Y. et al. (2015) Nat. Chem. Biol. 11, 488-495; Miserez et al. (2010) J. Biol. Chem. 285, 38115-38124). Therefore, the partial ordering of the DgHBP coacervates that was observed by SAXS and solid-state NMR may be an intermediate step before the final crosslinking taking place in vivo.

There is increasing evidence that aromatic interactions are critical to drive LLPS and stabilize phase separated structures. Another model of LLPS that involves aromatic residues is based on π-cation interactions between positively charged residues (Arg or Lys) and aromatic moieties of Phe or Tyr. Herein, it is shown that Tyr-Tyr interactions are critical to stabilize the biopolymer-rich phase after phase separation, but that they must first be activated through interactions with His side-groups in a pH-dependent mechanism. This multi-step interaction mechanism has previously not been reported in IDPs and provides a better understanding of pH-responsive LLPS.

These findings also have implications in the design of stimuli-responsive protein carriers for various therapeutic treatments. Indeed, the family of GHGXY-containing peptides described herein expands the molecular toolbox of peptides-forming coacervates for therapeutics delivery, in particular offering the added advantages to design and tune pH-responsive carriers de novo as well as the ability to package hydrophilic drugs inside the coacervate microdroplets.

The entire disclosure of each document cited (including patents, patent applications, journal articles, abstracts, laboratory manuals, books, or other disclosures) in the Background, Detailed Description, and Examples is hereby incorporated herein by reference. Further, the hard copy of the sequence listing submitted herewith and the corresponding computer readable form are both incorporated herein by reference in their entireties.

It is to be understood that the disclosures are not limited to particular compositions or methods, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the disclosure pertains. Although any methods and materials similar or equivalent to those described herein can be used in the practice for testing, specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A composition for delivery of an active agent, the composition comprising a peptide coacervate, wherein the peptide coacervate comprises:
 one or more peptides derived from histidine-rich proteins; and
 an active agent encapsulated in the peptide coacervate.

2. The composition of claim 1, wherein the composition is an aqueous liquid two phase formulation, comprising (a) a coacervate colloidal phase comprising the peptides derived from histidine-rich proteins and the active agent; and (b) a dilute aqueous phase.

3. The composition of claim 1, wherein the histidine-rich proteins are histidine-rich beak proteins (DgHBPs).

4. The composition of claim 1, wherein the histidine-rich proteins are selected from the group consisting of DgHBP-1 (SEQ ID NO:1), DgHBP-2 (SEQ ID NO:2), and combinations thereof.

5. The composition of claim 1, wherein the peptides derived from histidine-rich proteins are fragments of DgHBP-1 and/or DgHBP-2 that comprise at least one copy of the peptide motif GHGXY, wherein X is valine (V), leucine (L) or proline (P).

6. The composition of claim 1, wherein the peptides derived from histidine-rich proteins comprise an amino acid sequence selected from the group consisting of:

(1)

$$(GHGX^1Y)_a[(GX^2GX^3A)_b(GHGLX^4)_c(GFA)_d]_f(GHGX^1Y)_a$$

wherein $X^1$ is valine (V), leucine (L) or proline (P), $X^2$ is alanine (A) or proline (P);
 $X^3$ is phenylalanine (F) or tyrosine (Y), $X^4$ is leucine (L), histidine (H), tyrosine (Y) or glycine (G),
 each a is 0 or an integer ≥1;
 each b is 0 or an integer ≥1;
 each c is 0 or an integer ≥1;
 each d is 0 or an integer ≥1;
 f is an integer ≥1;
 with the sum of all a being ≥2 and the sum of all a+b+c+d is ≥4;

(2)

$$(GHGXY)_n,$$

wherein X is valine (V), leucine (L) or proline (P), and n is ≥4;

(3)

$$[(GHGXY)_n(GAGFA)_m]_i\ GHGXY$$

wherein X is valine (V), leucine (L) or proline (P); n is ≥1; m is ≥1; and i≥2;

(4)

$$[(GHGXY)_n(GHGLH)_m]_i\ GHGXY$$

wherein X is valine (V), leucine (L) or proline (P); n is ≥1; m is ≥1; and i≥2;

(5)

$$(GHGXY)_n(GAGFA)_m\ GHGXY$$

wherein X is valine (V), leucine (L) or proline (P); n is ≥1; and m is ≥2;

(6)

$$(GHGXY)_n(GHGLH)_m\ GHGXY$$

wherein X is valine (V), leucine (L) or proline (P); n is ≥1; and m is ≥2; and (7) combinations thereof.

7. The composition of claim 1, wherein the peptides derived from histidine-rich proteins comprise an amino acid sequence selected from the group consisting of:

(i)
```
                                          (SEQ ID NO: 3)
GHGXY GHGXY GHGXY GHGXY GHGXY W
```

(ii)
```
                                          (SEQ ID NO: 4)
GHGXY GHGXY GHGXY GHGXY GHGXY
```

(iii)
```
                                          (SEQ ID NO: 5)
GHGXY GAGFA GHGXY GAGFA GHGXY
```

(iv)
```
                                          (SEQ ID NO: 6)
GHGXY GHGLH GHGLH GHGLH GHGXY
```

(v)
```
                                          (SEQ ID NO: 7)
GHGXY GAGFA GAGFA GAGFA GHGXY
```

(vi)
```
                                          (SEQ ID NO: 8)
GHGXY GHGXY GHGXY GHGXY
```

(vii)
```
                                          (SEQ ID NO: 9)
GHGXY GAGFA GHGLH GFA GHGXY
```

(viii)
```
                                          (SEQ ID NO: 10)
GHGXY GAGFA GHGLH GAGFA GHGXY
```

(ix)
```
                                          (SEQ ID NO: 11)
GHGXY GHGLH GAGFA GHGLH GHGXY
```

(x)
```
                                          (SEQ ID NO: 12)
GHGXY GAGFA GAGFA GHGLH GHGXY
```

-continued (xi)
```
                                             (SEQ ID NO: 13)
GHGXY GHGLH GAGFA GAGFA GHGXY
```

(xii)
```
                                             (SEQ ID NO: 14)
GHGVY GHGVY GHGPY GHGPY GHGLY W
```

(xiii)
```
                                             (SEQ ID NO: 15)
GHGVY GHGVY GHGPY GHGPY GHGLY
```

(xiv)
```
                                             (SEQ ID NO: 16)
GHGLY GAGFA GHGLY GAGFA GHGLY
```

(xv)
```
                                             (SEQ ID NO: 17)
GHGLY GHGLH GHGLH GHGLH GHGLY
```

(xvi)
```
                                             (SEQ ID NO: 18)
GHGLY GAGFA GAGFA GAGFA GHGLY
```

(xvii)
```
                                             (SEQ ID NO: 19)
GHGLY GHGLY GHGLY GHGLY
```

(xviii)
```
                                             (SEQ ID NO: 20)
GHGLY GAGFA GHGLH GFA GHGLY
```

(xix)
```
                                             (SEQ ID NO: 21)
GHGLY GAGFA GHGLH GAGFA GHGLY
```

(xx)
```
                                             (SEQ ID NO: 22)
GHGLY GHGLH GAGFA GHGLH GHGLY
```

(xxi)
```
                                             (SEQ ID NO: 23)
GHGLY GAGFA GAGFA GHGLH GHGLY
```

(xxii)
```
                                             (SEQ ID NO: 24),
GHGLY GHGLH GAGFA GAGFA GHGLY
and
```

(xxiii) combinations thereof.

8. The composition of claim 1, wherein the peptides derived from histidine-rich proteins are 5 to 50 amino acids in length.

9. The composition of claim 1, wherein the active agent is selected from the group consisting of proteins, (poly) peptides, carbohydrates, nucleic acids, lipids, chemical compounds, nanoparticles, and combinations thereof.

10. The composition of claim 1, wherein the active agent is a pharmaceutical or diagnostic agent.

11. The composition of claim 10, wherein the pharmaceutical or diagnostic agent is insulin, doxorubicin, glucose oxidase, magnetic particles, and combinations thereof.

12. The composition of claim 10, wherein the active agent is doxorubicin, a combination of doxorubicin and magnetic nanoparticles, insulin, a combination of insulin and glucose oxidase, and combinations thereof.

13. The composition of claim 1, wherein the composition is a pharmaceutical or diagnostic formulation for administration to a subject.

14. The composition of claim 1, wherein the peptide coacervate is covalently crosslinked.

15. The composition of claim 14, wherein the peptide coacervate is covalently crosslinked via catechol moieties.

16. The composition of claim 1, wherein the pH of the composition is >7.0 and <10.

\* \* \* \* \*